United States Patent [19]

Shibasaki et al.

[11] Patent Number: 4,774,341
[45] Date of Patent: Sep. 27, 1988

[54] BICYCLO(3.3.0)OCTANE DERIVATIVE AND PREPARATION THEREOF

[75] Inventors: Masakatsu Shibasaki, Tokyo; Mikiko Sodeoka; Yuji Ogawa, both of Sagamihara, all of Japan

[73] Assignee: Sagami Chemical Research Center, Tokyo, Japan

[21] Appl. No.: 912,507

[22] Filed: Sep. 29, 1986

Related U.S. Application Data

[62] Division of Ser. No. 641,780, Aug. 17, 1984, Pat. No. 4,644,068.

[30] Foreign Application Priority Data

| Aug. 19, 1983 | [JP] | Japan | 58-150225 |
| Sep. 27, 1983 | [JP] | Japan | 58-177128 |
| Oct. 31, 1983 | [JP] | Japan | 58-202731 |
| Feb. 24, 1984 | [JP] | Japan | 59-32514 |
| Mar. 28, 1984 | [JP] | Japan | 59-58457 |

[51] Int. Cl.[4] .................................. L07C 47/46
[52] U.S. Cl. .................................. 549/214; 549/420; 556/438; 560/119; 562/501
[58] Field of Search ............... 560/116, 119; 562/498, 562/501; 549/420; 556/438

[56] References Cited

U.S. PATENT DOCUMENTS 4,349,689 9/1982 Aristoff ........................ 562/501 X Primary Examiner—Michael L. Shippen
Attorney, Agent, or Firm—Foley & Lardner, Schwartz, Jeffery, Schwaab, Mack, Blumenthal & Evans

[57] ABSTRACT

There are disclosed a bicyclo [3.3.0]octane derivative represented by the formula:

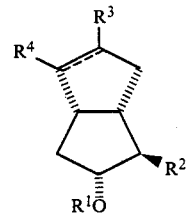

wherein
$R^1$ is a substituent selected from the group consisting of a hydrogen atom and a protective group of a hydroxy group;
$R^2$ is a substituent selected from the group consisting of $-CH_2OR^5$ and

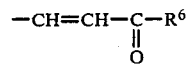

where
$R^5$ is a substituent selected from the group consisting of a hydrogen atom and a protective group of a hydroxy group,
$R^6$ is a substituent selected from the group consisting of an alkyl group, an alkenyl group and an alkynyl group, said substituent being straight, branched or cyclic and having 5 to 10 carbon atoms,
X is a substituent selected from the group consisting of a vinylene group and an acetylene group, and
$R^7$ is a substituent selected from the group consisting of an alkyl group, an alkenyl group, and an alkynyl group said substituent being straight, branched or cyclic and having 5 to 10 carbon atoms; and
$R^3$ is a substituent represented by the formula $-Y-(CH_2)_2-COOR^8$ where
$R^8$ is a hydrogen atom or an alkyl group and
Y is a vinylene group or an alkylene group; and
$R^4$ is a hydroxy group when the compound is an octane derivative, or a hydrogen atom when the compound is an octene derivative; and
dotted line denotes optional presence of a double bond.

The compound of this invention and the process for producing the same are available for producing a 9(0)-methano-Δ6(9.α)-PGI$_1$.

5 Claims, No Drawings

BICYCLO(3.3.0)OCTANE DERIVATIVE AND PREPARATION THEREOF

This is a division of applicaiton Ser. No. 641,780. filed Aug. 17, 1984, now U.S. Pat. No. 4,644,068.

BACKGROUND OF THE INVENTION

This invention relates to a bicyclo[3.3.0]octane derivative and a process for producing the same.

9(0)-methano-$\Delta^{6(9\alpha)}$-PGI$_1$ has a potent platelet aggregation inhibiting action. For example, its action is comparable to chemically unstable PGI2, when human platelet is employed, and it is a compound which can be utilized as a therapeutic or preventive for various diseases of circulatory organs (see the test examples shown below).

In the prior art, as the process for producing 9(0)-methano-$\Delta^{6(9\alpha)}$-PGI$_1$, there have been known (a) the process in which it is produced through the 14 steps using PGE$_2$ as the starting material [Preliminary Text for Lectures in 103rd Annual Meeting in Pharmaceutical Society of Japan, p. 156, (1983)] and (b) the process in which it is produced from 1,3-cyclooctadiene through 19 steps [Preliminary Text for Lectures in 103rd Annual Meeting in Pharmaceutical Society of Japan, p. 157, (1983)]. The former process has the drawback that the starting material is expensive, while the latter process that the desired product is formed as a racemic mixture. Further, both processes (a) and (b) are also disadvantageously very low in the overall yield.

On the other hand, (4'-alkoxycarbonyl-1'-alkenyl)-cis-bicyclo[3.3.0]octene derivative can be led to 9(0)-methano-$\Delta^{6(9\alpha)}$-PGI$_1$ and its various derivatives by highly selective reduction of the double bonds of the α-chains, elimination of the protective group for hydroxyl group and hydrolysis of the ester.

Further, (4'-alkoxycarbonyl-1'-alkenyl)-cis-bicyclo[3.3.0]octene derivative can easily be led to various carbacyclines stereospecifically by 1,4-reduction of conjugated diene.

The above carbacyclines are synthesized according to any of the processes by the Wittig reaction to cis-bicyclo[3.3.0]octane-3-one derivatives [e.g. W. Skuballa and H. Vorbruggen, Angew. Chem. Int. Ed. Engl., 20, 1046 (1981) W. Skuballa et al. (Schering AG), Eur. Pat. 11, 591; Ger. Offen. No. 2,845,770.7; '83 Inflammation Seminar-Prostaglandin Program Preliminary Text, Shinsaku Kobayashi, at p. 37].

However, according to this process, a mixture of 5-E derivative [a] and 5-Z derivative [b] is obtained, and separation of the 5-E derivative [a] which is useful as pharmaceutical remains as the great problem in the synthetic process.

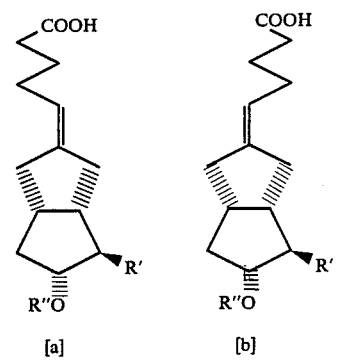

[a]   [b]

SUMMARY OF THE INVENTION

The present inventors have studied extensively to produce 9(0)-methano-$\Delta^{6(9\alpha)}$-PGI and carbacyclines from a cheap starting material at good yield and with optical activity as well as steric configuration specificity, and consequently found that the compound of the present invention and the process for producing the same can be an important intermediate and a process for achieving the object to accomplish the present invention.

This invention concerns a compound of the formula:

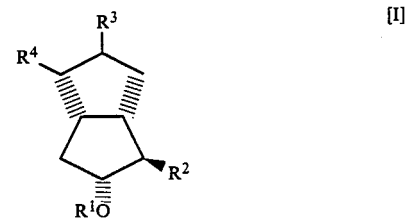

wherein

R$^1$: a hydrogen atom or a protective group of a hydroxy group;

R$^2$: —CH$_2$OR$^5$,

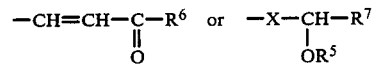

(R$^5$: a hydrogen atom or a protective group of a hydroxy group,

R$^6$: a straight, branched or cyclic alkyl group, alkenyl group or alkynyl group each having 5 to 10 carbon atoms, X: a vinylene group or an acetylene group, R$^7$: a straight, branched or cyclic alkyl group, alkenyl group or alkynyl group each having 5 to 10 carbon atoms);

R$^3$: a formyl group or —Y—(CH$_2$)$_2$—COOR$^8$ (R$^8$: a hydrogen atom or an alkyl group, and Y: a vinylene group or an alkylene group);

R$^4$: a hydroxy group when the compound is an octane derivative, or a hydrogen atom when the compound is an octene derivative;

dotted line: optional presence of a double bond; provided that where R$^z$ is

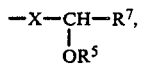

$R^3$ being —$(CH_2)_4$—$COOR^8$ is excluded,
and a process for producing the same.

DESCRIPTION OF THE PREFERRED EMBODIMENTS

The bicyclo[3.3.0]octane derivative represented by the above formula [I] of this invention can be led to (3-oxo-1-alkenyl)-cis-bicyclo[3.3.0]octene derivative by subjecting the bicyclo[3.3.0]octenylaldehyde to the reaction step as hereinafter described or oxidizing the bicyclo[3.3.0]octene derivative and then subjecting the oxidized product to Wittig reaction. The (3-oxo-1-alkenyl)-cis-bicyclo[3.3.0]octene derivative can be led to 9(0)-methano-$\Delta^{6(9\alpha)}$-$PGI_1$ by reducing the ketone, carrying out the deprotection reaction of the hydroxy group and subjecting the ester to hydrolysis (see Reference example shown below).

The bicyclo[3.3.0]octane derivative represented by the above formula [I] of this invention can be stated to be a very useful intermediate in that it can be led to not only the natural type ω-chain of prostaglandin skelton but also to a prostaglandin derivative having a nonnatural type ω-chain having higher activity as disclosed in a literature [Casals-Stenzel, J. et al., Prostaglandins, Leukotrienes Med. 1983, 10 (2), pp. 197–212].

The bicyclo[3.3.0]octane derivative represented by the above formula [I] can be produced according to the reaction schemes as shown below.

The protective group of hydroxy group in this invention may include, for $R^1$, tetrahydropyranyl group, methoxy-methyl group, 4-methoxytetrahydropyranyl group, 1-ethoxyethyl group, 1-methyl-1-methoxyethyl group, t-butyldimethylsilyl group, diphenyl-t-butylsilyl group, benzoyl group, acetyl group, triethylsilyl group, etc. and, for $R^5$, t-butyldimethylsilyl group, benzoyl group, acetyl group, tetrahydropyranyl group, methoxymethyl group, 4-methoxytetrahydropyranyl group, 1-ethoxyethyl group, 1-methyl-1-methoxyethyl group, diphenyl-t-butylsilyl group, triethylsilyl group, etc.

The substituent Y in the substituent $R^3$ may preferably include a vinylene group and an ethylene group.

In the compounds of the present invention, bicyclo[3.3.0]octenylaldehyde derivatives [I'] can be prepared following the reaction schemes shown below:

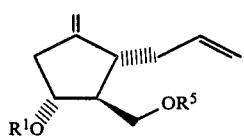
[II]

The first step ↓

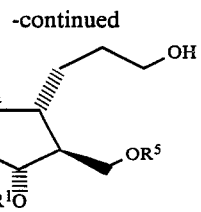
[III]

The second step ↓

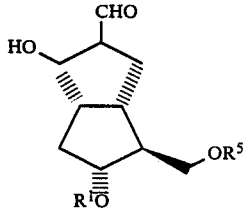
[IV]

The third step ↓

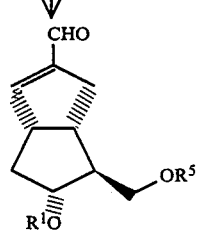
[I']

wherein $R^1$ and $R^5$ are the same as defined above.

[The first step]

This step produces a hydroxymethyl cyclopentane derivative represented by the above formula [III] by hydration of a cyclopentylidene derivative represented by the above formula [II].

The cyclopentylidene derivative represented by the above formula [II] is a compound which can easily be obtained by reducing a Corey's lactone derivative to lactol, which is then subjected to the Wittig reaction to oxidation of the hydroxyl group, followed by the methylenation reaction (see Reference example shown below).

The hydration reaction in this step is conducted out by hydroboration and oxidation. In carrying out hydroboration, there may be employed a hydroborating reagent such as 9-BBN (9-borabicyclo[3.3.1]nonane), thexylborane, disiamylborane, etc. The amount of the hydroborating agent used may be generally 1 to 1.5 equivalent.

The reaction is desired to be carried out in a solvent, preferably an ether type solvent such as tetrahydrofuran, diglyme, diethylether, etc.

The reaction proceeds smoothly at $-25°$ C. to room temperature.

Further, this step carries out oxidation of the product subsequent to the hydroboration without isolation thereof. The oxidation may be carried out by use of an oxidizing agent such as an alkaline hydrogen peroxide, an amine oxide, oxygen, peracid, etc. The amount of the oxidizing agent employed may be 5 to 15 equivalents.

The reaction proceeds smoothly at room temperature to 60° C.

In this step, the compound formed by hydroboration with the use of, for example, 9-BBN may be estimated to have a formula as shown below:

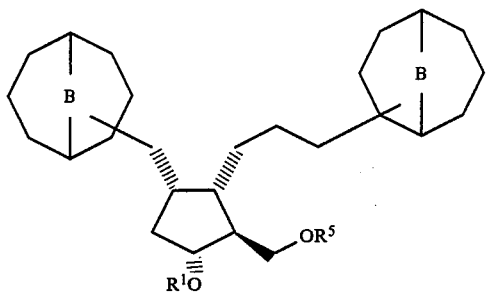

[The second step]

This step produces a β-hydroxyaldehyde derivative represented by the above formula [IV] by oxidation of the hydroxymethyl cyclopentane derivative represented by the above formula [III].

In carrying out oxidation, it is possible to use dimethylsulfoxide-oxalyl chloride, dimethylsulfoxide-a pyridine complex of sulfur trioxide, etc. The amount of the oxidizing agent employed may be generally 1 to 5 equivalents.

The reaction is desired to be carried out in a solvent, for example, a halogenated hydrocarbon such as methylene chloride.

The reaction can proceed smoothly at a temperature, which may differ depending on the oxidizing agent employed, but generally at $-70°$ C. to room temperature.

For obtaining the oxidized product in this step, a tertiary amine such as triethylamine, diisopropylamine, etc. is added into the reaction product and treatment is carried out at $-70°$ C. to room temperature. Under this condition where dialdehyde is formed, intramolecular aldol condensation occurs rapidly to give a β-hydroxyaldehyde derivative represented by the above formula [IV].

After completion of this step, the product is subjected to the next third step without isolation.

[The third step]

This step produces a bicyclo[3.3.0]octenylaldehyde derivative represented by the above formula [I']by dehydrating the β-hydroxyaldehyde derivative represented by the above formula [IV] obtained in the second step as described above in the presence of an acidic catalyst.

Dehydration is required to be carried out in the presence of an acidic catalyst. As the acidic catalyst, an acid-ammonium salt is available. An acid-ammonium salt can be formed from an acid and an amine. The acid available may be exemplified by trifluoroacetic acid, toluenesulfonic acid, camphorsulfonic acid, acetic acid, etc. The amine available may be exemplified by dibenzylamine, diethylamine, dimethylamine, diisopropylamine, piperidine, pyrrolidine, piperazine, etc. These acids and amines may appropriately be selected and combined to be provided for use. Above all, the catalyst comprising a combination of trifluoroacetic acid and dibenzylamine is preferred on account of good yield of the desired product. The amount of the catalyst employed may be about 0.2 equivalent, but it is preferred to employ about one equivalent in order to proceed rapidly the reaction.

The reaction is desired to be carried out in a solvent, for example, an aromatic hydrocarbon such as benzene, toluene, xylene, etc.

The reaction temperature may be selected within the range from room temperature to 100° C., but preferably within the range from 50° C. to 70° C. in order to carry out the reaction smoothly.

The bicyclo[3.3.0]octenylaldehyde derivative obtained as described above can be subjected to the steps A to D as described below, whereby ω-chain can be introduced thereinto.

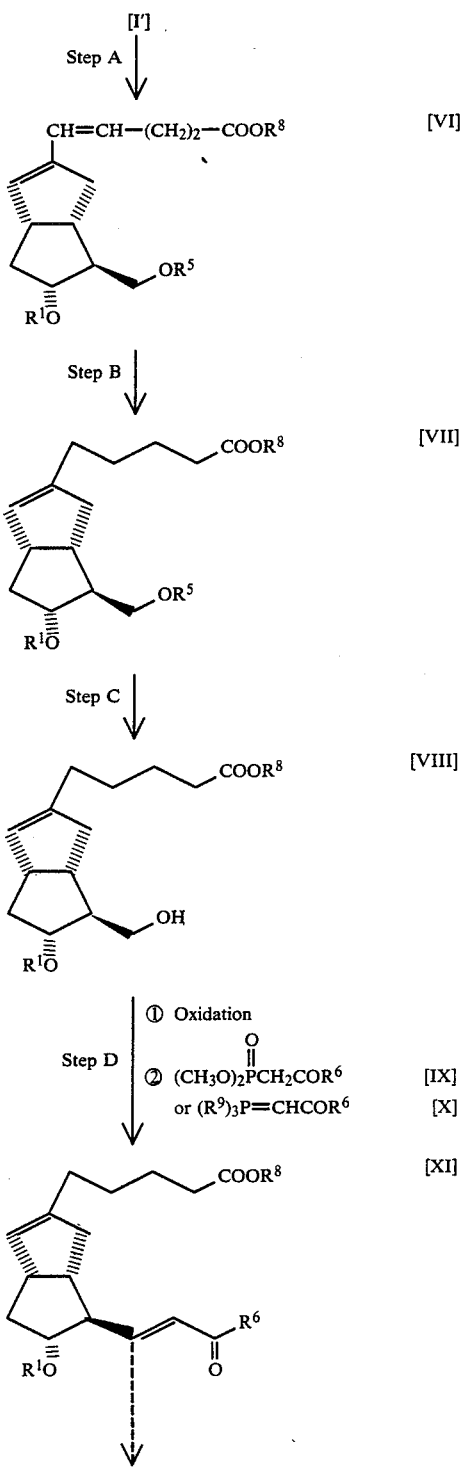

-continued

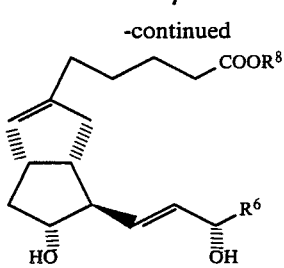

wherein $R^1$ and $R^5$ are the same as defined above, $R^6$ is a straight, branched or cyclic alkyl, alkenyl or alkynyl group each having 5 to 10 carbon atoms, $R^8$ is a hydrogen atom or an alkyl group and $R^9$ is a phenyl group or an alkyl group.

[Step A]

The step produces an alkenylbicyclo [3.3.0] octene derivative represented by the above formula [VI] by carrying out the reaction between the bicyclo[3.3.0]octenylaldehyde derivative represented by the above formula [I'] and 3-carboxypropylphosphonium bromide.

This step is required to be carried out in the presence of a base. The base may include potassium t-butoxide, butyl lithium, sodium salt of dimethylsulfoxide, etc. For carrying out the reaction with good efficiency, it is preferred to employ potassium t-butoxide. The amount of the base employed may be generally 1 to 1.2 equivalent based on the above 3-carboxypropylphosphonium bromide.

The reaction may be carried out preferably in an ether solvent such as tetrahydrofuran, dimethoxyethane, diethyl ether, etc. The solvent is not particularly limited, provided that it does not interfere with the reaction.

The reaction temperature may be selected within the range from 0° C. to 50° C., at which the reaction can proceed smoothly.

The compound obtained in this step is formed generally as a free carboxylic acid, but it can be isolated as an ester by use of the condition of diazomethane or alkyl halide-diazabicycloundecene-acetonitrile for the reactions in the subsequent step et seq. Conversion to ester may be conducted according to the method easily done by those skilled in the art.

[Step B]

This step produces a bicyclo[3.3.0]octene derivative represented by the above formula [VII] in which only one of the olefins is selectively reduced by catalytic reduction of the alkenylbicyclo[3.3.0]octene derivative represented by the formula [VI] obtained in the previous step A.

The available catalysts include palladium catalysts such as palladium-carbon, palladium black, etc., Wilkinson catalysts, platinum, nickel, etc. The catalyst may be sufficiently employed in the so-called catalytic amount.

In practicing this step, hydrogen may be allowed to react with the compound under normal pressure or under pressurization.

The reaction may be carried out preferably in a solvent, for example, an alcohol solvent such as methanol, ethanol, etc. or an ester solvent such as ethyl acetate, etc.

The reaction can proceed smoothly at a temperature selected within the range from −25° C. to room temperature.

[Step C]

This step produces a hydroxymethylbicyclo[3.3.0]octene derivative represented by the above formula [VIII] by selective deprotection of $R^5$ of the bicyclo[3.3.0]octene derivative represented by the above formula [VII] obtained in the previous step B.

In carrying out deprotection, when $R^5$ is a silyl group, tetra-n-butylammonium fluoride may be used as the deprotecting agent, while potassium carbonate may be used, when it is benzoyl group or acetyl group.

The reaction should desirably be conducted in a solvent. When tetra-n-butylammonium fluoride is used as the deprotecting agent, an ether solvent such as tetrahydrofuran, dimethoxyethane, ethyl ether, etc. may preferably be used. On the other hand, when potassium carbonate is used as the deprotecting agent, an alcohol solvent such as methanol, ethanol, etc. may preferably be used.

The reaction can proceed smoothly at −25° C. to room temperature.

[Step D]

This step produces a (3-oxo-1-alkenyl)-cis-bicyclo[3.3.0]octene derivative represented by the above formula [XI] by oxidizing the hydroxymethylbicyclo[3.3.0]octene derivative represented by the above formula [VIII] obtained in the previous step C and subsequently allowing the resultant product to react with a compound represented by the above formula [IX] or the above formula [X].

The oxidation in this step is required to be carried out in the presence of an oxidizing agent. The oxidizing agent may include Collins reagent, dimethyl sulfoxidepyridine complex of sulfur trioxide, pyridinium chlorochromate, dimethyl sulfoxide-oxalyl chloride, etc. The amount of the oxidizing agent employed may be 7 to 10 equivalents in the case of Collins reagent, and 1 to 5 equivalents in the case of other oxidizing agents.

The reaction should desirably be carried out in a solvent, preferably in a halogenated hydrocarbon such as methylene chloride, chloroform, etc.

The reaction can proceed smoothly at a temparature within the range from −70° C. to room temperature.

In this step, the product obtained by oxidation is not isolated but subsequently subjected to the reaction with a compound represented by the above formula [IX] or the above formula [X]. The compounds represented by the above formula [IX] include, for example, dimethyl(2-oxo-heptyl) phosphonate, dimethyl(2-oxo-3-methylheptyl)phosphonate, dimethyl(2-oxo-3,3-dimethylheptyl)phosphonate, dimethyl(2-oxo-4,8-dimethyl-7-nonenyl)phosphonate, dimethyl(2-oxo-4,4,8-trimethyl-7-nonenyl)phosphonate, dimethyl(2-oxo-2-cyclopentylethyl)phosphonate and the like. The compounds represented by the above formula [X] include tributylphosphine-2-oxoheptylidene, tributylphosphine-2-oxo-3-methylheptylidene, tributylphosphine-2-oxo-3,3-dimethylheptylidene, tributylphosphine-2-oxo-4,8-dimethyl-7-nonenylidene, tributylphosphine-2-oxo-4,4,8-trimethyl-7-nonenylidene, tributylphosphine-2-oxo-2-cyclopentylethylidene and the like. When the compound represented by the above formula [X] is selected as the starting material, it is preferred to carry out the reaction in the presence of a base, such as sodium hydride, butyl lithium, potassium t-butoxide, etc. in order to obtain the desired product at good yield.

The reaction should desirably be conducted in a solvent, e.g. an ether solvent such as tetrahydrofuran, dimethoxyethane, diethyl ether, etc. or an aromatic solvent such as benzene, toluene, xylene, etc.

The reaction temperature may be within the range from −25° oC to 50° C. when employing a compound represensted by the formula [IX] or within the range from 20° C. to 150° C. when employing a compound represented by the formula [X].

The compound obtained by oxidation in this step may be estimated to be a compound represented by the formula:

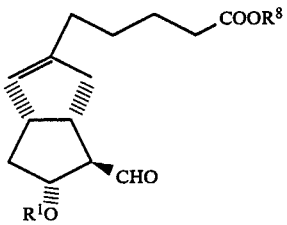

wherein $R^1$ is a protective group for hydroxy group and $R^8$ is a hydrogen atom or an alkyl group.

In the present invention, the (1-alkenyl)-bicyclo[3.3.0]octenyl derivative represented by the following formula [I-a]:

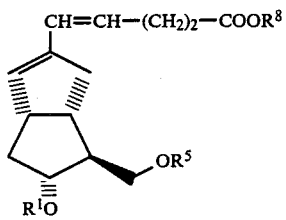

CH=CH—(CH$_2$)$_2$—COOR$^8$    [I-a]

can be produced as follows.

That is, in the presence of a base, bicyclo[3.3.0]octenylaldehyde represented by the formula [I']:

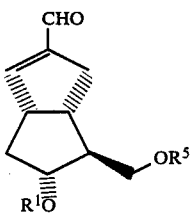

wherein $R^1$ and $R^5$ are a hydrogen atom or protective groups a hydroxy group, is allowed to react with a 3-carboxypropylphosphonium halilde represented by the formula [XII]:

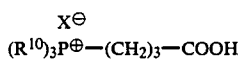

$X^\ominus$    [XII]
$(R^{10})_3P^\oplus$—(CH$_2$)$_3$—COOH wherein $R^{10}$ is an alkyl group or an aryl group, and X is a halogen atom, followed by esterification if desired, to produce a (1-alkenyl)-bicyclo[3.3.0]octene derivative.

The bicyclo[3.3.0]octenylaldehyde derivative represented by the formula [I'] can be synthesized easily from Coley lactone which the typical intermediate for various prostaglandins (see Reference example shown below). In the above formula [I'], $R^1$ and $R^5$ may include hydrogen atom, tetrahydropyranyl group, t-butyldimethylsilyl group, 1-ethoxyethyl group, diphenyl-t-butylsilyl group, methoxymethyl group, 1-methyl-1-methoxyethyl group, 4-methoxytetrahydropyranyl group, methyl group, benzyl group, benzoyl group, acetyl group, β-methoxyethoxymethyl group, triethylsilyl group, etc.

The 3-carboxypropylphosphonium halide represented by the above formula [XII] can be prepared from, for example, 4-bromobutanoic acid and triphenylphosphine [W. Seidel, J. Knolle, and H. J. Schäfer, Chem. Ber., 110, 3544 (1977)]. $R^{10}$ in the above formula [XII] may be, for example, an alkyl group such as butyl or an aryl group such as a phenyl, and X may be chlorine atom, bromine atom or iodine atom.

The present invention is required to be carried out in the presence of a base. Examples of the base may be organic bases such as potassium t-butoxide, sodium t-amyloxide, sodium methoxide, sodium ethoxide, sodium salt of dimethyl sulfoxide (DMSO), potassium salt of DMSO, butyl lithium, sec-butyl lithium, t-butyl lithium, phenyl lithium, sodium hydride, potassium hydride, lithium diisopropylamide, lithium diethylamide, sodium amide and the like, and inorganic bases such as sodium hydroxide, potassium hydroxide, potassium carbonate and the like. The amount of the base employed may be sufficiently be 2 to 3 mole equivalents based on the bicyclo[3.3.0]octenylaldehyde derivative represented by the above formula [I'].

The present invention should desirably be carried out in a solvent. The solvent may be an ether solvent such as tetrahydrofuran, dimethoxyethane, ether, 2-methoxyethyl ether, etc., an aromatic solvent such as toluene, benzene, etc., or a polar solvent such as DMSO, HMPT, DMF, etc., when employing an organic base; or alternatively a halogenic solvent such as methylene chloride, chloroform, etc. or a solvent mixture of an aromatic solvent such as toluene, benzene, etc. with water, when employing an inorganic base.

When an inorganic base is employed, the reaction system consists of two layers. For the purpose of effective action of these bases, it is preferred to carry out the reaction in the presence of a catalyst for inter-phase migration generally employed for two-layer system reaction such as tetramethylammonium bromide, tetrabutylammonium iodide, etc., whereby the desired product can be obtained with good efficiency. The reaction can proceed smoothly by selecting a temperature within the range from −78° C. to 100° C. In the present invention, esterification may be conducted, if desired.

It is possible to derive an alkyl ester of the compound represented by the above formula [I-a] wherein $R^8$ represents a hydrogen atom. That is, the compound obtained by the above reaction may be allowed to react with diazomethane in an ether solvent to be quantitatively converted into a methyl ester derivative, which can in turn be allowed to react with various alkyl halides such as ethyl bromide, propyl bromide, butyl bromide, etc. in acetonitrile in the presence of 1,8-diazabicyclo[5,4,0]undecene (BU) to be converted to corresponding ethyl ester, propyl ester and butyl ester derivatives, respectively. The reaction can proceed smoothly by selecting a temperature within the range from −25° C. to 100° C.

In the present invention, the (4,-alkoxycarbonyl-1,'-alkenyl)-cis-bicyclo[3.3.0]octene derivative represented by the following formula:

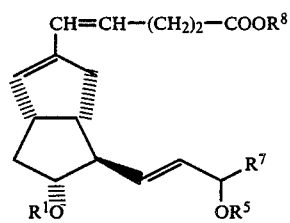 [I-b]

can be produced according to the following steps:

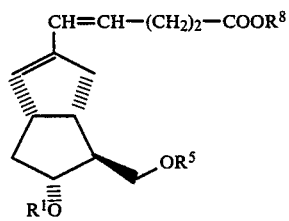 [VI']

 The first step

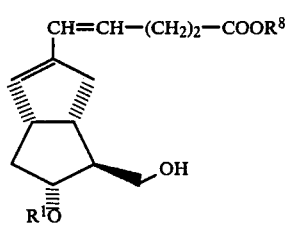 [VIII]

The second step
① Oxidation
② $(CH_3O)_2\overset{O}{\overset{\|}{P}}CH_2COR^7$ [IX]

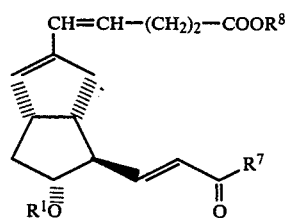 [XI']

 The third step

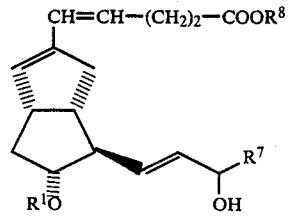 [I-c]

 The fourth step

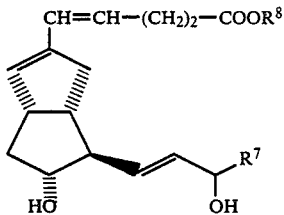 [I-d]

The fifth step

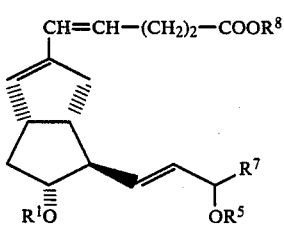 [I-b]

wherein $R^1$, $R^5$, $R^7$, and $R^8$ are the same as defined above.

[The first step]

- This step produces a hydroxymethyl derivative [VIII] by selective elimination of the protective group for the primary hydroxy group of a conjugated diene derivative represented by the above formula [VI']. Deprotection of this step is carried out with fluoride ions when the silyl group is protected, and tetrabutylammonium fluoride, potassium fluoride, etc. may be used. This step should desirably be conducted in a solvent, preferably an ether solvent such as tetrahydrofuran. In this step, the reaction can proceed smoothly at a temperature within the range from −25° to 100° C.

[The second step]

This step produces an α,β-unsaturated ketone by oxidizing the hydroxymethyl derivative represented by the formula [VIII] obtained in the first step, and then allowing the resultant product with a compound represented by the above formula [IX].

This step can be carried out under the same conditions in the step D for introducing ω-chain into the bicyclo 3.3.0]octenylaldehyde derivative as described above.

The compounds represented by the above formula [IX] may include, for example, dimethyl(2-oxo-3-methyl-5-heptynyl)phosphonate, dimethyl(2-oxo-4(R)-methyl-8-methyl-7-nonenyl)phosphonate and the like. This step may preferably be conducted in the presence of a base for obtaining the desired compound with good efficiency. For example, a base such as sodium hydride, potassium hydride, butyl lithium, potassium t-butoxide, etc. may be employed.

The compound obtained by oxidation in this step may be estimated to be a compound represented by the formula:

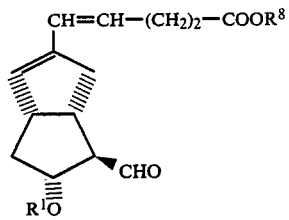

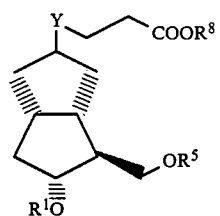

[The third step]

This step produces an allyl alcohol derivative by reduction of the carbonyl group of the α,β-unsatuated ketone represented by the above formula [XI'] obtained in the second step. Reduction in this step is required to be carried out in the presence of a reducing agent. The reducing agent may include sodium borohydride, diisobutylaluminum-2,6-di-t-butyl-4-methyl-phenoxide, etc. The amount of the reducing agent used may be 1 to 15 equivalents. The reaction should desirably be carried out in a solvent, e.g. an alcohol solvent such as methanol, ethanol and the like, an aromatic hydrocarbon solvent such as benzene, toluene, etc. The reaction can proceed smoothly at a temperature in the range from $-78°$ C. to room temperature. The allyl alochol derivative obtained in this step is a mixture of α-isomer and β-isomer.

[The fourth step]

This step produces a diol derivative by elimination of the protective group of the secondary hydroxyl group of the allyl alcohol derivative represented by the formula [I-c] obtained in the third step. Deprotection in this step is carried out in the presence of an acid. The acid to be employed may be acetic acid, pyridinium salt of p-toluene sulfonic acid, etc. The reaction should desirably be conducted in a solvent such as THF-water, ethanol-water, etc. The reaction can proceed smoothly at room temperature to 100° C. The diol derivative obtained in this step can be easily separated into isomers at the 15-position (prostaglandin numbering) into a highly polar isomer 15α and a lowly polar isomer 158α.

[The fifth step]

This step protects the two hydroxy groups of the diol derivative represented by the above formula [I-d] obtained in the fourth step, if desired. The protective group to be employed may be, for example, t-butyldimethylsilyl group, triethylsilyl group, tetrahydropyranyl group, 1-ethoxyethyl group, diphenyl-t-butylsilyl group, 1-methyl-1-methoxyethyl group, etc. It is desired to employ the condition of t-butyldimethylsilylchlorideimidazole-DMF in the case of t-butyldimethylsilyl group; of triethylsilyl chloride-pyridine in the case of triethylsilyl group; of dihydropyrane-catalytic amount of p-toluene sulfonic acid-methylene chloride in the case of tetrahydropyranyl group; of ethyl vinyl ether-catalytic amount of p-toluene sulfonic acid-methylene chloride in the case of 1-ethoxyethyl group; etc.

The reaction can proceed readily at 0° C. to 100° C.

The (4'-alkoxycarbonyl-1'-alkenyl) -cis-bicyclo-]3.3.0]-octene derivative of the present invention has an asymmetric carbon in the molecule, and the present invention is inclusive of the R-configuration or the S-configuration or a mixture of those at any desired ratio.

In the present invention, a bicyclo[3.3.0]octane derivative represented by the following formula [I-e]:

can be further produced according to the following steps:

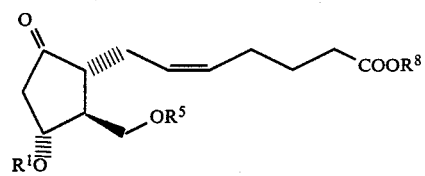

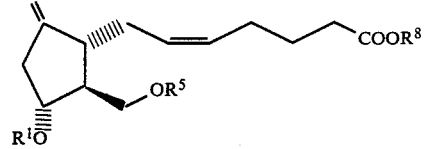

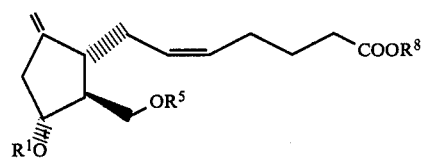

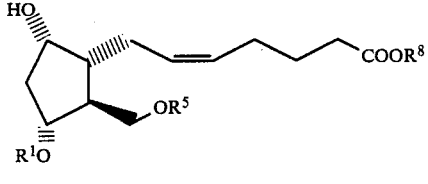

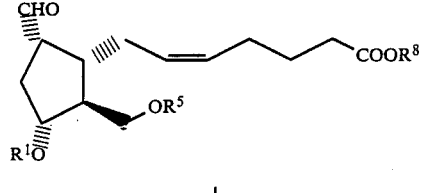

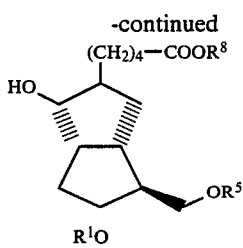

wherein $R^1$, $R^5$ and $R^8$ are the same as defined above.

[The first step]

This step produces a cyclopentylidene derivative represented by the formula [XIV] by methylenation of the cyclopentanone derivative represented by the above formula [XIII].

The cyclopentanone derivative represented by the above formula [XIII] is a compound which can be obtained easily by reducing a Coley lactone derivative into a lactol, subjecting the lactol to the Wittig reaction, converting the carboxyl group into ester group and oxidizing the hydroxy group (see Reference examples shown below).

The group $R^8$ in the formula [XIII] may be, for example, an alkyl group such as methyl, ethyl, etc.

The methylenation in this step may be carried out by use of a mixed reagent of methylene bromide-titanium tetrachloride-zinc [L. Lombardo, Tetrahedron Lett., 23, 4293 (1982)] or Johnson reagent [C. R. Johnson, J. R. Shanklin, R. A. Kirchoff, J. Am. Chem. Soc., 95, 6462 (1973)]. The reaction should desirably be carried out in a solvent, for example, a solvent mixture such as a halogenic solvent (e.g. methylene chloride)—an ether solvent (e.g. tetrahydrofuran) in the case of using the former reagent, while an ether solvent in the case of the latter reagent. The reaction can proceed smoothly at $-80°$ C. to $60°$ C., but room temperature is preferred because the reaction can be carried out without heating or cooling.

When the protective group $R^1$ in the cyclopentylidene derivative is subjected to subsequent steps, particularly the fourth step, it is preferably converted to a protective group which is high in thermal stability, such as t-butyldimethylsilyl group, diphenyl-t-butylsilyl group, methyl group, etc.

[The second step]

This step can be carried out according to the same procedure as in the first step in preparation of the bicyclo[3.3.0]octenylaldehyde derivative as described above.

Further, as described above, this step oxidizes the product without isolation subsequent to hydroboration. In oxidation, an oxidizing agent selected from peroxides of hydrogen peroxide, peracetic acid, perbenzoic acid, etc. may be employed. When a peroxide is employed as the oxidizing agent, the peroxide is desired to be in a basic state and a base such as caustic soda may be employed for this purpose. The amount of the oxidizing agent to be employed may be generally 5 to 15 equivalents. The reaction can proceed smoothly at $-20°$ to $60°$ C., but the reaction at room temperature is preferable because of simple operation.

[The third step]

This step produces a formylcyclopentane derivative represented by the above formula [XVI] by oxidation of the hydroxymethylcyclopentane derivative represented by the above formula [XV] obtained in the second step.

In carrying out oxidation, it is possible to use an oxidizing agent such as pyridinium chlorochromate (PCC) in the presence of sodium acetate, Collins reagent, pyridinium dichromate (PDC), dimethyl sulfoxide (DMSO)-pyridinium complex of sulfur trioxide, DMSO-oxalyl chloride, etc. The amount of the oxidizing agent employed is different depending on the oxidizing agent, but generally 1 to 8 equivalent.

The reaction should desirably be conducted in a solvent, for example, a halogenic solvent such as methylene chloride, chloroform, etc. The reaction temperature is different depending on the oxidizing agent employed. When PCC, Collins reagent, PDC or DMSO-pyridinium complex of sulfur trioxide is employed, the reaction can proceed readily at $-20°$ C. to $30°$ C. In the case of DMSO-oxalyl chloride, the raction can proceed smoothly at $-70°$ C. to room temperature.

[The fourth step]

This step produces an alkenylbicyclo[3.3.0]octane derivative represented by the above formula [I-a] by treating the formylcyclopentane derivative represented by the above formula [XVI] obtained in the third step under heating.

This step is the so-called thermal heteroene reaction and the heating condition may be selected within the range of from $120°$ to $300°$ C. However, for carrying out the reaction efficiently, the range from $150°$ to $250°$ C. is preferred.

The reaction should desirably be conducted in a solvent, for example, an aromatic hydrocarbon such as benzene, toluene, xylene and the like.

[The fifth step]

This step produces an alkylbicyclo[3.3.0]octane derivative represented by the above formula [I-g] by catalytic reduction of the alkenylbicyclo[3.3.0]octane derivative represented by the above formula [I-f] obtained in the fourth step.

The catalysts available include palladium catalysts such as palladium-carbon, palladium black, etc., Wilkinson catalyst, platinum, nickel, etc. It is sufficient to employ the catalyst in the so-called catalytic amount.

In practicing this step, hydrogen may be allowed to react with the compound either at normal pressure or under pressurization.

The reaction should desirably be conducted in a solvent, for example, an alcohol solvent such as methanol, ethanol, etc. or an ester solvent such as ethyl acetate.

The reaction can proceed smoothly at a temperature which may be selected within the range from $-25°$ C. to room temperature.

The present invention is described in more detail by referring to the following Reference examples and Examples.

REFERENCE EXAMPLE 1

[2-Oxa-3-oxo-6-exo-t-butyldimethylsilyloxymethyl-7-endotetrahydropyranyloxybicyclo[3.3.0]octane] (2.22 g, 6 mmol) was dissolved in toluene (10 ml) under argon gas atmosphere, and the solution was cooled to $-75°$ C. To the solution was added diisobutylalminum hydride (25 g/100 ml hexane solution; 5.1 ml, 9 mmol) and the mixture was stirred at $-75°$ C. for 70 minutes. Methanol was added at $-75°$ C. until generation of hydrogen had not been admitted and the temperature of the mixture was raised to room temperature. After the mixture was diluted with ethyl acetate (130 ml), washed with a saturated saline solution (20 ml×4 times). The mixture was dried with anhydrous magnesium sulfate, distilled out the solvents to obtain [1-2-oxa-3-hydroxy-6-exo-t-butyldimethylsilyloxymethyl-7-endo-tetrahydropyranyloxybicyclo[3.3.0]octane] (2.33 g, Yield: 100%).

IR (neat): 3430, 2950, 2860, 835 cm$^{-1}$.

NMR δ (CDCl$_3$): 5.70–5.30 (m, 1H), 4.85–4.55 (m, 2H), 4.40–3.25 (m, 5H), 0.90 (s, 9H).

Mass m/z (%): 213 (5), 159 (17), 85 (100), 75 (19), 73 (13).

$[\alpha]_D^{20} = -28°$ (c=1.98, MeOH).

REFERENCE EXAMPLE 2

Potassium t-butoxide (3.16 g, 28.2 mmol) was dissolved in THF (50 ml) under argon gas atmosphere. To the solution was added at room temperature methyltriphenylphosphonium bromide (10.07 g, 28.2 mmol) which was previously dried enough at 100° C. under reduced pressure. After 5 minutes stirring, to the mixture was added [1-2-oxa-3-hydroxy-6-exo-t-butyldimethylsilyloxymethyl-7-endo-tetrahydropyranyloxybicyclo[3.3.0]octane (3.40 g, 9.1 mmol) in THF solution (30 ml) and the mixture was stirred at room temperature for 20 minutes. After a saturated aqueous ammonium chloride solution was added the mixture, THF was distilled out therefrom under reduced pressure. The resultant aqueous layer was extracted with ether and the extract was washed with a saturated saline solution. After dryness with anhydrous magnesium sulfate, ether was distilled out. The residue was purified through silica gel column chromatography (ether:n-hexane=2:3) to obtain [d-2α-allyl-3β-t-butyldimethylsilyloxymethyl-4α-tetrahydropyranyloxy-1α-cyclopentanol] (3.18 g, 94%).

IR (neat): 3500, 2950, 2870, 1640, 835 cm$^{-1}$.

NMR δ (CDCl$_3$): 5.80 (m, 1H), 5.00 (m, 2H), 4.65 (bs, 1H), 4.30–3.00 (m, 6H), 0.90 (s, 9H).

Mass m/z (%): 285 (1), 229 (1), 211 (3), 159 (26), 85 (100), 75 (21), 73 (13).

$[\alpha]_D^{20} = +20°$ (c=2.44, MeOH).

REFERENCE EXAMPLE 3

To methylene chloride (40 ml) was dissolved [d-2α-allyl-3β-t-butyldimethylsilyloxymethyl-4α-tetrahydropyranyloxy-1α-cyclopentanol] (3.16 g, 8.5 mmol) and then sodium acetate (280 mg, 2.6 mmol) and Celite (3.36 g) were added thereto. To the resultant mixture was added, under argon gas atmosphere at 0° C., pyridinium chlorochromate (3.68 g, 17.1 mmol) and stirred at 0° C. for 18 hours. The reaction mixture was diluted with ether and purified through florisil column chromatography (ether:n-hexane=1:3 to 3:1) to obtain [1-2α-allyl-3β-t-butyldimethylsilyloxymethyl-4α-tetrahydropyranyloxy-1-cyclopentanone] (2.82 g, Yield: 90%).

IR (neat): 2950, 2880, 1748, 1642, 840 cm$^{-1}$.

NMR δ (CDCl$_3$): 5.70 (m, 1H), 5.03 (d, J=17 Hz, 1H), 5.00 (d, J=11 Hz, 1H), 4.65 (bs, 1H), 4.30 (m, 1H), 3.30–4.00 (m, 4H), 0.90 (s, 9H).

Mass m/z (%): 209 (17), 159 (17), 85 (100), 75 (35), 73 (23), 41 (17).

$[\alpha]_D^{20} = -55°$ (c=2.19, MeOH).

REFERENCE EXAMPLE 4

[1-2α-allyl-3β-t-butyldimethylsilyloxymethyl-4α-tetrahydropyranyloxy-1-cyclopentanone] (2.79 g, 7.57 mmol) was dissolved in methylene chloride (26 ml) and to the solution was added a zinc-titanium chloride-methylene bromide reagent (Zn-TiCl$_4$-CH$_2$Br$_2$/THF, 46 ml) at room temperature. After disappearance of the starting materials had been confirmed by using TLC, the reaction mixture was poured into a mixed solution of saturated aqueous sodium hydrogencarbonate solution (500 ml) and ether (500 ml). After the ether layer was separated from the mixture, the aqueous layer was further extracted with ether. The ether layers were combined, and the mixture was washed with a saturated saline solution, dried over anhydrous magnesium sulfate and evaporated out the solvents. The residue was purified through silica gel column chromatography (ether:n-hexane=1:10) to obtain [1-2α-allyl-3β-t-butyldimethylsilyloxymethyl-4α-tetrahydropyranyloxy-1-cyclopentylidene] (2.48 g, Yield: 90%).

IR (neat): 2950, 2870, 1660, 1640, 835 cm$^{-1}$.

NMR δ (CDCl$_3$): 5.60 (m, 1H), 4.75–5.20 (m, 4H), 4.63 (bs, 1H), 3.30–4.30 (m, 5H), 0.90 (s, 9H).

Mass m/z (%): 159 (18), 133 (11), 85 (100), 75 (19), 73 (13).

$[\alpha]_D^{20} = -43°$ (c=2.84, MeOH).

REFERENCE EXAMPLE 5

9-Borabicyclo[3.3.0]nonane (dimer, 2.472 g, 20.3 mmol) was suspended in THF (28 ml) under argon gas atmosphere. A solution of [1-2α-allyl-3β-t-butyldimethylsilyloxymethyl-4α-tetrahydropyranyloxy-1-cyclopentylidene] (2.476 g, 6.75 mmol) dissolved in THF (45 ml) was added dropwise to the aforesaid suspension under ice-cooling, the mixture was stirred at 5° to 10° C. for 7.5 hours. To the mixture were added a 6N aqueous sodium hydroxide solution (13.5 ml, 81 mmol) and a 30% aqueous hydroperoxide solution (11.5 ml, 101.3 mmol) and stirred at 60° C. for 1.5 hours. After evaporation of THF under reduced pressure, the resultant mixture was extracted with ethyl acetate. The separated organic layer was washed successively with an aqueous sodium thiosulfate solution and a saturated saline solution. The thus treated mixture was dried over anhydrous magnesium sulfate and then distilled out the solvents. The residue was purified through silca gel column chromatography (ether:methanol=40:1) to obtain [d-1α-hydroxymethyl-2α-(3-hydroxypropyl)-3β-t-butyldimethylsilyloxymethyl-4α-tetrahydropyranyloxyl-1-cyclopentane] (2.65 g, Yield: 97%).

IR (neat): 3400, 2940, 2860, 835 cm$^{-1}$.

NMR δ (CDCl$_3$): 4.65 (bs, 1H), 4.10 (m, 1H), 3.15–3.95 (m, 8H), 0.90 (s, 9H).

Mass m/z (%): 159 (19), 149 (18), 133 (19), 121 (13), 105 (15), 93 (10), 91 (10), 85 (100), 79 (11), 75 (34), 73 (18), 67 (17), 57 (24), 55 (16), 43 (17), 41 (21).

$[\alpha]_D^{20} = +2°$ (c=1.65, MeOH).

REFERENCE EXAMPLE 6

In the method as described in Reference examples 1 to 5, the same procedures were carried out as in Reference examples 1 to 5 except that [2-oxa-3-oxo-6-exo-(1-methyl-1-methoxyethyloxymethyl)-7-endo-tetrahydropyranyloxybicyclo[3.3.0]octane (1.11 g, 3.88 mmol) was employed as the starting material to yield [1α-hydroxymethyl-2α-(3-hydroxypropyl)-3β-(1-methyl-1-methoxyethyloxymethyl)-4α-tetrahydropyranyloxycyclopentane (1.13 g, Yield: 81%).

IR (neat): 3400, 2940, 2860, 831 cm$^{-1}$.

NMR δ (CDCl$_3$): 4.61 (bs, 1H), 3.40–4.20 (m, 9H), 3.20 (s, 3H), 1.34 (s, 6H).

Mass m/z (%): 360, 342, 328, 257.

EXAMPLE 1

Oxalyl chloride (1.88 ml, 21.6 mmol) was dissolved in 55 ml of methylene chloride at −60° C. under argon gas atmosphere. To the solution was added a solution of dimethyl sulfoxide (3.39 ml, 47.7 mmol) dissolved in methylene chloride (15 ml). After the mixture was stirred at −60° C. for 20 minutes, a solution of [d-1α-hydroxymethyl-2α-(3-hydroxypropyl)3β-t-butyldimethylsilyloxymethyl-4α-tetrahydropyranyloxy-1-cyclopentane] (1.48 g, 3.67 mmol) dissolved in methylene chloride (30 ml) was added thereto. After the mixture was stirred at −60° C. for 20 minutes, triethylamine (15.36 ml, 110.1 mmol) was added thereto and the temperature of the mixture was raised to room temperature. Water was poured into the mixture and the mixture was extracted with methylene chloride. The separated organic layer was wahsed with an aqueous saline solution and dried over anhydrous magnesium sulfate. Evaporation of the solvent to obtain [2-hydroxy-3-formyl-6-exo-t-butyldimethylsilyloxymethyl-7-endo-tetrahydropyranyloxybicyclo[3.3.0]octane] (1.19 g, Yield: 81%). According to spectrum data, this compound was equilibrium compound between β-hydroxyaldehyde and lactol.

IR (KBr): 3450, 2950, 2870, 2750, 1730, 835 cm$^{-1}$.

NMR δ (CDCl$_3$): 9.75 (trace), 4.65 (m, 1H), 3.10–4.50 (m, 6H), 0.90 (s, 9H).

Mass m/z (%): 313 (trace, M$^+$ −85), 159 (15), 85 (100), 75 (17), 73 (12), 57 (12), 47 (11).

EXAMPLE 2

[2-Hydroxy-3-formyl-6-exo-t-butyldimethylsilyloxymethyl-7-endo-tetrahydropyranyloxybicyclo[3.3.0]octane] (1.19 g, 2.97 mmol) was dissolved in benzene (4.5 ml). To the solution was added dimethylammonium trifluoroacetate (1.14 g, 3.66 mmol) under argon gas atmosphere and the mixture was stirred at 50° to 70° C. for 16 hours. After the reaction mixture was allowed to stand for cooling, water (50 ml) was added thereto and the mixture was extracted with ether. After an ether layer was separated, the ether layer was washed successively with a saturated aqueous ammonium chloride solution, a saturated aqueous sodium hydrogencarbonate solution and water. The ether layer was dried over anhydrous magnesium sulfate and then evaporation of the solvent was carried out. The residue was purified through silica gel column chromatography (ether:n-hexane=1:1) to obtain [l-3-formyl-6-exo-t-butyldimethylsilyloxymethyl-7-endo-tetrahydropyranyloxybicyclo[3.3.0]oct-2-ene] (1.03 g, 82%).

IR (neat): 2950, 2870, 1680, 1620, 835 cm$^{-1}$.

NMR δ (CDCl$_3$): 9.78 (s, 1H), 6.71 (d, J=2 Hz, 2H), 4.60 (bs, 1H), 3.00–4.20 (m, 6H), 0.90 (s, 9H).

Mass m/z (%): 295 (1), 159 (33), 85 (100), 75 (26), 73 (19), 67 (12), 57 (14), 45 (14), 43 (22).

[α]$_D^{20}$ = −77° (c=2.77, MeOH).

EXAMPLE 3

Oxalyl chloride (1.88 ml, 21.6 mmol) was dissolved in methylene chloride (55 ml) under argon gas atmosphere, and to the solution was added a solution of DMSO dissolved in methylene chloride (DMSO 3.39 ml, 47.7 mmol/15 ml CH$_2$Cl$_2$) at −60° C. for periods of 5 minutes. After the mixture was stirred at −60° C. for 20 minutes, a solution of d-1α-hydroxymethyl-2α-(3-hydroxypropyl)-3β-t-butyldimethylsilyloxymethyl-4α-tetrahydropyranyloxycyclopentane (1.48 g, 3.67 mmol) dissolved in methylene chloride (30 ml) was added dropwise for periods of 5 minutes. The mixture was further stirred at −60° C. for 20 minutes, and then triethylamine (15.36 ml, 110.1 mmol) was added thereto and the temperature of the mixture was raised to room temperature. To the mixture was further added dibenzylammonium trifluoroacetate (1.14 g, 3.66 mmol) and methylene chloride was distilled out therefrom. To the residue was added benzene (45 ml) to dissolve and the solution was stirred, under argon gas atmosphere, at 50° to 70° C. for 16 hours. To the mixture was added water (50 ml) and extracted with ether. A separated ether layer was washed successively with a saturated aqueous ammonium chloride solution, a saturated aqueous sodium hydrogencarbonate solution and water, dried over anhydrous magnesium sulfate and then distilled out the solvent therefrom. The residue was purified through silica gel column chromatography to obtain l-3-formyl-6-exo-t-butyldimethylsilyloxymethyl-7-endo-tetrahydropyranyloxy-bicyclo[3.3.0]oct-2-ene (1.03 g, 74%).

EXAMPLE 4

In the method as described in Example 3, the same procedures were carried out as in Example 3 except that [1α-hydroxymethyl-2α-(3-hydroxypropyl)-3β-(1-methyl-1-methoxyethyloxymethyl)-4α-tetrahydropyranyloxycyclopentane] (1.13 g, 3.14 mmol) was employed as the starting material to obtain [3-formyl-6-exo-(1-methyl-1-methoxyethyloxymethyl)-7-endo-tetrahydropyranyloxybicyclo[3.3.0]-oct-2-ene] (690 mg, Yield: 65%) as colorless oily products.

IR (neat): 1680, 1620 cm$^{-1}$.

NMR δ (CDCl$_3$): 9.77 (s, 1H), 6.72 (d, J=2Hz, 1H), 4.60 (bs, 1H), 3.00–4.20 (m, 6H), 3.20 (s, 3H), 1.34 (s, 6H).

Mass m/z (%): 338, 306, 253.

EXAMPLE 5

In the method as described in Reference examples 1 to 5 and Examples 1 and 2, the same procedures were carried out as in Reference examples 1 to 2 and Examples 1 and 2 except that 2-oxa-3-oxo-6-exo-(1-methyl-1-methoxyethyloxymethyl)-7-endo-tetrahydropyranyloxybicyclo[3.3.0]-octane (1.11 g, 3.88 mmol) was employed as the starting material to obtain 3-formyl-6-exo-(1-methyl-1-methoxyethyloxymethyl)-7-endo-tetrahydropyranyloxybicyclo[3.3.0]-oct-2-ene (590 mg, Overall yield: 45%) as colorles oily products.

IR (neat): 1680, 1620 cm$^{-1}$.

NMR δ (CDCl$_3$): 9.77 (s, 1H), 6.72 (d, J=2 Hz, 1H), 4.60 (bs, 1H), 3.00–4.20 (m, 6H), 3.20 (s, 3H), 1.34 (s, 6H).

Mass m/z (%): 338, 306, 253.

EXAMPLE 6

In the method as described in Reference examples 1 to 5 and Examples 1 and 2, the same procedures were carried out as in Reference examples 1 to 5 and Examples 1 and 2 except that 2-oxa-3-oxo-6-exo-t-butyldimethylsilyloxymethyl- 7-endo-(1-methyl-1-methoxyethyloxy)-bicyclo[3.3.0]-octane (1.21 g, 3.88 mmol) was employed as the starting material to obtain 3-formyl-6-exo-(t-butyldimethylsilyloxymethyl)-7-endo-(1-methyl-1-methoxyethyloxy)-bicyclo-[3.3.0]oct-2-ene (522 mg, Overall yield: 42%) as colorless oily products.

IR (neat): 1680, 1620 cm$^{-1}$.

NMR δ (CDCl$_3$): 9.78 (s, 1H), 6.71 (d, J=2 Hz, 1H), 3.50–4.20 (m, 3H), 3.20 (s, 3H), 3.00 (m, 1H), 1.34 (s, 6H), 0.90 (s, 9H).

Mass m/z (%): 368, 337, 311.

EXAMPLE 7

3-Carboxypropyltriphenylphosphonium bromide (5.58 g, 13 mmol) was suspended in THF (60 ml) under argon gas atmosphere. To the solution was added a solution of potassium t-butoxide (3.01 g, 26 mmol) in THF (50 ml) and the mixture was stirred at room temperature for 10 minutes. To the mixture was added dropwise a solution of l-3-formyl-6-exo-t-butyldimethylsilyloxymethyl-7-endotetrahydropyranyloxybicyclo[3.3.0]oct-2-ene (990 mg, 2.6 mmol) in THF (20 ml) and the miture was stirred at room temperature for 30 minutes. To the mixture was added a saturated aqueous ammonium chloride solution and THF was distilled out under reduced pressure. The resultant aqueous layer was adjusted to pH 5 to 4 with a 10% aqueous hydrochloric acid solution and extracted with ethyl acetate. The separated organic layer was dried over anhydrous magnesium sulfate and then solvents were distilled out. To the residue was added ether, insolubles were removed by filtration.

The residue obtained by evaporation of the solvent was purified through silica gel column chromatography to obtain 3-(4-carboxy-1-butenyl)-6-exo-t-butyldimethylsilyloxymethyl- 7-endo-tetrahydropyranyloxybicyclo[3.3.0]-oct-2-ene (1.05 g, Yield 90%). The ratio of (Z)-Isomer and (E)-Isomer was 2:1.

IR (neat): 3400, 1710, 840 cm$^{-1}$.

NMR δ (CDCl$_3$): 6.24 (d, J=16 Hz, ⅓H, trans), 5.95 (d, J=11 Hz, ⅔H, cis), 5.55 (bs, 1H), 5.30 (m, 1H), 4.60 (bs, 1H), 3.20–4.25 (m, 5H), 2.95 (m, 1H), 0.90 (s, 9H).

Mass m/z (%): 450 (M+), 309, 265, 85.

EXAMPLE 8

3-(4-Carboxy-1-butenyl)-6-exo-t-butyldimethylsilyloxymethyl-7-endo-tetrahydropyranyloxybicyclo[3.3.0]oct-2-ene (450 mg, 1 mmol) was dissolved in ether (5 ml) and to the mixtrue was added excess amount of diazomethane to obtain methyl ester thereof. Evaporation of the solvent in a draft chamber yielded l-3-(4-methoxycarbonyl-1-butenyl)-6-exo-t-butyldimethylsilyloxymethyl-7-endo-tetrahydropyranyloxybicyclo[3.3.0]oct-2-ene (464 mg, Yield: 100%) as scarcely colored oily products.

IR (neat): 2950, 2870, 1745, 840 cm$^{-1}$.

NMR δ (CDCl$_3$): 6.24 (d, J=16 Hz, ⅓H, trans), 5.98 (d, J=11 Hz, ⅔H, cis), 5.57 (bs, 1H), 5.30 (m, 1H), 4.60 (bs, 1H), 3.20–4.25 (m, 8H), 2.95 (1H), 0.90 (s, 9H).

Mass m/z (%): 464 (trace, M+), 323 (20), 231 (28), 159 (29), 157 (16), 117 (11), 85 (100), 75 (25), 73 (20), 67 (12), 57 (14), 43 (13), 41 (13).

$[\alpha]_D^{20} = -50°$ (c=1.36, MeOH).

EXAMPLE 9

3-(4-Carboxy-1-butenyl)-6-exo-t-butyldimethylsilyloxymethyl- 7-endo-tetrahydropyranyloxybicyclo[3.3.0]oct-2-ene (450 mg, 1 mmol) was dissolved in acetonitrile (2 ml) and to the solution were added DBU (304 mg, 2 mmol) and ethyl iodide (468 mg, 3 mmol) at room temperature and the mixture was further stirred for 3 hours. After the reaction was stopped with the addition of a saturated aqueous ammonium chloride solution, the mixture was extracted with ether. The separated ether layer was washed with a saturated saline solution and dried with anhydrous magnesium sulfate. After the mixture was distilled out the solvent, the residue was purified through silica gel column chromatography to obtain 3-(4-ethoxycarbonyl-1-butenyl)-6-exo-t-butyldimethylsilyloxymethyl-7-endo-tetrahydropyranylxxybicyclo[3.3.0]oct-2-ene (400 mg, Yield: 84%) as colorless oile products.

IR (neat): 2950, 2870, 1745, 840 cm$^{-1}$.

NMR δ (CDCl$_3$): 6.24 (d, J=16 Hz, ⅓H, trans), 5.98 (d, J=11 Hz, ⅔H, cis), 5.57 (bs, 1H), 5.30 (m, 1H), 4.60 (bs, 1H), 4.20 (q, J=7 Hz, 2H), 3.20–4.20 (m, 5H), 2.95 (m, 1H), 1.30 (t, J=7 Hz, 3H), 0.90 (s, 9H).

Mass m/z (%): 478 (M+), 433, 421, 393.

EXAMPLE 10

3-Carboxypropyltriphenylphosphonium bromide (5.58 g, 13 mmol) was suspended in THF (60 ml) under argon gas atmosphere. To the solution was added a solution of potassium t-butoxide (3.01 g, 26 mmol) in THF (50 ml) and the mixture was stirred at room temperature for 10 minutes. To the mixture was added dropwise a solution of [l-3-formyl-6-exo-t-butyldimethylsilyloxymethyl-7-endotetrahydropyranyloxybicyclo[3.3.0]oct-2-ene] (99 mg, 2.6 mmol) in THF (20 ml) and the miture was stirred at room temperature for 30 minutes. To the mixture was added a saturated aqueous ammonium chloride solution and THF was distilled out under reduced pressure. The resultant aqueous layer was adjusted to pH 5 to 4 with a 10% aqueous hydrochloric acid solution and extracted with ethyl acetate. The separated organic layer was dried over anhydrous magnesium sulfate and then solvents were distilled out. To the residue was added ether, insolubles were removed by filtration. To the filtrate was added an ether solution of diazomethane. After disappearance of spot of [3-(4-carboxy-1-butenyl)-6-exo-t-butyldimethylsilyloxymethyl-7-endo-tetrahydropyranyloxybicyclo[3.3.0]oct-2-ene] was confirmed by using thin layer chromatography, to the mixture was added a small amount of formic acid and the mixture was immediately washed with a saturated aqueous sodium hydrogencarbonate solution and a saturated saline solution. The resultant mixture was dried over anhydrous magnesium sulfate and distilled out the solvents. The residue was purified through silica gel column chromatography (ether:n-hexane=1:2) to obtain [l-3-(4-methoxycarbonyl-1-butenyl)-6-exo-t-butyldimethylsilyloxymethyl-7-endotetrahydropyranyloxybicyclo[3.3.0]oct-2-ene] (1.09 g, Yield: 90%). The ratio of (Z)-Isomer and (E)-Isomer was 2:1.

IR (neat): 2950, 2870, 1745, 840 cm$^{-1}$.

NMR δ (CDCl$_3$): 6.24 (d, J=16 Hz, ⅓H, trans), 5.98 (d, J=11 Hz, ⅔H, cis), 5.57 (bs, 1H), 5.30 (m, 1H), 4.60 (bs, 1H), 3.20–4.25 (m, 8H), 2.95 (1H), 0.90 (s, 9H).

Mass m/z (%): 464 (trace, M+), 323 (20), 231 (28), 159 (29), 157 (16), 117 (11), 85 (100), 75 (25), 73 (20), 67 (12), 57 (14), 43 (13), 41 (13).

$[\alpha]_D^{20} = -50°$ (c=1.36, MeOH).

EXAMPLE 11

Under argon gas atmosphere, 3-carboxypropyltriphenylphosphonium bromide (5.58 g, 13 mmol) was dissolved in DMSO (10 ml). To the solution was added a solution of sodium salt of DMSO in DMSO (26 mmol, 13 ml) at room temperature add the mixture was stirred at the same condition for 10 minutes. To the mixture was added dropwise a solution of -3-formyl-6-exo-t-butyldimethylsilyloxymethyl-7-endo-tetrahydropyranyloxybicyclo[3.3.0]oct-2-ene (990 mg, 2.6 mmol) dissolved in DMSO (5 ml) and the mixture was stirred at room temperature for 30 minutes. A saturated aqueous ammonium chloride solution was added thereto, and the separated aqueous layer was adjusted to pH 4 to 5 with a 10% aqueous hydrochloric acid solution and then extracted with ethyl acetate. The extract was washed with a saturated saline solution and dried with anhydrous magnesium sulfate. After evaporation of the solvent, the residue was treated with diazomethane and purified through silica gel column chromatography (ether:n-hexane=1:2) to obtain l-3-(4-methoxycarbonyl-1-butenyl)-6-exo-t-butyldimethylsilyloxymethyl-7-endo-tetrahydropyranyloxybicyclo[3.3.0]oct-2-ene (483 mg, Yield: 40%) as scarcely colored oily products. The ratio of (Z)-Isomer and (E)-Isomer was about 2:1 and the various spectrum data thereof were agreed with those of substance obtained in Example 8.

EXAMPLE 12

Under argon gas atmosphere, 3-carboxypropyltriphenylphosphosium brimide (5.58 g, 13 mmol) was suspended in a mixed solution of benzene (27 ml) and DMSO (0.4 ml). To the suspension was added a solution of t-amyloxy sodium dissolved in benzene (26 mmol, 16.7 ml) at atmospheric temperature of 75° C., and the mixture was stirred at the same condition for 10 minutes. To the thus obtained mixture was added a solution of 1-3-formyl-6-exo-t-butyldimethylsilyloxymethyl-7-endo-tetrahydropyranyloxybicyclo[3.3.0]oct-2-ene (990 mg, 2.6 mmol) dissolved in benzene (5 ml), and the mixture was further stirred at 75° C. for 10 minutes. A saturated aqueous ammonium chloride solution was added thereto, and the separated aqueous layer was adjusted to pH 4 to 5 with a 10% aqueous hydrochloric acid solution and then extracted with ethyl acetate. The extract was washed with a saturated saline solution and dried with anhydrous magnesium sulfate. After evaporation of the solvent, the residue was treated with diazomethane and purified through silica gel column chromatography (ether:n-hexane=1:2) to obtain l-3-(4-methoxycarbonyl-1-butenyl)-6-exo-t-butyldimethylsilyloxymethyl-7-endo-tetrahydropyranyloxybicyclo[3.3.0]oct-2-ene (613 mg, Yiled: 56%) as scarcely colored oily products. The ratio of (Z)-Isomer and (E)-Isomer was about 1:1 and the various spectrum data thereof were about the same with those of substance obtained in Example 8.

EXAMPLE 13

Under argon gas atmosphere, 3-carboxypropyltriphenylphosphonium bromide (5.58 g, 13 mmol) was suspended in THF (60 ml). A THF (50 ml) solution of potassium t-butoxide (3.01 g, 26 mmol) was added thereto and the mixture was stirred at room temperature for 10 minutes. To the thus prepared mixture was added dropwise a THF (20 ml) solution of 3-formyl-6-exo-(1-methyl-1-methoxyethyloxymethyl)-7-endo-tetrahydropyranyloxybicyclo[3.3.0]oct-2-ene (879 mg, 2.6 mmol), and the mixture was stirred at room temperature for 30 minutes. To the mixture was added a saturated aqueous ammonium chloride solution, and THF in the mixture was distilled off under reduced pressure. The resultant aqueous layer was adjusted to pH with a 10% aqueous hydrochloric acid solution and extracted with ethyl acetate. The separated organic layer was dried with anhydrous magnesium sulfate and then the solvent was distilled off. To the residue was added ether and insolubles were removed by filtration. After evaporation of the solvent, the redisue was purified through silica gel column chromatography to obtain 3-(4-carboxy-1-butenyl)-6-exo-(1-methyl-1-methoxyethyloxymethyl)-7-endo-tetrahydropyranyloxybicyclo[3.3.0]oct-2-ene (965 mg, Yield: 91%). The ratio of (Z)-Isomer and (E)-Isomer was 2:1.

IR (neat): 3400, 1710, 840 cm$^{-1}$.

NMR δ (CDCl$_3$): 6.23 (d, J=16 Hz, ⅓H, trans), 5.95 (d, J=11 Hz, 2/3H, cis), 5.55 (bs, 1H), 5.30 (m, 1H), 4.60 (bs, 1H), 3.30–4.20 (m, 5H), 3.20 (s, 3H), 2.95 (m, 1H), 1.34 (s, 6H).

Mass m/z (%): 408 (M+), 377, 364, 323.

Then, 3-(4-carboxy-1-butenyl)-6-exo-(1-methyl-1-methoxyethyloxymethyl)-7-endo-tetrahydropyranyloxybicyclo[3.3.0]oct-2-ene was subjected to treatment in ether with excess amount of diazomethane to obtain l-3-(4-methoxycarbonyl-1-butenyl)-6-exo-(1-methyl-1-methoxyethyloxymethyl)-7-endo-tetrahydropyranyloxybicyclo[3.3.0]oct-2-ene quantitatively as colorless oily products.

IR (neat): 2950, 1742 cm$^{-1}$.

NMR δ (CDCl$_3$): 6.22 (d, J=16 Hz, ⅓H, trans), 5.95 (d, J=11Hz, ⅔H, cis), 5.58 (bs, 1H), 5.30 (m, 1H), 4.62 (m, 1H), 3.67 (s, 3H), 3.25–4.10 (m, 5H), 3.20 (s, 3H), 3.00 (m, 1H), 1.34 (s, 6H).

Mass m/z (%): 390, 350, 338, 332, 306, 248, 230, 204, 191, 143, 131, 117, 91, 86, 85, 79, 73, 67.

$[\alpha]_D^{20} = -43.5°$ (c=0.718, MeOH).

EXAMPLE 14

Under argon gas atmosphere, 3-carboxypropyltriphenylphosphoniumbromide (5.58 g, 13 mmol) was suspended in THF (60 ml). To the suspension was added a solution of potassium t-butoxide (3.01 g, 26 mmol) in THF (50 ml) and the mixture was stirred at room temperature for 10 minutes. To the mixture was added dropwise a solution of 3-formyl-6-exo-t-butyldimethylsilyloxymethyl-7-endo-(1-methyl-1-methoxyethyloxy) -bicyclo[3.3.0]oct-2-ene (957 mg, 2.6 mmol) dissolved in THF (20 ml) and the mixture was stirred at room temperature for 30 minutes. A saturated aqueous ammonium chloride solution was added thereto, and THF in the mixture was distilled out under reduced pressure. The resultant aqueous layer was adjusted to pH 4 to 5 with a 10% aqueous hydrochloric acid solution and then extracted with ethyl acetate. After the separated organic layer was dried with anhydrous magnesium sulfate, the solvent was distilled out. To the residue was added ether and insolubles were removed by filtration. Evaporation of the solvent, followed by purification through silica gel column chromatography (ether) to obtain 3-(4-carboxy-1-butenyl)-6-exo-t-butyldimethylsilyloxymethyl-7-endo-(1-methyl-1-methoxyethyloxy)-bicyclo[3.3.0]oct-2-ene (1.00 g, Yield: 88%). The ratio of (Z)-Isomer and (E)-Isomer was 2:1.

IR (neat): 3400, 1710 cm$^{-1}$.

NMR δ (CDCl$_3$): 6.24 (d, J=16 Hz, ⅓H, trans), 5.95 (d, J=11 Hz, ⅔H, cis), 5.54 (bs, 1H), 5.30 (m, 1H), 3.30–4.20 (m, 3H), 3.20 (s, 3H), 2.95 (m, 1H), 1.34 (s, 6H), 0.90 (s, 9H).

Mass m/z (%): 438 (M+), 407, 394, 381.

3-(4-Carboxy-1-butenyl)-6-exo-t-butyldimethylsilyloxymethyl-7-endo-(1-methyl-1-methoxyethyloxy)-bicyclo[3.3.0]-oct-2-ene was treated with excess amount of diazomethane in ether solution to obtain l-3-(4-methyoxycarbonyl-1-butenyl)-6-exo-t-butyldimethylsilyloxymethyl-7-endo-(1-methyl-1-methoxyethyloxy)-bicyclo[3.3.0]oct-2-ene quantitatively as colorless oily products.

IR (neat): 2960, 1745, 838 cm$^{-1}$.

NMR δ (CDCl$_3$): 6.24 (d, J=15 Hz, ½H, trans, 5.96 (d, J=11Hz, ⅜H, cis), 5.60 (bs, 1H), 5.30 (m, 1H), 3.68 (s, 3H), 3.30–4.30 (m, 3H), 3.20 (s, 3H), 3.00 (m, 1H), 1.33 (s, 6H), 0.90 (s, 9H), 0.05 (s, 6H).

Mass m/z (%): 420, 380, 363, 323, 231, 171, 157, 115, 89, 75, 73.

$[\alpha]_D^{20} = -21°$ (c=0.592, MeOH).

EXAMPLE 15

[l-3-(4-Methoxycarbonyl-1-butenyl)-6-exo-t-butyldimethylsilyloxymethyl-7-endo-tetrahydropyranyloxybicyclo[3.3.0]-oct-2-ene] (547 mg, 1.18 mmol) was dissolved in methanol (10 ml). To the solution was added a 10% palladium/carbon (150 mg), the mixture was stirred at room temperature for 1 hour and 10 minutes under hydrogen gas atmosphere. The catalyst was removed by filtration and solvents in the filtrate were distilled out. The residue was purified through silica gel column chromatography (ether: n-hexane=1:5) to obtain [l-3-(4-methoxycarbonylbutyl)-6-exo-t-butyldimethylsilyloxymethyl-7-endo-tetrahydropyranyloxybicyclo[3.3.0]oct-2-ene] (509 mg, Yield: 93%).

IR (neat): 2950, 2880, 1745, 840 cm$^{-1}$.

NMR δ (CDCl$_3$): 5.25 (d, J=1 Hz, 1H), 4.60 (bs, 1H), 3.65 (s, 3H), 2.90 (m, 1H), 0.90 (s, 9H).

Mass m/z (%): 325 (8), 233 (12), 159 (28), 85 (100), 75 (17), 73 (13).

$[\alpha]_D^{20} = -12°$ (c=1.68, MeOH).

EXAMPLE 16

In methanol (10 ml) was dissolved [3-(4-methoxycarbonyl-1E-butenyl)-6-exo-t-butyldimethylsilyloxymethyl-7-endo-t-butyldimethylsilyloxy-bicyclo[3.3.0]oct-2-ene] (583 mg, 1.18 mmol). To the solution was added a 10% palladium/carbon (150 mg) and the mixture was stirred under hydrogen atmosphere (1 atm.) at room temperature for 1 hour and 10 minutes. After the catalyst was removed by filtration, the solvent in the filtrate was distilled off. The residue was purified through silica gel column chromatography to obtain [l-3-(4-methoxycarbonylbutyl)-6-exo-t-butyldimethylsilyloxymethyl-7-endo-t-butyldimethyl silyloxybicyclo[3.3.0]oct-2-ene] (380 mg, Yield: 65%).

IR (neat): 1745 cm$^{-1}$.

NMR δ (CDCl$_3$): 5.30 (1H), 3.85 (1H), 3.65 (s, 3H), 3.60 (2H), 2.90 (1H), 0.90 (s, 9H), 0.85 (s, 9H), 0.05 (12H).

Mass m/z (%): 439 (M$^+$−57, 25), 243 (11), 233 (64), 207 (53), 201 (42), 189 (11), 183 (21), 175 (19), 173 (14), 159 (14), 157 (14), 149 (17), 148 (12), 147 (67), 73 (100).

Mili-MS: 439.2697 (M$^+$-t-Bu); M$^+$-t-Bu=C$_{23}$H$_{43}$O$_4$Si$_2$=439.2697.

EXAMPLE 17

In the method as described in Example 15, the same procedures were carried out as in Example 15 except that 1-3-(4-methoxycarbonyl-1-butenyl)-6-exo-(1-methyl-1-methoxyethyloxymethyl)-7-endo-tetrahydropyranyloxybicyclo[3.3.0]oct-2-ene] (498 mg, 1.18 mmol) was employed as the starting material to obtain [3-(4-methoxycarbonylbutyl)-6-exo-(1-methyl-1-methoxyethyloxymethyl)-7-endo-tetrahydropyranyloxybicyclo[3.3.0]oct-2-ene] (425 mg, Yield: 85%).

IR (neat): 2950, 2880, 1742, 840 cm$^{-1}$.

NMR δ (CDCl$_3$): 5.23 (d, J=1Hz, 1H), 4.60 (bs, 1H), 3.65 (s, 3H), 3.40–4.10 (m, 5H), 3.20 (s, 3H), 2.90 (m, 1H), 1.34 (s, 6H).

Mass m/z (%): 424 (M$^+$), 393, 392, 339.

EXAMPLE 18

[l-3-(4-Methoxycarbonylbutyl)-6-exo-t-butyldimethylsilyloxymethyl-7-endo-tetrahydropyranyloxybicyclo[3.3.0]-oct-2-ene] (585 mg, 1.26 mmol) was dissolved in THF (5 ml). To the solution was added tetra-n-butylammonium fluoride (1M THF solution 2.5 ml, 2.5 mmol), the mixture was stirred at room temperature for 3 hours. To the mixture was added a saturated saline solution and THF was distilled out therefrom under reduced pressure. After the resultant aqueous layer was extracted with ether, the separated ether layer was dried over anhydrous magnesium sulfate and then solvents were distilled out. The residue was purified through silica gel column chromatography to obtain [l-3-(4-methoxycarbonylbutyl)-6-exo-hydroxymethyl-7-endo-tetrahydropyranyloxybicyclo[3.3.0]-oct-2-ene] (425 mg, Yield: 95.2%).

IR (neat): 3480, 2950, 2880, 1740 cm$^{-1}$.

NMR δ (CDCl$_3$): 5.25 (d, J=1Hz, 1H), 4.60 (m, 1H), 3.66 (s, 3H), 3.00 (m, 1H).

Mass m/z (%): 352 (trace, M$^+$), 268 (3), 85 (100), 67 (11), 57 (10), 41 (11).

$[\alpha]_D^{20} = -19°$ (c=2.09, MeOH).

EXAMPLE 19

[l-3-(4-methoxycarbonylbutyl)-6-exo-t-butyldimethylsilyloxymethyl-7-endo-t-butyldimethylsilyloxybicyclo[3.3.0]-oct-2-ene] (4.8 mg, 0.01 mmol) was dissolved in hydrated ethanol (ethanol: H$_2$O=75:1) (0.15 ml), and pyridinium p-toluenesulfonate (1 mg, 0.004 mmol) was added thereto and the mixture was stirred at 25° C. for 16 hours. After the mixture was diluted with ether, the resultant mixture was washed successively with a 1% aqueous HCl solution, a saturated aqueous NaHCO$_3$ solution and a saturated saline solution, and dried with anhydrous magensium sulfate. After evaporation of the solvent, the residue was purified through silica gel column chromatography. As a result, 2.3 mg (Yield: 60%) of [3-(4-methoxycarbonylbutyl)-6-exo-hydroxymethyl-7-endo-t-butyldimethylsilyloxybicyclo[3.3.0]oct-2-ene] was obtained as substantially colorless oily products.

IR (neat): 3480, 1740 cm$^{-1}$.

NMR δ (ppm): 5.30 (1H), 3.85 (1H), 3.65 (s, 3H), 3.60 (2H), 2.90 (1H).

EXAMPLE 20

[3-(4-Methoxycarbonylbutyl)-6-exo-(1-methyl-1-methoxyethyloxymethyl)-7-endo-tetrahydropyranyloxybicyclo-[3.3.0]oct-2-ene] (424 mg, 1 mmol) was dissolved in THF (11 ml) and the solution was added under ice-cooling a 0.5N HCl (5.5 ml) and stirred at the same temperature for 10 minutes. Ethyl acetate (109 ml) was added thereto and the separated organic layer was washed with water and then a saturated saline solution and dried wth anhydrous magnesium sulfate. Evaporation of the solvent, followed by purification through silica gel column chromatography to obtain [l-3-(4-methoxycarbonylbutyl)-6-exo-hydroxymethyl-7-endo-tetrahydropyranyloxybicyclo[3.3.0]oct-2-ene] (334 mg, Yield: 95%) as colorless oily product.

Various spectrum data of the thus obtained compound were absolutely agreed with those of the substance obtained in Example 18.

EXAMPLE 21

Collins reagent (CrO$_3$.2Py, 660 mg, 2.56 mmol) and Celite (660 mg) were suspended in methylene chloride under argon gas atmosphere. A solution of [l-3-(4-methoxycarbonylbutyl)-6-exo-hydroxymethyl-7-endo-tetrahydropyranyloxybicyclo[3.3.0]octo-2-ene] (50 mg, 0.142 mmol) dissolved in methylene chloride (2.5 ml) was added to the suspension and stirred at 0° C. for 30 minutes. To the mixutre was added 1.32 g of sodium hydrogensulfate monohydrate and the mixture was further stirred at 0° C. for 10 minutes. The reaction mixture was filtrated by using anhydrous magnesium sulfate as a filter aid and the filter aid was washed with methylene chloride. The filtrates were combined and evaporated the solvent to obtain [3-(4-methoxycarbonylbutyl)-6-exo-formyl-7-endo-tetrahydropyranyloxybicyclo[3.3.0]oct-2-ene] (48 mg, Yield: 96%).

On the other hand, sodium hydride (60% of oily mixture, 11 mg, 0.28 mmol) was washed with pentane under argon gas atmosphere and suspended in 3 ml of DME (dimethoxyethane). To the suspension was added a solution of dimethyl(2-oxoheptyl)phosphonate (64 mg, 0.29 mmol) dissolved in DME (3 ml) and the mixture was stirred at room temperature for 25 minutes. To the mixture was added a solution of [3-(4-methoxycarbonylbutyl)-6-exo-formyl-7-endo-tetrahydropyranyloxybicyclo[3.3.0]oct-2-ene] (48 mg) dissolved in DME (3 ml), the mixture was stirred at room temperature for an hour and then a saturated aqueous ammonium chloride solution was added thereto. Evaporation of DME under reduced pressure followed by extraction with ethyl ether. The separated ether layer was washed with a saturated saline solution. After the mixture was dried over anhydrous magnesium sulfate, the residue obtained by evaporation of the solvent was purified through silica gel column chromatography (ether:n-hexane=2:5) to obtain [3-(4-methoxycarbonylbutyl)-6-exo-(3-oxo-trans-1-octenyl)-7-endo-tetrahydropyranyloxybicyclo[3.3.0]oct-2-ene] (35 mg, Yield: 57%).

IR (neat): 2950, 2880, 1742, 1698, 1672, 1628 cm$^{-1}$.

NMR δ (CDCl$_3$): 6.80 (m, 1H), 6.17 (dxd, J=16 Hz, J=4 Hz, 1H), 5.30 (d, J=1 Hz, 1H), 4.65 and 4.55 (each bs, total 1H), 3.68 (s, 3H), 3.00 (m, 1H).

Mass m/z (%): 362 (10), 318 (13), 85 (100), 67 (16), 57 (18), 55 (13), 43 (20), 41 (20).

EXAMPLES 22 to 25

Various kinds of the (3-oxo-1-alkenyl)-cis-bicyclo[3.3.0]octene derivatives as shown in Table 1 were synthesized by the reaction with each of dimethyl-(2-oxoalkyl)phosphonate in the same manner as in Example 21. The results of the synthesis are shown in Table 1 and the spectrum data thereof are shown in Table 2 below.

TABLE 1

| Example No. | Starting phosphonate | Reaction product | Yield (%) |
|---|---|---|---|
| 22 | (MeO)$_2$P(O)—CH$_2$C(O)—CH(CH$_3$)—(CH$_2$)$_3$CH$_3$ | (branched alkenyl group) | 65 |
| 23 | (MeO)$_2$P(O)—CH$_2$C(O)—C(H)(cyclobutyl-CH$_2$CH$_2$/CH$_2$CH$_2$) | (cyclopentyl group) | 52 |
| 24 | (MeO)$_2$PCH$_2$CCH$_2$CH(CH$_3$)(CH$_2$)$_2$C(H)=C(CH$_3$)$_2$ | (branched alkenyl with terminal =C(CH$_3$)$_2$) | 76 |
| 25 | (MeO)$_2$PCH$_2$C(O)—C(CH$_3$)$_2$—(CH$_2$)$_3$CH$_3$ | (gem-dimethyl alkyl group) | 45 |

TABLE 2

| Example No. | Characteristic IR spectrum (cm$^{-1}$) ν$_{C=O}$ | | NMR spectrum δ ppm olefin proton | |
|---|---|---|---|---|
| | ester | keton | ring | side chain |
| 22 | 1742 | 1698, 1672, 1628 | 5.28 | 6.80, 6.20 |
| 23 | 1742 | 1698, 1672, 1628 | 5.28 | 6.80, 6.20 |
| 24 | 1742 | 1698, 1672, 1628 | 5.28 | 6.75, 6.20 5.10 |
| 25 | 1742 | 1692, 1622 | 5.28 | 6.80, 6.55 |

EXAMPLE 26

[3-(4-Methoxycarbonylbutyl)-6-exo-hydroxymethyl-7-endo-t-butyldimethylsilyloxybicyclo[3.3.0]oct-2-ene] (118 mg, 0.31 mmol) was dissolved in a mixed solvent of DMSO (3.5 ml) and triethylamine (0.26 ml), and a DMSO solution (2.5 ml) of SO$_3$.py (148 mg, 0.93 mmol) was added thereto at room temperature while stirring. After the mixture was stirred at the same condition for 1 hour and 20 minutes, it was poured into ice-cold water and then extracted with ether. The separated ether layer was washed with water and a saturated saline solution, and dried with anhydrous magensium sulfate. About 110 mg of an aldehyde derivative was obtained after evaporation of the solvent and it was employed to the next reaction without purification.

Sodium hydride (60% oily substance, 17 mg, 0.43 mmol) was washed with pentane under argon gas atmosphere, and suspended in 3 ml of THF. To the suspension was added a 10.5 ml of THF solution of dimethyl(2-oxoheptyl)phosphonate (103 mg, 0.47 mmol) and the mixture was stirred at room temperature for 30 minutes.

To the thus prepared anion solution was added the previously prepared THF solution (1.5 ml) of the aldehyde derivative and the mixture was stirred at the same conditions for 40 minutes, then the reaction was stopped by adding 0.11 ml of acetic acid. After the resultant mixture was diluted with ether, the mixture was washed with a saturated aqueous NaHCO$_3$ solution and dried with anhydrous magensium sulfate. Evaporation of the solvent, followed by purification through silica gel column chromatography to obtain [3-(4-methoxycarbonyl-butyl)-6-exo-(3-oxo-trans-1-octenyl)-7-endo-t-butyldimethylsilyloxybicyclo[3.3.0]oct-2-ene] (107 mg, Yield: 73%) as substantially colorless oily products.

IR (neat): 1742, 1698, 1672, 1628 cm$^{-1}$.

NMR δ (ppm): 6.80 (dd, 1H), 6.17 (dd, 1H), 5.30 (d, J=1 Hz, 1H), 4.00 (m, 1H), 3.68 (s, 3H), 3.00 (m, 1H).

EXAMPLE 27

[3-(4-Methoxycarbonylbutyl)-6-exo-(3-oxo-trans-1-octenyl)-7-endo-t-butyldimethylsilyloxybicyclo[3.3.0]oct-2-ene] (93 mg, 0.20 mmol) was dissolved in a 65% hydrated acetic acid (1.7 ml) and tetrahydrofuran (0.17 ml) and the solution was stirred at 50° C. for an hour. The resultant mixture was poured into a saturated aqueous NaHCO$_3$ solution and extracted with ethyl acetate. The separated organic layer was washed with water and a saturated saline solution, and dried with anhydrous magensium sulfate. Evaporation of the solvent, followed by purification through silica gel column chromatography to obtain 72 mg (Yield: 99%) of [3-(4-methoxycarbonylbutyl)-6-exo-(3-oxo-trans-1-octenyl)-7-endo-hydroxybicyclo[3.3.0]oct-2-ene] as substantially colorless oily products.

IR (neat): 3470, 2950, 1740, 1699, 1675, 1625 cm$^{-1}$.

NMR δ (ppm): 6.55 (dd, J=16 Hz, 8 Hz, 1H), 6.16 (d, J=16 Hz, 1H), 5.30 (broad s, 1H), 3.90 (qd, J=8 Hz, 2 Hz, 1H), 3.68 (s, 3H), 3.00 (m, 1H), 1.80–2.80 (m, 12H), 1.10–2.80 (m, 10H), 0.90 (t, J=6 Hz, 3H).

$[α]_D^{20}$ = +105° (c=1.488, MeOH).

REFERENCE EXAMPLE 7

[3-(4-Methoxycarbonylbutyl)-6-exo-(3-oxo-trans-1-octenyl)-7-endo-tetrahydropyranyloxybicyclo[3.3.0]oct-2-ene] (32 mg, 0.072 mmol) was dissolved in methanol (5 ml). The solution was cooled to −20° C. and excess amount of sodium borohydride was added thereto. After the mixture was stirred at −20° C. for 20 minutes, excess amount of acetone was added thereto. After the temperature of the mixture was returned to room temperature, to the mixture was added a saturated aqueous ammonium chloride solution and methanol and acetone were distilled by evaporation under reduced pressure. The resultant aqueous layer was extracted with ether and then dried with anhydrous magnesium chloride to obtain [3-(4-methoxycarbonylbutyl)-6-exo-(3-hydroxy-trans-1-octenyl)-7-endo-tetrahydropyranyloxybicyclo[3.3.0]oct-2-ene (32 mg, Yield: 100%).

IR (neat): 3470, 3230, 2950, 2880, 1742 cm$^{-1}$.

NMR δ (CDCl$_3$): 5.57 (m, 2H), 5.28 (d, J=1 Hz, 1H), 4.63 (bs, 1H), 3.65 (s, 3H), 2.95 (m, 1H).

Mass m/z (%): 430 (1, M$^+$—H$_2$O), 302 (15), 85 (100), 67 (13), 57 (16), 55 (11), 43 (17), 41 (18).

REFERENCE EXAMPLES 8 to 11

Various kinds of 3-oxo-1-alkenyl-cis-bicyclo[3.3.0]octene derivatives were reduced in the same manner as in Reference Example 7. The obtained results and spectrum data thereof were shown in Table 3 below.

TABLE 3

| Reference example No. | R | Yield (%) | Characteristics IR spectrum (cm$^{-1}$) | | NMR spectrum (δ ppm) olefin proton | |
|---|---|---|---|---|---|---|
| | | | $ν_{OH}$ | $ν_{C=O}$ | ring | side chain |
| 8 | (n-pentyl chain) | 100 | 3500 | 1742 | 5.30 | 5.60 |
| 9 | (cyclopentyl) | 100 | 3480 | 1740 | 5.28 | 5.62 |
| 10 | (methyl-branched alkenyl) | 100 | 3480, 3230 | 1742 | 5.30 | 5.60, 5.13 |
| 11 | (dimethyl-branched alkyl) | 100 | 3500, 3220 | 1742 | 5.30 | 5.62 |

REFERENCE EXAMPLE 12

[3-(4-Methoxycarbonylbutyl)-6-exo-(3-oxo-trans-1-octenyl)-7-endo-hydroxybicyclo[3.3.0]oct-2-ene] (36 mg, 0.1 mmol) was dissolved in anhydrous toluene (1 ml).

Prior to the above procedure, diisobutylaluminum hydride in toluene solution (331 mg, 1.5 mmol) was added to 2,6-di- t-butyl-4-methylphenol (331 mg, 1.5 mmol) in toluene (2.6 ml) solution under ice-cooling, and the solution was stirred at the same condition for an hour. To the thus prepared solution was added the previously prepared toluene solution containing a starting material at −78 ° C. Temperature of the mixture was elevated to −10° C. over 2.5 hours and the mixture was stirred at the same temperature for 3 hours. The reaction was stopped by adding 0.34 ml of water and stirring was further continuted at room temperature for an hour. After insolubels were removed by precipitation, solvents were distilled out by evaporation. The residue was purified through silica gel column chromatography to obtain [3-(4-methoxycarbonylbutyl)-6-exo-(3α-hydroxy-trans-1-octenyl)-7-endo-hydroxybicyclo[3.3.0]oct-2-ene] (20.6 mg, Yield: 57%) and [3-(4-methoxycarbonylbutyl)-6-exo-(3β-hydroxy-trans-1-octenyl)-7-endo-hydroxybicyclco[3.3.0]-oct-2-ene] (8.3 mg, Yield: 23%) as oily products, respectively. The spectrum data of α-epimer are shown in the following. The spectrum data of β-epimer are the same to those of α-epimer.

IR (neat): 3400, 2970, 2930, 2870, 1742 cm⁻¹.

NMR δ (ppm): 5.60 (m, 2H), 5.33 (bs, 1H), 4.12 (m, 1H), 3.80 (m, 1H), 3.69 (s, 3H), 3.00 (m, 1H).

mer based on the 15-positon hydroxy group in the resultant mixture was separated by using silica gel column chromatography. The obtained results and spectrum data thereof are shown in Table 4 below. In each cases, an isomer having higher polarity named α-epimer and an isomer having lower polarity of β-epimer.

TABLE 4

| Reference example No. | R | Yield (%) | | Characteristic IR spectrum (cm⁻¹) | | NMR spectrum (δ ppm) olefin proton | |
|---|---|---|---|---|---|---|---|
| | | α-epimer | β-epimer | $\nu_{OH}$ | $\nu_{C=O}$ | ring | side chain |
| 14 | | 46 | 31 | 3400 | 1740 | 5.33 | 5.61 |
| 15 | | 39 | 20 | 3400 | 1740 | 5.32 | 5.61 |
| 16 | | 41 | 16 | 3400 | 1741 | 5.33 | 5.62 |
| 17 | | 45 | 22 | 3420 | 1742 | 5.34 | 5.65 |

*All the spectrum data shown are of α-epimer. The spectrum data of β-epimer are the same.

Mass m/z (%): 346 (25, M⁺—H₂O), 328 (18), 315 (9), 302 (71), 275 (15), 247 (11), 232 (32), 199 (17), 193 (19), 180 (30), 179 (27).

REFERENCE EXAMPLE 13

[3-(4-Methoxycarbonylbutyl)-6-exo-(3-hydroxy-trans-1-octenyl)-7-endo-tetrahydropyranyloxybicyclo[3.3.0]oct-2-ene] (32 mg, 0.072 mmol) was dissolved in a mixed solution of acetic acid:water:THF (0.5 ml) (3:1:1, volume ratio) and the solution was stirred at 45° to 50° C. for 5 hours. After dilution with ether, the mixture was neutralized with a saturated aqueous sodium hydrogen-carbonate solution. After the separated ether layer was washed with a saturated saline solution, dired with anhydrous magnesium sulfate. Evaporation of the solvent followed by purification through silica gel column chromatography (ether:n-hexane=5:1 to ether:methanol=40:1) to obtain [3-(4-methoxycarbonylbutyl)-6-exo-(3α-hydroxy-trans-1-octenyl)-7-endo-hydroxybicyclo[3.3.0]-oct-2-ene] (13 mg, Yield: 48%) as a higher polarity fraction and [3-(4-methoxycarbonylbutyl)-6-exo-(3β-hydroxy-trans-1-octenyl)-7-endo-hydroxybicyclo[3.3.0]-oct-2-ene] (7 mg, Yield: 26%) as a lower polarity fraction. The spectrum data of an α-epimer are shown in the following. The spectrum data of a β-epimer are the same as those of the α-epimer.

IR (neat): 3400, 2970, 2930, 2870, 1742 cm⁻¹.

NMR δ (CDCl₃): 5.60 (m, 2H), 5.33 (bs, 1H), 4.12 (m, 1H), 3.69 (s, 3H), 3.00 (m, 1H).

Mass m/z (%): 346 (25, M⁺—H₂O), 328 (18), 315 (9), 302 (71), 275 (15), 247 (11), 232 (32), 199 (17), 193 (19), 180 (30), 179 (27).

REFERENCE EXAMPLES 14 to 17

By using various kinds of [3-(4-methoxycarbonylbutyl)-6-exo-(3-hydroxy-trans-1-alkenyl)-7-endo-tetrahydropyranyloxybicyclo[3.3.0]oct-2-ene], elimination reaction of each THP group was carried out in the same manner as in Reference Example 13 and then each iso-

REFERENCE EXAMPLE 18

3-(4-Methoxycarbonylbutyl)-6-exo-(3α-hydroxy-trans-1-octenyl)-7-endo-hydroxybicyclo[3.3.0]oct-2-ene] (10 mg, 0.027 mmol) was dissolved in methanol (0.3 ml). To the solution was added a 10% aqueous sodium hydroxide solution (0.2 ml) at 0° C. After stirring for 9 hours at 60° C., the mixture was neutralized with a 10% hydrochloric acid solution while cooling. Evaporation of methanol under reduced pressure, followed by adjustement to pH 3 to 4 and then the mixture was extracted with ethyl acetate. The extract was dried with anhydrous magnesium sulfate and distilled the solvent to obtain [9(0)-methano-Δ⁶⁽⁹ᵅ⁾-PGI₁] (10 mg, Yield: 100%).

IR (neat): 3350, 2910, 2850, 1700, 1450, 1250 cm⁻¹.

NMR δ (CDCl₃): 5.60 (m, 2H), 5.33 (bs, 1H), 4.11 (m, 1H), 3.80 (m, 1H), 3.00 (m, 1H), 0.90 (t, J=6 Hz, 3H).

Mass (CI, NH₃) m/z (%): 368 (25, M⁺+NH₄).

Melting point: 73° to 79° C.

[α]$_D^{25}$ = +16° (c=0.25, MeOH).

15β-Epimer was hydrolyzed in the same manner as mentioned above to obtain 15β isomer of 9(0)-methano-Δ⁶⁽⁹ᵅ⁾-PGI₁. The spectrum data (IR, NMR, Mass) thereof agreed with that of 9(0)-methano-Δ⁶⁽⁹ᵅ⁾-PGI₁.

REFERENCE EXAMPLES 19 to 22

In the same manner as in Reference Example 18, various kinds of [3-(4-methoxycarbonylbutyl)-6-exo-(3α-hydroxy-trans-1-alkenyl)-7-endo-hydroxybicyclo[3.3.0]oct-2-ene] were hydrolyzed to obtain various kinds of [9(0)-methano-Δ⁶⁽⁹ᵅ⁾-PGI₁ derivatives]. The obtained results and spectrum data thereof are shown in Table 5 below.

In the same manner as above, 15β-epimer was also hydrolyzed to obtain 15α-isomer of 9(0)-methano-Δ⁶⁽⁹ᵅ⁾-PGI₁ derivatives. The spectrum data (IR, NMR, Mass) thereof agreed with that of 9(0)-methano-Δ⁶⁽⁹ᵅ⁾-PGI₁ derivatives.

TABLE 5

| Reference example No. | R | Yield (%) | Characteristic IR spectrum (cm$^{-1}$) $\nu_{OH}$ | $\nu_{C=O}$ | NMR spectrum (δ ppm) olefin proton ring | side chain |
| --- | --- | --- | --- | --- | --- | --- |
| 19 | (sec-butyl/pentyl chain) | 97 | 3400 | 1710 | 5.58 | 5.33 |
| 20 | (cyclopentyl) | 73 | 3400 | 1710 | 5.60 | 5.32 |
| 21 | (methylheptenyl) | 95 | 3400 | 1710 | 5.60 | 5.33 |
| 22 | (dimethylpentyl) | 100 | 3400 | 1710 | 5.62 | 5.32 |

REFERENCE EXAMPLE 23

1-3-(4-Methoxycarbonyl-1-butenyl)-6-exo-t-butyldimethylsilyloxymethyl-7-endo-tetrahydropyranyloxybiycl[3.3.0]oct-2-ene (mixture of cis:trans=2:1; 116 mg, 0.25 mmol) and methylbenzoatetricarbonylchromium (14 mg, 0.05 mmol) were dissolved in acetone (10 ml) and a cycle of cooling-diminished pressure-dissolution were repeated to degas. The resultant mixture was transffered into 100 ml of autoclave anLbN 70 kg/cm$^2$ of hydrogen gas was charged therein. After the reaction at 120° C. for 15 hours, evaporation of the solvent followed by purification through silica gel column chromatography (ether:n-hexane=1:5) to obtain 3E-(4-methoxycarbonylbutylidene)-6-exo-t-butyldimethylsilyloxymethyl-7-endo-tetrahydropyranyloxybicyclo[3.3.0]octane (111 mg, Yield: 95%). The obtained material did not contain at all a Z-Isomer due to a double bond from the result of analysis by using gas chromatography.

IR (neat): 2970, 2880, 1747, 840 cm$^{-1}$.

NMR δ (CDCl$_3$): 5.23 (t, J=7 Hz, 1H), 4.66 (m, 1H), 3.70 (s, 3H), 3.30–4.10 (m, 5H), 0.90 (s, 9H), 0.05 (s, 6H).

Mass m/z (%): 466 (M+, trace), 325 (37), 233 (70), 201 (44), 159 (100), 85 (100), 75 (75), 73 (65), 67 (43), 57 (40).

REFERENCE EXAMPLE 24

1-3-(4-Methoxycarbonyl-1-butenyl)-6-exo-(1-methyl-1-methoxyethyloxymethyl)-7-endo-tetrahydropyranyloxybicyclo-[3.3.0]oct-2-ene (106 mg, 0.25 mmol) and methylbenzoatetricarbonylchromium (14 mg, 0.05 mmol) were dissolved in acetone (10 ml) and then degassed. In 100 ml of autoclave and under 70 kg/cm$^2$ of hydrogen gas pressure, the reaction was carried out at 120° C. for 15 hours. Evaporation of the solvent followed by purification through silica gel column chromatography (ether:n-hexane=1:4) to obtain 3E-(4-methoxycarbonylbutylidene)-6-exo-(1-methyl-1-methoxyethyloxymethy)-7-endo-tetrahydropyranyloxybicyclo[3.3.0]octane (95 mg, Yield: 90%). The obtained material did not contain at all a Z-Isomer due to a double bond from the result of analysis by using gas chromatography.

IR (neat): 2970, 2880, 1743, 835 cm$^{-1}$.

NMR δ (CDCl$_3$): 5.20 (t, J=7 Hz, 1H), 4.65 (m, 1H), 3.70 (s, 3H), 3.30–4.10 (m, 5H), 3.20 (s, 3H), 1.33 (s, 6H).

Mass m/z (%): 424 (M+), 393, 340, 85.

REFERENCE EXAMPLE 25

1-3-(4-Methoxycarbonyl-1-butenyl)-6-exo-t-butyldimethylsilyloxymethyl-7-endo-(1-methyl-1-methoxyethyloxy)bicyclo[3.3.0]oct-2-ene (113 mg, 0.25 mmol) and methylbenzoatetricarbonylchromium (14 mg, 0.05 mmol) were dissolved in acetone (10 ml) and then degassed. In 100 ml of autoclave and under 70 kg/cm$^2$ of hydrogen gas pressure, the reaction was carried out at 120° C. for 15 hours. Evaporation of the solvent followed by purification through silica gel column chromatography (ether:n-hexane=1:4) to obtain 3E-(4-methoxycarbonylbutylidene)-6-exo-t-butyldimethylsilyloxymethyl-7-endo-(1-methyl-1-methoxyethyloxy)-bicyclo[3.3.0]octane (102 mg, Yield: 90%). The presence of a Z-Isomer structure could not be admitted as the result of analysis by using gas chromatography.

IR (neat): 2970, 2880, 1743, 835 cm$^{-1}$.

NMR δ (CDCl$_3$): 5.21 (t, J=7 Hz, 1H), 3.70 (s, 3H), 3.30–4.10 (m, 3H), 3.20 (s, 3H), 1.33 (s, 6H), 0.90 (s, 9H), 0.05 (s, 6H).

Mass m/z (%): 454, 422, 382, 73, 59, 41.

REFERENCE EXAMPLE 26

1-3-(4-Carboxy-1-butenyl)-6-exo-t-butyldimethylsilyloxymethyl-7-endo-tetrahydropyranyloxybicyclo[3.3.0]oct-2-ene (113 mg, 0.25 mmol) and methylbenzoatetricarbonylchromium (14 mg, 0.05 mmol) were dissolved in acetone (10 ml) and then degassed. In 100 ml of autoclave and under 70 kg/cm$^2$ of hydrogen gas pressure, the reaction was carried out at 120° C. for 15 hours. Evaporation of the solvent followed by purification through silica gel column chromatography (ether) to obtain 3E-(4-carboxybutylidene)-6-exo-t-butyldimethylsilyloxymethyl-7-endo-tetrahydropyranyloxybicyclo[3.3.0]octane (62 mg, Yield: 55%). The obtained material was treated with diazomethane to obtain methyl ester derivative. The spectrum data thereof are completely agreed with that of the compound obtained in Reference Example 10. From the analysis of the methyl ester derivative by using a gas chromatography, the presence of Z-Isomer could not be admitted.

REFERENCE EXAMPLE 27

3E-(4-methoxycarbonylbutylidene)-6-exo-t-butyldimethylsilyloxymethyl-7-endo-tetrahydropyranyloxybicyclo[3.3.0]-octane (100 mg, 0.21 mmol) was dissolved in THF (1.5 ml). To the solution was added tetra-n-butylammonium fluoride (1M THF solution 0.32 ml, 0.32 mmol) and the mixture was stirred at room temperature for 13 hours. Then, a saturated saline solution was added thereto and THF was distilled from the mixture under reduced pressure. The resultant aqueous layer was extracted with ether, dried with anhydrous magnesium sulfate and distilled out the solvent therefrom. The residue was purified through silica gel column chromatography (ether:n-hexane=3:2) to obtain d-3E-(4-methoxycarbonylbutylidene)-6-exo-hydroxymethyl-7-endo-tetrahydropyranyloxybicyclo[3.3.0]-octane (74 mg, 98%).

IR (neat): 3480, 2950, 1741 $cm^{-1}$.

NMR $\delta$ (CDCl$_3$): 5.22 (t, J=7 Hz, 1H), 4.65, m, 1H), 3.65 (s, 3H), 3.30–4.00 (m, 5H).

Mass m/z (%): 334 (2), 268 (19), 250 (15), 232 (38), 219 (22), 91 (26), 86 (33), 85 (100).

$[\alpha]_D^{20}$ = −6° (c=1.476, MeOH).

REFERENCE EXAMPLE 28

3E-(4-methoxycarbonylbutylidene)-6-exo-(1-methyl-1-methoxyethyloxymethyl)-7-endo-tetrahydropyranyloxybicyclo-[3.3.0]octane (95 mg, 0.22 mmol) was dissolved in THF (2.4 ml) and under ice-cooling, a 0.5N HCl (1.2 ml) was added to the solution and the mixture was stirred at the same condition for 10 hours. Ethyl acetate (24 ml) was added thereto and a separated organic layer was washed with water and a saturated saline solution and then dried with anhydrous magnesium sulfate. Evaporation of the solvent followed by purification through silica gel column chromatography (ether:n-hexane=1:2) to obtain d-3E-(4-methoxycarbonylbutylidene)-6-exo-hydroxymethyl-7-endo-tetrahydropyranyloxybicyclo[3.3.0]octane (74 mg, Yield: 90%). Various spectrum data thereof was completely agreed with that of the compound obtained in Reference example 27.

REFERENCE EXAMPLE 29

3E-(4-methoxycarbonylbutylidene)-6-exo-t-butyldimethylsilyloxymethyl-7-endo-(1-methyl-1-methoxyethyloxy)bicyclo[3.3.0]octane (50 mg, 0.11 mmol) was dissolved in THF (1 ml) and to the solution was added a THF solution of tetra-n-butylammonium fluoride (0.2 ml) and stirred at room temperature for 13 hours. After evaporation of the solvent under reduced pressure, to the residue was added water and extracted with ether. The separated water layer was washed with a saturated saline solution and dried with anhydrous magnesium sulfate. After evaporation of the solvent, the residue was purified through silica gel column chromatography (ether:n-hexane=1:1) to obtain 3E-(4-methoxycarbonylbutylidene)-6-exo-hydroxymethyl-7-endo-(1-methyl-1-methoxyethyloxy)bicyclo[3.3.0]octane (35 mg, Yield: 95%) as colorless oily products.

IR (neat): 3480, 2950, 1740 $cm^{-1}$.

NMR $\delta$ (CDCl$_3$): 5.22 (t, J=7 Hz, 1H), 3.65 (s, 3H), 3.30–4.20 (m, 3H), 3.20 (s, 3H), 1.30 (s, 6H).

Mass m/z (%): 340, 322, 309, 268, 73.

REFERENCE EXAMPLE 30

Under argon gas atmosphere, d-3E-(4-methoxycarbonylbutylidene)-6-exo-hydroxymethyl-7-endo-tetrahydropyranyloxybicyclo[3.3.0]octane (49 mg, 0.14 mmol) and triethylamine (0.12 ml) were dissolved in DMSO (1.5 ml). To the mixture was added a sulfur trioxide.pyridine complex (67 mg, 0.42 mmol) dissolved in DMSO (1 ml) and the mixture was stirred at room temperature for an hour. The thus obtained mixture was poured into ice-cold water and extracted with ether. The separated ether layer was washed with water and a saturated saline solution. After dryness with anhydrous magnesium sulfate, evaporation of the solvent to obtain 3E-(4-methoxycarbonylbutylidene)-6-exo-formyl-7-endo-tetrahydropyranyloxybicyclo[3.3.0]octane.

On the other hand, sodium hydride (60% oily material, 8 mg, 0.2 mmol) was washed with pentane under argon gas atmosphere and then suspended in THF (1.4 ml). To the suspension was added a solution of dimethyl(2-oxoheptyl)phosphonate (47 mg, 0.21 mmol) in THF (0.2 ml) and the mixture was stirred at room temperature for 30 minutes. To the thus prepared mixture was added the previously prepared THF solution (0.6 ml) of 3E-(4-methoxycarbonylbutylidene)-6-exo-formyl-7-endo-tetrahydropyranyloxybicyclo[3.3.0]octane and the mixture was stirred at room temperature for 30 hours. A saturated aqueous ammonium chloride solution was added thereto and the mixture was extracted with ether. The separated ether layer was washed with a saturated saline solution and dried with anhydrous magnesium sulfate. Evaporation of the solvent followed by purification through silica gel column chromatography (ether:n-hexane=2:5) to obtain 3E-(4-methoxycarbonylbutylidene)-6-exo-(3-oxo-trans-1-octenyl)-7-endo-tetrahydropyranyloxybicyclo[3.3.0]octane (52 mg, Yield: 84%).

IR (neat): 2950, 1740, 1700, 1675, 1630 $cm^{-1}$.

NMR $\delta$ (CDCl$_3$): 6.75 (m, 1H), 6.17 & 6.13 (2xd, J=16 Hz, 1H), 5.25 (t, J=7 Hz, 1H), 4.60, (m, 1H), 3.68 (s, 3H), 3.30–4.20 (m, 3H), 0.90 (t, J=6 Hz, 1H).

Mass m/z (%): 362 (5), 344 (7), 167 (13), 149 (41), 85 (34), 74 (23), 73 (25), 61 (34), 59 (31), 57 (31), 45 (100), 43 (77), 31 (78), 29 (51).

REFERENCE EXAMPLE 31

3E-(4-methoxycarbonylbutylidene)-6-exo-(3-oxo-trans-1-octenyl)-7-endo-tetrahydropyranyloxybicyclo[3.3.0]octane (50 mg, 0.11 mmol) was dissolved in THF (0.09 ml) and a 65% aqueous acetic acid solution (0.9 ml) was added thereto at room temperature. After the mixture was stirred at 50° C. for 2 hours, the mixture was poured into a cooled saturated aqueous sodium hydrogencarbonate solution. The resultant mixture was extracted with ether, washed with a saturated saline solution and dried with anhydrous magnesium sulfate. Evaporation of the solvent followed by purification through silica gel column chromatography (ether:n-hexane=3:2) to obtain d-3E-(4-methoxycarbonylbutylidene)-6-exo-(3-oxo-trans-1-octenyl)-7-endo-hydroxybicyclo[3.3.0]octane (39 mg, Yield: 96%).

The data of the resultant substance here completely agreed with the data described in the literature (Tetrahedron, Vol. 37, No. 25, pp. 4391–4399, 1981).

IR (neat): 3430, 1740, 1695, 1670, 1625, 1435, 1375, 1320, 1250, 1170, 1135, 1080, 986 $cm^{-1}$.

NMR $\delta$ (CDCl$_3$): 6.77 (dd, J=15.5 Hz, 8.0 Hz, 1H), 6.17 (d, J=15.5 Hz, 1H), 5.25 (m, 1H), 3.90 (m, 1H), 3.66 (s, 3H), 0.90 (m, 3H).

Mass m/z (%): 362, 344, 318, 313, 245, 179, 164, 147, 131, 129, 105.

Further, it is confirmed that the thus obtained compound is sole one due to TLC analysis by using a mixed solvent of ethyl acetate:cyclohexane=1:2 which is an eluent capable of separating the E-Isomer and Z-Isomer depending on the above literature. In the literature (Tetrahedron, Vol. 37, No. 25, pp. 4391–4399, 1981), the above compound has been led to carbacycline at high yield.

REFERENCE EXAMPLE 32

In the method as described in Reference example 30, the same procedures were carried out as in Reference example 30 except that 3E-(4-methoxycarbonyl-butylidene)-6-exo-hydroxymethyl-7-endo-(1-methyl-1-methoxyethyloxy)-bicyclo[3.3.0]octane (35 mg, 0.10 mmol) was employed as the starting material to obtain 3E-(4-methoxycarbonylbutylidene)-6-exo-(3-oxo-1-trans-octenyl)-7-endo-(1-methyl-1-methoxyethyloxy)-bicyclo[3.3.0]octane (35 mg, Yield: 80%) as substantially colorless oily products.

IR (neat): 2950, 1740, 1700, 1675, 1630 cm$^{-1}$.
NMR δ (CDCl$_3$): 6.75 (m, 1H), 6.17 & 6.12 (2xd, J=16 Hz, 1H), 5.25 (t, J=7 Hz, 1H), 3.90 (m, 1H), 3.68 (s, 3H), 3.20 (s, 3H), 1.34 (s, 6H), 0.90 (t, J=6 Hz, 1H).
Mass m/z (%): 434, 403, 362, 73.

REFERENCE EXAMPLE 33

In the method as described in Reference example 31, the same procedures were carried out as in Reference example 31 except that 3E-(4-methoxycarbonyl-butylidene)-6-exo-(3-oxo-1-trans-octenyl)-7-endo-(1-methyl-1-methoxyethyloxy)-bicyclo[3.3.0]octane (35 mg, 0.081 mmol) was employed as the starting material to obtain d-3E-(4-methoxycarbonylbutylidene)-6-exo-(3-oxo-1-trans-octenyl)-7-endo-hydroxybicyclo[3.3.0]octane (26 mg, Yield: 90%). The thus obtained substance had the same spectrum data as the compound obtained in Reference example 31.

REFERENCE EXAMPLE 34

Under argon gas atmosphere, 4-carboxybutyltri-phenylphosphonium bromide (25.5 g, 57 mmol) which was previously dried at 100° C. under reduced pressure sufficiently was dissolved in 250 ml of THF. Potassium t-butoxide (12.7 g, 114 mmol) was added thereto at room temperature. After the mixture was stirred for 5 minutes, [l-2-oxa-3-hydroxy-6-exo-t-butyldimethyl-silyloxymethyl-7-endo-tetrahydropyranyloxybicyclo[3.3.0]octane] (5.0 g, 13.4 mmol) dissolved in THF (30 ml) was added to the mixture. After the mixture was stirred at room temperature for 30 minutes, to the mixture were added a saturated aqueous ammonium chloride solution (150 ml) and diethyl ether (50 ml). The resultant mixtue was adjusted to pH 5 with a 10% hydrochloric acid and an organic layer and an aqueous layer was separated into respective layer. The aqueous layer was extracted with ethyl acetate (150 ml×3 times) and all the organic layers were combined and washed with a saturated saline solution (30 ml×2 times). After dryness with anhydrous magensium sulfate, evaporation of the solvent followed by dissolution of the residue in ether again. Methylation of the solution was carried out by using diazomethane according to the conventional manner. Ether was distilled out therefrom and the residue was purified through silica gel column chromatography (ether:n-haxane=1:1) to obtain [d-2α-(6-methoxycarbonyl-2-Z-hexenyl)-3β-t-butyldimethyl-silyloxymethyl-4α-tetrahydropyranyloxy-1α-cyclopentanol] (6.1 g, Yield: 97%).

IR (neat): 3580, 1738 cm$^{-1}$.
NMR δ (ppm): 5.40 (2H), 4.65 (1H), 3.65 (s, 3H), 3.20-3.80 (7H), 0.90 (s, 9H), 0.10 (s, 1H).

Mass m/z (%): 470, 413, 386.
Mili-MS: 470.3092; C$_{25}$H$_{46}$O$_6$Si=470.3062.
[α]$_D^{20}$= +22° (c=1.84, MeOH).

REFERENCE EXAMPLE 35

[d-2α-(6-methoxycarbonyl-2-Z-hexenyl)-3β-t-butyl-dimethylsilyloxymethyl-4α-tetrahydropyranyloxy-1α-cyclopentanol] (1.29 g, 2.7 mmol) was dissolved in anhydrous methylene chloride (15 ml) and to the solution were added anhydrous sodium acetate (90 mg, 1.08 mmol) and 1.16 g of celite. To the mixture was added pyridinium chlorochromate (1.16 g, 5.4 mmol) at 0° C. while stirring, and the mixture was further stirred under argon gas atmosphere at 0° C. over night. After to the mixture was added ether (30 ml) and stirred sufficiently, the mixture was filtrated through florisil column. Evaporation of the solvent to obtain substantially pure [l-2α-(6-methoxycarbonyl-2-Z-hexenyl)-3β-t-butyldimethyl-silyloxymethyl-4α-tetrahydropyranyloxy-1-cyclopentanone] (1.19 g, Yield: 92%).

IR (neat): 1742 cm$^{-1}$.
NMR δ (ppm): 5.45 (2H), 4.70 (1H), 3.65 (s, 3H), 3.40–4.00 (5H), 0.90 (s, 9H), 0.10 (6H).
Mass m/z (%): 384 (M$^+$−57), 197 (15), 196 (54), 165 (71), 164 (87), 159 (21), 154 (26), 147 (20), 74 (100).
Mili-MS: 411.2219 (M$^+$-t-Bu);
M$^+$-t-Bu=C$_{21}$H$_{35}$O$_6$Si=411.2201.
[α]$_D^{20}$= −30° (c=1.80, MeOH).

REFERENCE EXAMPLE 36

[l-2α-(6-Methoxycarbonyl-2-Z-hexenyl)-3β-t-butyl-dimethylsilyloxymethyl-4α-tetrahydropyranyloxy-1-cyclopentanone] (100 mg, 0.21 mmol) was dissolved in 0.5 ml of anhydrous methylene chloride, and zinc-titanium tetrachloridemethylene bromide reagent (Zn-TiCl$_4$-CH$_2$Br$_2$/THF, 1.2 ml) was added thereto at room temperature. After comfirming dissolution of the starting material by using TLC, the resultant mixture was poured into a mixed solution of a saturated sodium hydrogencarbonate/ether (20 ml/20 ml). The mixture was stirred until an organic layer became transparent and then the organic layer was separated therefrom. The separated aqueous layer was extracted sufficiently with ether (50 ml×4 times) and all the organic layers were combined and dried with anhydrous magensium sulfate. Evaporation of the solvent, followed by purification through silica gel column chromatography (hexane:ether=5:1) to obtain [l-2α-(6-methoxycarbonyl-2-Z-hexenyl)-3β-t-butyldimethylsilyloxymethyl-4α-tetrahydropyranyloxy-1-cyclopentylidene] (81 mg, Yield: 81%).

IR (neat): 1745, 1660 cm$^{-1}$.
NMR δ (ppm): 5.40 (2H), 4.85 (2H), 4.60 (1H), 3.65 (s, 3H), 3.50–4.20 (5H), 0.90 (s, 9H), 0.10 (s, 6H).
Mass m/z (%): 381 (1), 233 (10), 201 (10), 159 (25), 91 (10), 75 (100).
Mili-MS: 381.2459 (M$^+$−85); M$^+$−85=C$_{21}$H$_{37}$O$_4$-Si=381.2459.
[α]$_D^{20}$−35° (c=1.36, MeOH).

REFERENCE EXAMPLE 37

2-(6-methoxycarbonyl-2-Z-hexenyl)-3-exo-t-butyl-dimethylsilyloxymethyl-4-endo-tetrahydropyranyloxy-1-cyclopentylidene (17.5 mg, 0.037 mmol) was dissolved in anhydrous methylene chloride (0.6 ml). Under argon gas atmosphere and at −25° C., dimethylaluminum chloride (1M hexane solution) (0.19 ml, 0.19 mmol) was added thereto, and the mixture was stirred at −25° C. for 1.5 hours. To the mixture were added a 25% aqueous potassium hydroxide solution (1.9 ml) and ether (3 ml), and the mixture was extracted with ethyl acetate. The separated organic layer was washed successively with a saturated aqueous sodium hydrogencarbonate solution and a saturated saline solution. After dryness with anhydrous magensium sulfate, the mixture was purified through silica gel column chromatography (hexane:ether=1:1) to obtain 2-(6-methoxycarbonyl-2-Z-hexenyl)-3-exo-t-butyldimethylsilyloxymethyl-4-endo-hydroxy-1-cyclopentylidene (12.7 mg, Yield: 89%).

IR (neat): 3450, 2950, 2780, 1745, 1730 cm$^{-1}$.

NMR δ (ppm): 5.40 (2H), 480–4.95 (2H), 3.30–4.20 (4H), 3.65 (s, 3H), 0.90 (s, 9H), 0.10 (s, 6H).

Mass m/z (%): 325 (23), 233 (32), 201 (40), 183 (22), 159 (27), 75 (100).

Mili-MS: 325.1832 (M$^+$−57); M$^+$−57=$C_{17}H_{29}O_4$Si=325.1833.

REFERENCE EXAMPLE 38

[2α -(6-methoxycarbonyl-2-Z-hexenyl)-3β-t-butyldimethylsilyloxymethyl-4α-hydroxy-1-cyclopentylidene] (657 mg, 1.72 mmol) was dissolved in anhydrous dimethylformamide (1.7 ml), and imidazole (40 mg, 5.90 mmol) and t-butyldimethylchlorisilane (596 mg, 3.96 ml) were added thereto. Subsequently, atmosphere in the reaction vessel was replaced with argon gas and the mixture was stirred at room temperature for 15 minutes. To the mixture was added a saturated aqueous ammonium chloride solution and the mixture was extracted with ether (25 ml×4 times). The combined extracts were washed with a saturated saline solution and dried with anhydrous magnesium sulfate. Evaporation of the solvent, followed by purification through silica gel column chromatography (hexane:ether=10:1) to obtain [l-2α-(6-methoxycarbonyl-2-Z-hexenyl)-3β-t-butyldimethylsilyloxymethyl-4α-t-butyldimethylsilyloxy-1-cyclopentylidene (855 mg, Yield: 100%).

IR (neat): 1745, 1660 cm$^{-1}$.

NMR δ (ppm): 5.45 (2H), 4.85 (2H), 4.00 (1H), 3.65 (s, 3H), 0.90 (18H), 0.10 (12H).

Mass m/z (%): 439 (M$^+$-t-Bu) (19), 233 (39), 201 (39), 189 (15), 183 (18), 173 (10), 159 (22), 147 (83), 73 (100).

Mili-MS: 439.2704 (M$^+$-t-Bu); M$^+$-t-Bu=$C_{23}H_{44}O_4Si_2$=439.2698.

$[\alpha]_D^{20}$−38° (c=1.36, MeOH).

REFERENCE EXAMPLE 39

Under argon gas atmosphere, 9-borabicyclo[3.3.0]nonane (dimer, 1.65 g, 13.6 mmol) was suspended in THF (24 ml), and a solution of [l-2α-(6-methoxycarbonyl-2-Z-hexenyl)-3β-butyldimethylsilyloxymethyl-4α-t-butyldimethylsilyloxy-1-cyclopentylidene] (2.70 g, 5.4 mmol) dissolved in THF (10 ml) was added thereto at 0° C. After the mixture was stirred at 0° C. for 2 hours, a 3N aqueous sodium hydroxide solution (5 ml) and a 30% aqueous hydroperoxide solution (5 ml) was added thereto. The mixture was heated to 60° C. and stirred for 1.5 hours. After almost all the THF was distilled out, to the residue was added ether (30 ml) and adjusted to pH 5 with a 10% hydrochloric acid. The mixture was extracted with ethyl ether and the extract was washed with a saturated aqueous sodium thiosulfate solution and a saturated saline solution and then dried with anhydrous magnesium sulfate. Evaporation of the solvent, followed by purification through silica gel column chromatography (hexane:ether=3:2 to 1:1) to obtain [d-1α-hydroxymethyl-2α-(6-methoxycarbonyl-2-Z-hexenyl)-3β-t-butyldimethylsilyloxymethyl-4α-t-butyldimethylsilyloxycyclopentane] (1.97 g, Yield: 71%).

IR (neat): 3450, 1742 cm$^{-1}$.

NMR δ (ppm): 5.40 (2H), 4.15 (1H), 3.65 (s, 3H), 3.20–3.80 (5H), 0.90 (18H), 0.10 (s, 6H), 0.05 (s, 6H).

Mass m/z (%): 514 (M$^+$, 1.4), 233 (42), 221 (22), 219 (11), 201 (34), 189 (20), 73 (100).

Mili-MS: 514.3515 (M$^+$); $C_{27}H_{54}O_5Si_2$=514.3506.

$[\alpha]_D^{20}$+4° (c=1.36, MeOH).

REFERENCE EXAMPLE 40

Under argon gas atmosphere, [d-1α-hydroxymethyl-2α-(6-methoxycarbonyl-2-Z-hexenyl)-3β-t-butyldimethylsilyloxymethyl-4α-t-butyldimethylsilyloxycyclopentane] (1.77 g, 3.44 mmol) was dissolved in anhydrous methylene chloride (70 ml), and Collins reagent (8.8 g, 34 mmol) was added thereto at 0° C. After the mixture was stirred at 0° C. for 30 minutes, 17.6 g of sodium hydrogensulfate monohydrate was added thereto and the mixture was diluted with methylene chloride. The resultant mixture was returned to room temperature and to the mixture was added ether until the whole mixture became turbid. After to the mixture was added anhydrous magnesium sulfate and stirred for 5 minutes, the mixture was filtrated through florisil column. By removing the solvent in the filtrate, purified [d-1α-formyl-2α-(6-methoxycarbonyl- 2-Z-hexenyl)-3β-t-butyldimethylsilyloxymethyl-4α-t-butyldimethylsilyloxycyclopentane] was obtained (1.60 g, Yield: 91%).

IR (neat): 1750, 1730 (sh) cm$^{-1}$.

NMR δ (ppm): 9.85 (d, 1H), 5.35 (2H), 4.20 (1H), 3.65 (s, 3H), 3.40–3.60 (2H), 2.80 (1H), 0.90 (18H), 0.10 (s, 6H), 0.05 (s, 6H).

Mass m/z (%): 497 (M$^+$−15) (1.5), 456 (16.5), 455 (M$^+$−57) (46), 363 (12), 323 (12), 249 (17), 231 (21), 217 (22), 199 (43), 189 (27), 181 (12), 171 (30), 73 (100).

$[\alpha]_D^{20}$= +1° (c=1.00, MeOH).

EXAMPLE 28

[d-1α-Formyl-2α-(6-methoxycarbonyl-2-Z-hexenyl)-3β-t-butyldimethylsilyloxymethyl-4α-t-butyldimethylsilyloxycyclopentane] (1.65 g, 3.22 mmol) was dissolved in anhydrous toluene (33 ml) and the solution was charged in a sealed tube under argon gas atmosphere. The tube was heated at 180° C. for 18 hours. After evaporation of the toluene, the residue was purified through silica gel column chromatography (hexane:ether=3:1 to 1:1) to obtain [2-hydroxy-3-(4-methoxycarbonyl-1-butenyl)-6-exo-t-butyldimethylsilyloxymethyl-7-endo-t-butyldimethylsilyloxybicyclo[3.3.0]octane] (1.44 g, Yield: 87%) as scarcely colored oily products. According to the spectrum data thereof, it was confirmed that the obtained products were mixtures of 2,3-exo,exo and 2,3-endo,endo compounds.

IR (neat): 3430, 1740, 1720 (sh) cm$^{-1}$.

NMR δ (ppm): 5.20–6.00 (2H), 4.30 (0.4H), 3.10–4.00 (3.6H), 3.65 (s, 3H), 0.90 (18H), 0.05–0.10 (12H).

Mass m/z (%): 455 (18), 437 (13), 323 (3D), 249 (19), 231 (70), 218 (13), 217 (68), 205 (16), 199 (59), 189 (47), 181 (14), 171 (43), 157 (45), 155 (14), 147 (87), 73 (100).

EXAMPLE 29

[2-hydroxy-3-(4-methoxycarbonyl-1-butenyl)-6-exo-t-butyldimethylsilyloxymethyl-7-endo-t-butyldimethylsilyloxybicyclo[3.3.0]octane] (2,3-exo,exo and 2,3-endo,endo mixture; 12 mg, 0.023 mmol) was dissolved in methanol (0.3 ml), and a 10% palladium carbon (3.0 mg) was added thereto and catalytic reduction was carried out by using hydrogen gas. The reaction was followed up by a TLC of AgNO$_3$-silica gel and the starting materials were disappeared after 2 hours. The resultant mixture was diluted with ether and palladium carbon was removed by filtration with the addition of Celite. Evaporation of the solvent yielded [2-hydroxy-3-(4-methoxycarbonylbutyl)-6-exo-t-butyldimethylsilyloxymethyl-7-endo-t-butyldimethylsilyloxybicyclo[3.3.0]octane] (12 mg, Yield: 100%) as substantially colorless oily products.

IR (neat): 3450, 1742, 1725 (sh) cm$^{-1}$.

NMR δ (ppm): 4.30 (0.4H), 3.0–4.1 (3.6H), 3.65 (s, 3H), 0.90 (18H), 0.10 (6H), 0.05 (6H).

Mass m/z (%): 457 (38), 325 (40), 233 (90), 219 (100), 201 (69).

EXAMPLE 30

In toluene (25 ml) was dissolved [2-hydroxy-3-(4-methoxycarbonyl-1-butenyl)-6-exo-t-butyldimethylsilyloxymethyl-7-endo-t-butyldimethylsilyloxybicyclo[3.3.0]octane] (1.11 g, 2.12 mmol). To the solution were added triethylamine (2.1 g) and methane sulfonyl chloride (2.3 g) and the mixture was stirred at room temperature for 30 minutes. To the mixture was added DBU (1,8-diazabicyclo[5.4.0]-unde-7-cene, about 3 g) and the mixture was refluxed for about 12 hours. After the reaction mixture was diluted with ether, the mixture was washed successively with a 10% aqueous hydrochloric acid solution, a saturated aqueous sodium hydrogencarbonate solution and a saturated saline solution, and dried with anhydrous magnesium sulfate. After evaporation of the solvent, the residue was purified through silica gel column chromatography to obtain [3-(4-methoxycarbonyl-1E-butenyl)-6-exo-t-butyldimethylsilyloxymethyl-7-endo-t-butyldimethylsilyloxybicyclo[3.3.0]oct-2-ene (597 mg, Yield: 57%).

IR (neat): 1745 cm$^{-1}$.

NMR δ (ppm): 6.25 (d, J=16 Hz, 1H), 5.30–5.70 (m, 2H), 3.70–4.10 (m, 1H), 3.65 (s, 3H), 3.30–3.70 (m, 2H), 0.90 (s, 18H), 0.10 (s, 6H), 0.05 (s, 6H).

Mass m/z (%): 437 (M$^+$−57).

From the spectrum data obtained above, it is identified that the stereochemistry of the di-substituted olefin is the trans form.

EXAMPLE 31

[2-hydroxy-3-(4-methoxycarbonylbutyl)-6-exo-t-butyldimethylsilyloxymethyl-7-endo-t-butyldimethylsilyloxybicyclo[3.3.0]octane] (12 mg) was dissolved in pyridine (0.5 ml), and under argon gas atmosphere, methanesulfonyl chloride (11 μl) was added thereto and the mixture was stirred at room temperature. Methanesulfonyl chloride (10 μl) was added thereto every 30 minutes until the starting materials were disappeared by TLC. After confirmation of disappearance of the starting materials, a saturated aqueous ammonium chloride solution was added thereto and extracted with ether. The separated organic layer was washed three times with a saturated aqueous copper sulfate solution. The organic layer was dried with anhydrous magnesium sulfate and then the solvent was distilled out therefrom. The residue was dissolved in toluene (0.2 ml) and to the solution was added diazabicycloundecene (20 μl) and stirred at 100° C. for 2 days under argon gas atmosphere. The resultant mixture was cooled to room temperature and to the mixture was added a saturated aqueous ammonium chloride solution. The resultant mixture was extracted with ether and the separated ether layer was washed with a saturated saline solution and then dried with anhydrous magnesium sulfate. Evaporation of the solvent, followed by purification through silica gel column chromatography (hexane:ether=10:1) to obtain [1-3-(4-methoxycarbonylbutyl)-6-exo-t-butyldimethylsilyloxymethyl-7-endo-t-butyldimethylsilyloxybicyclo[3.3.0]oct-2-ene] (5.6 mg, Yield: 48%).

IR (neat): 1745 cm$^{-1}$.

NMR δ (ppm): 5.30 (1H), 3.85 (1H), 3.65 (s, 3H), 3.60 (2H), 2.90 (1H), 0.90 (s, 9H), 0.85 (s, 9H), 0.05 (12H).

Mass m/z (%): 439 (M$^+$−57) (25), 243 (11), 233 (64), 207 (53), 201 (42), 189 (11), 183 (21), 175 (19), 173 (14), 159 (14), 157 (14), 149 (17), 148 (12), 147 (67), 73 (100).

Mili-MS: 439.2697 (M$^+$-t-Bu); M$^+$-t-Bu=C$_{23}$H$_{43}$O$_4$Si$_2$=439.2697.

EXAMPLE 32

{1-3-(4'-Methoxycarbonyl-1'-butenyl)-6-exo-t-butyldimethylsilyloxymethyl-7-endo-tetrahydropyranyloxybicyclo[3.3.0]oct-2-ene} (464 mg, 1 mmol) was dissolved in THF (4.6 ml). To the thus prepared solution was added a tetra-n-butylammonium fluoride solution (1M THF solution, 1.5 ml), followed by stirring at room temperature for 13 hours. After the solvent was distilled out under reduced pressure, to the residue was added water, followed by extraction with ether. The separated ether layer was washed with a saturated saline solution, and dried with anhydrous magnesium sulfate. After the solvent was distilled out, the residue was purified through silica gel column chromatography (ether:n-hexane=1:2) to obtain {3-(4'-methoxycarbonyl-1'-butenyl)-6-exo-hydroxymethyl-7-endo-tetrahydropyranyloxybicyclo[3.3.0]oct-2-ene} (333 mg, Yield: 95%) as colorless oily product.

IR (neat): 3480, 1740 cm$^{-1}$.

NMR δ (CDCl$_3$): 6.26 (d, J=15 Hz, ⅓H, trans), 6.00 (d, J=12 Hz, 2/3H, cis), 5.58 (s, 1H), 5.35 (m, 1H), 4.62 (m, 1H), 3.68 (s, 3H), 3.30–4.30 (m, 5H), 3.00 (m, 1H).

Mass m/z: 350, 266.

EXAMPLE 33

{3-(4'-Carboxy-1'-butenyl)-6-exo-t-butyldimethylsilyloxymethyl-7-endo-tetrahydropyranyloxybicyclo[3.3.0]oct-2-ene} (450 mg, 1 mmol) was dissolved in acetonitrile (2 ml). To the thus prepared solution were added DBU (304 mg, 2 mmol) and ethyl iodide (468 mg, 3 mmol) at room temperature, followed by stirring for further 3 hours. After the reaction was stopped with addition of a saturated aqueous ammonium chloride solution, the resultant mixture was extracted with ether. The separated ether layer was washed with a saturated saline solution, followed by drying with anhydrous magnesium sulfate. After the solvent was distilled out, the residue was purified through silica gel column chromatography to obtain {3-(4'-ethoxycarbonyl-1'-butenyl)-6-exo-t-butyldimethylsilyloxymethyl-7-endo-tetrahydropyranyloxybicyclo[3.3.0]oct-2-ene} (400 mg, Yield: 84%) as colorless oily product.

IR (neat): 2950, 2870, 1745, 840 cm$^{-1}$.

NMR δ (CDCl$_3$): 6.24 (d, J=16 Hz, ⅓H, trans), 5.98 (d, J=11 Hz, ⅔H, cis), 5.57 (bs, 1H), 5.30 (m, 1H), 4.60 (bs, 1H), 4.20 (q, J=7 Hz, 2H), 3.20–4.20 (m, 5H), 2.95 (m, 1H), 1.30 (t, J=7 Hz, 3H), 0.90 (s, 9H).

Mass m/z: 478 (M$^+$), 433, 421, 393.

{3-(4'-Ethoxycarbonyl-1'-butenyl)-6-exo-t-butyl-dimethylsilyloxymethyl-7-endo-tetrahydropyranyloxybicyclo[3.3.0]oct-2-ene} (400 mg, 0.84 mmol) was dissolved in THF (4 ml). To the thus prepared solution was added a tetrabutylammonium fluoride (1M THF solution, 1.3 ml), followed by stirring at room temperature for 12 hours. After the reaction was stopped by adding a saturated aqueous ammonium chloride solution, THF was distilled out under reduced pressure. The resultant aqueous layer was extracted with an ether and the separated ether layer was washed with a saturated saline solution, followed by drying with anhydrous magnesium sulfate. After the solvent was distilled out, the residue was purified through silica gel column chromatography to obtain {3-(4'-ethoxycarbonyl-1'-butenyl)-6-exo-hydroxymethyl-7-endo-tetrahydropyranyloxybicyclo[3.3.0]oct-2-ene} (306 mg, Yield: 100%) as nearly colorless oily product.

IR (neat): 3480, 1740 cm$^{-1}$.

NMR δ (CDCl$_3$): 6.26 (d, J=15 Hz, ⅓H, trans), 6.00 (d, J=12 Hz, ⅔H, cis), 5.58 (s, 1H), 5.32 (m, 1H), 4.60 (m, 1H), 3.30–4.30 (m, 5H), 4.20 (q, J=7 Hz, 2H), 3.00 (m, 1H), 1.30 (t, J=7 Hz, 3H).

Mass m/z: 364, 280.

EXAMPLE 34

Under argon gas atmosphere, {3-(4'-methoxycarbonyl-1'-butenyl)-6(S)-hydroxymethyl-7(R)-tetrahydropyranyloxy-(1S,5S)-cis-bicyclo[3.3.0]oct-2-ene} (stereochemistry of the double bond is E:Z=1:2) (422 mg, 1.2 mmol) and triethylamine (0.98 ml) were dissolved in DMSO (10 ml). To the thus prepared solution was added a DMSO solution (7.5 ml) of sulfurtrioxide-pyridine complex (575 mg, 3.6 mmol), followed by stirring at room temperature for 30 minutes. The resultant mixture was poured into the ice-cold water, followed by extraction with ether. The separated ether layer was washed with water and a saturated saline solution. The residue was dried with anhydrous magnesium sulfate and the solvent was distilled out to obtain {3-(4'-methoxycarbonyl-1'-butenyl)-6(R)-formyl-7(R)-tetrahydropyranyloxy-(1S,5S)-cis-bicyclo[3.3.0]oct-2-ene}.

On the other hand, sodium hydride (60% oily product, 67 mg, 1.68 mmol) was washed with an n-pentane and suspended in THF (10 ml). To the thus prepared mixture was added a THF solution (3 ml) of dimethyl(2-oxo-3-methyl-5-heptynyl)phosphonate (418 mg, 1.8 mmol), followed by stirring at room temperature for 30 minutes. To the resultant mixture was added the above-mentioned THF solution (6 ml) of {3-(4'-methoxycarbonyl-1'-butenyl)-6(R)-formyl-7(R)-tetrahydropyranyloxy-(1S,5S)-cis-bicyclo[3.3.0]oct-2-ene}. After the resultant mixture was stirred at room temperature for further 1 hour, a saturated aqueous ammonium chloride solution was added thereto. The thus prepared mixture was extracted with ether and the separated ether layer was washed with a saturated saline soluion. The resultant mixture was dried with anhydrous magnesium sulfate and the solvent was distilled out. The residue was purified through silica gel colomn chromatography to obtain {3-(4'-methoxycabonyl-1'-butenyl)-6(S)-(3'-oxo-4'(RS)-methyl-trans-1'-octen-6'-ynyl)-7(R)-tetrahydropyranyloxy-(1S,5S)-cis-bicyclo[3.3.0]oct-2-ene} (460 mg, Yield: 84%) as colorless oily product.

IR (neat): 1740, 1695, 1680, 1625 cm$^{-1}$.

NMR δ (CDCl$_3$): 6.80 (m, 1H), 5.80–6.50 (m, 2H), 5.00–5.70 (m, 2H), 4.60 (m, 1H), 3.68 (s, 3H), 1.75 (t, J=2 Hz, 3H), 1.20 (d, J=7 Hz, 3H).

Mass m/z: 454, 370, 85.

EXAMPLE 35

The reaction was carried out following the same procedure as in Example 34 to synthesize {3-(4'-methoxycarbonyl-1'-butenyl)-6(R)-formyl-7(R)-tetrahydropyranyloxy-(1S,5S)-cis-bicyclo[3.3.0]oct-2-ene}. The thus obtained compound was reacted with dimethyl(2-oxo-4(R)-methyl-8-methyl-7-nonenyl)phosphonate (479 mg, 1.8 mmol) to obtain {3-(4'-methoxycarbonyl-1'-butenyl)-6(S)-(3'-oxo-5'(R)-methyl-9'-methyl-trans-1'-decene-8'-enyl)-7(R)-tetrahydropyranyloxy-(1S,5S)-cis-bicyclo[3.3.0]oct-2-ene} (500 mg, Yield: 85%).

IR (neat): 1745, 1700, 1675, 1625 cm$^{-1}$.

NMR δ (CDCl$_3$): 6.80 (m, 1H), 5.80–6.50 (m, 2H), 4.90–5.70 (m, 3H), 4.65 (m, 1H), 3.70 (s, 3H), 0.93 (d, J=6 Hz, 3H).

Mass m/z: 414, 396, 85.

EXAMPLE 36

The reaction was carried out following the same procedures as in Example 34 by using {3-(4'-ethoxycarboxny-1'-butenyl)-6(S)-hydroxymethyl-7(R)-tetrahydropyranyloxy-(1S,5S)-cis-bicyclo[3.3.0]oct-2-ene} (437 mg, 1.2 mmol) to synthesize {3-(4'-ethoxycarbonyl-1'-butenyl)-6(R)-formyl-7(R)-tetrahydropyranyloxy-(1S,5S)-cis-bicyclo[3.3.0]oct-2-ene} and finally yielded {3-(4'-ethoxycarbonyl-1'-butenyl)-6(S)-(3'-oxo-5'(R)-methyl-trans-1'-decene-8'-enyl)-7(R)-tetrahydropyranyloxy-(1S,5S)-cis-bicyclo-3.3.0]oct-2-ene} (522 mg, Yield: 85%) as colorless oily product.

IR (neat): 1745, 1695, 1680, 1625 cm$^{-1}$.

NMR δ (CDCl$_3$): 6.80 (m, 1H), 5.80–6.50 (m, 2H), 4.90–5.70 (m, 3H), 4.65 (m, 1H), 4.20 (q, 2H, J=7 Hz), 1.30 (t, J=7 Hz, 3H), 0.93 (d, J=6 Hz, 3H).

Mass m/z: 428, 410.

EXAMPLE 37

The reaction was carried out following the same procedures as in Example 34 by using {3-(4'-methoxycarbonyl-1'-butenyl)-6(S)-hydroxymethyl-7(R)-tetrahydropyranyloxy-(1S,5S)-cis-bicyclo[3.3.0]oct-2-ene} (422 mg, 1.2 mmol) to synthesize {3-(4'-methoxycarbonyl-1'-butenyl)-6(R)-formyl-7(R)-tetrahydropyranyloxy-(1S,5S)-cis-bicyclo[3.3.0]oct-2-ene} and finally yielded {3-(4'-methoxycarbonyl-1'-butenyl)-6(S)-(3'-oxo-trans-1'-octenyl)-7(R)-tetrahydropyranyloxy-(1S,5S)-cis-bicyclo[3.3.0]oct-2-ene} (458 mg, Yield: 86%) as colorless oily product.

IR (neat): 1740, 1680, 1625 cm$^{-1}$.

NMR δ (CDCl$_3$): 6.75 (m, 1H), 5.80–6.40 (2H), 5.00–5.70 (m, 2H), 4.60 (m, 1H), 3.67 (s, 3H).

Mass m/z: 444, 360.

EXAMPLE 38

The reaction was carried out following the same procedures as in Example 34 by using {3-(4'-methoxycarbonyl-1'-butenyl)-6(S)-hydroxymethyl-7(R)-tetrahydropyranyloxy-(1S,5S)-cis-bicyclo[3.3.0]oct-2-ene} (422 mg, 1.2 mmol) to synthesize {3-(4'-methoxycarbonyl-1'-butenyl)-6(R)-formyl-7(R)-tetrahydropyranyloxy-(1S,5S)-cis-bicyclo-[3.3.0]oct-2-ene} and finally yielded {3-(4'-methoxycarbonyl-1'-butenyl)-6(S)-(3'-oxo-3'-cyclopentyl-trans-1'-propenyl)-7(R)-tetrahydropyranyloxy-(1S,5S)-cis-bicyclo[3.3.0]oct-2-ene} (440 mg, Yield: 83%) as colorless oily product.

IR (neat): 1740, 1700, 1670, 1630 cm$^{-1}$.

NMR δ (CDCl$_3$): 6.80 (m, 1H), 5.80–6.50 (m, 2H), 5.00–5.70 (m, 2H), 4.60 (m, 1H), 3.68 (s, 3H).

Mass m/z: 442, 411, 358.

EXAMPLE 39

The reaction was carried out following the same procedures as in Example 34 by using {3-(4'-ethoxycarbonyl-1'-butenyl)-6(S)-hydroxymethyl-7(R)-tetrahydropyranyloxy-(1S,5S)-cis-bicyclo[3.3.0]oct-2-ene} (437 mg, 1.2 mmol) to synthesize {3-(4'-ethoxycarbonyl-1'-butenyl)-6(R)-formyl-7(R)-tetrahydropyranyloxy-(1S,5S)-cis-bicyclo[3.3.0]oct-2-ene} and finally yielded {3-(4'-ethoxycarbonyl-1'-butenyl)-6(S)-(3'-oxo-4'(RS)-methyl-trans-1'-octen-6'-ynyl)-7(R)-tetrahydropyranyloxy-(1S,5S)-cis-bicyclo[3.3.0]oct-2-ene} (455 mg, Yield: 81%) as colorless oily product.

IR (neat): 1740, 1694, 1678, 1625 cm$^{-1}$.

NMR δ (CDCl$_3$): 6.80 (m, 1H), 5.80–6.50 (m, 2H), 5.00–5.70 (m, 2H), 4.60 (m, 1H), 4.20 (q, J=7 Hz, 2H), 1.75 (t, J=2 Hz, 3H), 1.30 (t, J=7 Hz, 3H), 1.20 (d, J=7 Hz, 3H).

Mass m/z: 468, 384.

EXAMPLE 40

The reaction was carried out following the same procedures as in Example 34 by using {3-(4'-ethoxycarbonyl-1'-butenyl)-6(S)-hydroxymethyl-7(R)-tetrahydropyranyloxy-(1S,5S)-cis-bicyclo[3.3.0]oct-2-ene} (437 mg, 1.2 mmol) to synthesize {3-(4'-ethoxycarbonyl-1'-butenyl)-6(R)-formyl-7(R)-tetrahydropyranyloxy-(1S,5S)-cis-bicyclo [3.3.0]oct-2-ene} and finally yielded {3-(4'-ethoxycarbonyl-1'-butenyl)-6(S)-(3'-oxo-3'-cyclopentyl-trans-1'-propenyl)-7(R)-tetrahydropyranyloxy-[3.3.0]oct-2-ene} (454 mg, Yield: 83%) as colorless oily product.

IR (neat): 1740, 1700, 1670, 1630 cm$^{-1}$.

NMR δ (CDCl$_3$): 6.80 (m, 1H), 5.80–6.50 (m, 2H), 5.00–5.70 (m, 2H), 4.60 (m, 1H), 4.20 (q, J=7 Hz, 2H), 1.30 (t, J=7 Hz, 3H).

Mass m/z: 456, 372.

EXAMPLE 41

{3-(4'-Methoxycarbonyl-1'-butenyl)-6(S)-(3'-oxo-trans-1'-octenyl)-7(R)-tetrahydropyranyloxy-(1S,5S)-cis-bicyclo-[3.3.0]oct-2-ene} (73 mg, 0.16 mmol) was dissolved in methanol (2.6 ml). With addition of sodium borohydride (6 mg, 0.16 mmol) at −25° C., the mixture was stirred at −25° C. for 40 minutes. After the reaction was stopped with addition of an acetone, a saturated aqueous ammonium chloride solution was added to the mixture. After the methanol was distilled out, the resultant aqueous layer was extraced with ether. The separated ether layer was washed with a saturated saline solution and dried with anhydrous magnesium sulfate. The solvent was distilled out and the residue was purified through silica gel column chromatography to obtain {3-(4'-methoxycarbonyl-1'-butenyl)-6(S)-(3'(RS)-hydroxy-trans-1'-octenyl-7(R)-tetrahydropyranyloxy-(1S, 5S)-cis-bicyclo[3.3.0]oct-2-ene} (74 mg, Yield: 100%) as nearly colorless oily product.

IR (neat): 3470, 1745 cm$^{-1}$.

NMR δ (CDCl$_3$): 6.28 (d, J=16 Hz, 1/3H, trans), 6.00 (d, J=11 Hz, ⅔H, cis), 5.10–5.75 (m, 4H), 4.67 (m, 1H), 3.70 (s, 3H).

Mass m/z: 446, 230.

EXAMPLE 42

The reaction was carried out following the same procedures as in Example 41 by using {3-(4'-methoxycarbonyl-1'-butenyl)-6(S)-(3'-oxo-3'-cyclopentyl-trans-1'-propenyl)-7(R)-tetrahydropyranyloxy-(1S,5S)-cis-bicyclo[3.3.0]oct-2-ene} (130 mg, 0.29 mmol) to obtain (3-(4'-methoxycarbonyl-1'-butenyl)-6(S)-(3'(RS)-hydroxy-3'-cyclopentyl-trans-1'-propenyl)-7(R)-tetrahydropyranyl-oxy-(1S, 5S)-cis-bicyclo[3.3.0]oct-2-ene} (131 mg, Yield: 100%) as colorless oily product.

IR (neat): 3500, 1742 cm$^{-1}$.

NMR δ (CDCl$_3$): 6.28 (d, J=16 Hz, ⅓H, trans), 6.00 (d, J=11 Hz, ⅔H, cis), 5.10–5.80 (m, 4H), 4.70 (m, 1H), 3.70 (s, 3H).

Mass m/z: 444, 342, 298, 220.

EXAMPLE 43

{3-(4'-Methoxycarbonyl-1'-butenyl)-6(S)-(3'-oxo-4'(RS)-methyl-trans-1'-octen-6'-ynyl)-7(R)-tetrahydropyranyloxy-(1S,5S)-cis-bicyclo[3.3.0]oct-2-ene} (450 mg, 0.99 mmol) was dissolved in methanol (10 ml). With addition of excess amount of sodium borohydride at −25° C., the mixture was stirred at −25° C. for 1 hour. After the reaction was stopped with addition of an acetone, a saturated aqueous ammonium chloride solution was added to the mixture. After the methanol was distilled out, the resultant aqueous layer was extraced with ehter. The separated ether layer was washed with a saturated saline solution and dried with anhydrous magnesium sulfate. The solvent was distilled out and the residue was purified through silica gel column chromatography to obtain {3-(4'-methoxycarbonyl-1'-butenyl)-6(S)-(3'-(RS)-hydroxy-4'(RS)-methyl-trans-1'-octen-6'-ynyl)-7(R)-tetrahydropyranyloxy-(1S5S)-cis-bicyclo[3.3.0]oct-2-ene} (377 mg, Yield: 84%) as nearly colorless oily product.

IR (neat): 3500, 1745 cm$^{-1}$.

NMR δ (CDCl$_3$): 6.30, 6.02 (each d, J=16 Hz, J=12 Hz, 1H), 5.20–5.80 (m, 4H), 4.60 (m, 1H), 3.71 (s, 3H), 1.69 (t, J=2 Hz, 3H), 1.00 (m, 3H).

Mass m/z: 372, 354, 85.

EXAMPLE 44

The reaction was carried out following the same procedures as in Example 43 by using {3-(4'-methoxycarbonyl-1'-butenyl)-6(S)-(3'-oxo-5'(R)-methyl-9'-methyl-trans-1'-decene-8'-enyl)-7(R)-tetrahydropyranyloxy-(1S,5S)-cis-bicyclo[3.3.0]oct-2-ene} (490 mg, 0.98 mmol) to obtain {3-(4'-methoxycarbonyl-1'-butenyl)-6(S)-(3'(RS)-hydroxy-5'(R)-methyl-9'-methyl-trans-1'-decene-8'-enyl)-7(R)-tetrahydropyranyloxy-(1S, 5S)-cis-bicyclo[3.3.0]oct-2-ene} (492 mg, Yield: 100%) as nearly colorless oily product.

IR (neat): 3500, 1745 cm$^{-1}$.

NMR δ (CDCl$_3$): 6.26, 6.00 (each d, J=15 Hz, J=11 Hz, 1H), 5.00–5.62 (m, 5H), 4.68 (m, 1H), 3.69 (s, 3H), 1.68 (s, 3H), 1.58 (s, 3H), 0.90 (d, J=6 Hz, 3H).

Mass m/z: 500, 482, 416, 85.

EXAMPLE 45

The reaction was carried out following the same procedures as in Example 1 by using {3-(4'-ethoxycarbonyl-1'-butenyl)-6(S)-(3'-oxo-5'(R)-methyl-9'-methyl-trans-1'-decene-8'-enyl)-7(R)-tetrahydropyranyloxy-(1S,5S)-cis-bicyclo[3.3.0]-oct-2-ene} (502 mg, 0.98 mmol) to obtain {3-(4'-ethoxycarbonyl-1'-butenyl)-6(S)-(3'(RS)-hydroxy-5'(R)-methyl-9'-methyltrans-1'-decene-8'-enyl)-7(R)-tetrahydropyranyloxy-(1S, 5S)-cis-bicyclo[3.3.0]oct-2-ene} (504 mg, Yield: 100%) as nearly colorless oily product.

IR (neat): 3500, 1745 cm$^{-1}$.

NMR δ (CDCl$_3$): 6.26, 6.00 (each d, J=15 Hz, J=11 Hz, 1H), 5.00–5.62 (m, 5H), 4.68 (m, 1H), 4.20 (q, J=7 Hz, 2H), 1.30 (t, J=7 Hz, 3H), 0.93 (d, J=6 Hz, 3H).

Mass m/z: 514, 496, 430.

EXAMPLE 46

The reaction was carried out following the same procedures as in Example 41 by using {3-(4'-ethoxycarbonyl-1'-butenyl)-6(S)-(3'-oxo-3'-cyclopentyl-trans-1'-propenyl)-7(R)-tetrahydropyranyloxy-(1S,5S)-cis-bicyclo-[3.3.0]oct-2-ene} (132 mg, 0.29 mmol) to obtain {3-(4'-ethoxycarbonyl-1'-butenyl)-6(S)-(3'(RS)-hydroxy-3'-cyclopentyl-trans-1'-propenyl)-7(R)-tetrahydropyranyloxy-(1S,5S)-cis-bicyclo[3.3.0]oct-2-ene} (133 mg, Yield: 100%) as nearly colorless oily product.

IR (neat): 3500, 1742 cm$^{-1}$.

NMR δ (CDCl$_3$): 6.28 (d, J=16 Hz, ½H, trans), 6.00 (d, J=11 Hz, ⅔H, cis), 5.10–5.80 (m, 4H), 4.70 (m, 1H), 4.20 (q, J=7 Hz, 2H), 1.30 (t, J=7 Hz, 3H).

Mass m/z: 458, 356.

EXAMPLE 47

The reaction was carried out following the same procedures as in Example 41 by using {3-(4'-ethoxycarbonyl-1'-butenyl)-6(S)-(3'-oxo-4'(RS)-methyl-trans-1'-octen-6'-ynyl)-7(R)-tetrahydropyranyloxy-(1S,5S)-cis-bicyclo-[3.3.0]oct-2-ene} (136 mg, 0.29 mmol) to obtain {3-(4'-ethoxycarbonyl-1'-butenyl)-6(S)-(3'(RS)-hydroxy-4'(RS)-methyl-trans-1'-octen-6'-ynyl)-7(R)-tetrahydropyranyloxy-(1S, 5S)-cis-bicyclo[3.3.0]oct-2-ene} (136 mg, Yield: 100%) as nearly colorless oily product.

IR (neat): 3500, 1743 cm$^{-1}$.

NMR δ (CDCl$_3$): 6.28 (d, J=16 Hz, ½H, trans), 6.00 (d, J=11 Hz, ⅔H, cis), 5.10–5.80 (m, 4H), 4.70 (m, 1H), 4.20 (q, J=7 Hz, 2H), 1.75 (t, J=2 Hz, 3H), 1.30 (t, J=7 Hz, 3H), 1.20 (d, J=7 Hz, 3H).

Mass m/z: 470, 368.

EXAMPLE 48

{3-(4'-Methoxycarbonyl-1'-butenyl)-6(S)-(3'(RS)-hydroxytrans-1'-octenyl)-7(R)-tetrahydropyranyloxy-(1S,5S)-cis-bicyclo[3.3.0]oct-2-ene} (446 mg, 1 mmol) was dissolved in THF (0.16 ml). With addition of a 65% aqueous acetic acid solution (2.6 ml) thereto, the mixture was stirred at 50° C. for 2 hours. The resultant mixture was poured into a cooled saturated aqueous sodium hydrogencarbonate solution and the mixture was extracted with ethyl acetate. The separated organic layer was washed with a saturated saline solution and dried with anhydrous magnesium sulfate. The solvent was distilled out and the residue was purified through silica gel column chromatography to obtain {3-(4'-methoxycarbonyl-1'-butenyl)-6(S)-3'(R)-hydroxy-trans-1'-octenyl)-7(R)-hydroxy-(1S,5S)-cis-bicyclo[3.3.0]oct-2-ene} (119 mg, Yield: 33%) as a lower polarity component and {3-(4'-methoxycarbonyl-1'-butenyl)-6(S)-(3'(S)-hydroxy-trans-1'-octenyl)-7(R)-hydroxy-(1S,5S)-cis-bicyclo[3.3.0]oct-2-ene} (214 mg, Yield: 59%) as a higher polarity component, each as colorless oily products.

Spectrum data of the higher polarity component were as follows:

IR (neat): 3400, 1742 cm$^{-1}$.

NMR δ (CDCl$_3$) 6.30 (d, J=15 Hz, ½H, trans), 6.02 (d, J=11 Hz, ⅔H, cis), 5.00–5.70 (m, 4H), 4.10 (m, 1H) 3.70 (s, 3H), 3.02 (m, 1H).

Mass m/z: 362, 344.

$[α]_D^{20} = -35°$ (c=0.466, MeOH)

The spectrum data of the lower polarity component accorded with those of the higher polarity component.

EXAMPLE 49

The reaction was carried out following the same procedures as in Example 48 by using {3-(4'-methoxycarbonyl-1'-butenyl)-6(S)-(3'(RS)-hydroxy-3'-cyclopentyl-trans-1'-propenyl)-7(R)-tetrahydropyranyloxy-(1S,5S)-cis-bicyclo[3.3.0]oct-2-ene} (444 mg, 1 mmol) to obtain, as a lower polarity component, {3-(4'-methoxycarbonyl-1'-butenyl)-6(S)-(3'(R)-hydroxy-3'-cyclopentyl-trans-1'-propenyl)-7(R)-hydroxy-(1S,5S)-cis-bicyclo[3.3.0]oct-2-ene} (94 mg, Yield: 26%) and, as a higher polarity component, {3-(4'-methoxycarbonyl-1'-butenyl)-6(S)-(3'(S)-hydroxy-3'-cyclopentyl-trans-1'-propenyl)-7(R)-hydroxy-(1S,5S)-cis-bicyclo[3.3.0]oct-2-ene} (198 mg, Yield: 55%), as colorless oily product, respectively.

The spectrum data of the higher polarity component were as follows:

IR (neat): 3400, 1740 cm$^{-1}$.

NMR δ (CDCl$_3$): 6.22 (d, J=15 Hz, ½H, trans), 5.95 (d, J=11 Hz, ⅔H, cis), 5.17–5.75 (m, 4H), 3.65 (s, 3H), 3.40–4.00 (m, 2H).

Mass m/z: 360, 342.

$[α]_D^{20} = -30°$ (c=1.16, MeOH)

The spectrum data of the lower polarity component accorded with those of the higher polarity component.

EXAMPLE 50

{3-(4'-Methoxycarbonyl-1'-butenyl)-6(S)-(3'(RS)-hydroxy-4'(RS)-methyl-trans-1'-octen-6'-ynyl)-7(R)-tetrahydropyranyloxy-(1S, 5S)-cis-bicyclo[3.3.0]oct-2-ene} (350 mg, 0.77 mmol) was dissolved in THF (0.6 ml). With addition of a 65% aqueous acetic acid solution (6 ml), the mixture was stirred at 50° C. for 2 hours. The resultant mixture was poured into a cooled saturated aqueous sodium hydrogencarbonate solution and the mixture was extracted with ethyl acetic acid ester. The organic layer was washed with a saturated saline solution and dried over anhydrous magnesium sulfate. The solvent was distilled out and the residue was purified through silica gel column chromatography to obtain, as a low polarity component, {3-(4'-methoxycarbonyl-1'-butenyl)-6(S)-(3'(R)-hydroxy-4'(RS)-methyl-trans-1'-octen-6'ynyl)-7(R)-hydroxy-(1S,5S)-cis-bicyclo[3.3.0]oct-2-ene} (67 mg, Yield: 23%) and, as a high polarity component, {3-(4'-methoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]-oct-2-ene} (143 mg, Yield: 50%), as colorless oily products, respectively.

Spectrum data of the higher polarity component were as follows:

IR (neat): 3400, 1740 cm$^{-1}$.

NMR δ (CDCl$_3$): 6.25, 6.00 (each d, J=16 Hz, J=12 Hz, 1H) 5.00–5.70 (m, 3H), 3.68 (s, 3H), 1.78 (t, J=2 Hz, 3H), 0.98 (m, 3H).

Mass m/z: 372, 354, 336.

$[α]_D^{20} = -16°$ (c=1.86 MEOH)

The spectrum data of the lower polarity component accorded with those of the higher polarity component.

EXAMPLE 51

The reaction was carried out following the same procedures as in Example 50 by using {3-(4'-methoxycarbonyl-1'-butenyl)-6(S)-(3'(RS)-hydroxy-5'(R)-methyl-9'-methyltrans-1'-decene-8'-enyl)-7(R)-tetra-hydropyranyloxy(1S,5S)-cis-bicyclo[3.3.0]oct-2-ene} (350 mg, 0.70 mmol) to obtain, as a lower polarity component, {3-(4'-methoxycarbonyl-1'-butenyl)-6(S)-(3'(R)-hydroxy-5'(R)-methyl-9'-methyl-trans-1'-decene-8'-enyl)-7(R)-hydroxy-(1S,5S)-cis-bicyclo[3.3.0]oct-2-ene} (99 mg, Yield: 34%) and, as a higher polarity component, {3-(4'-methoxy-carbonyl-1'-butenyl)-6(S)-(3'(S)-hydroxy-5'(R)-methyl-9'-methyl-trans-1'-decene-8'-enyl)-7(R)-hydroxy-(1S,5S)-cis-bicyclo[3.3.0]oct-2-ene} (126 mg, Yield: 43%), as nearly colorless oily product, respectively.

The spectrum data of the higher polarity component were as follows:

IR (neat): 3400, 1740 cm$^{-1}$.

NMR $\delta$ (CDCl$_3$) 6.25, 6.00 (each d, J=15 Hz, J=12 Hz, 1H), 5.10–5.80 (m, 5H), 3.70 (s, 3H), 1.70 (s, 3H), 1.62 (s, 3H), 0.95 (d, J=6 Hz, 3H).

Mass m/z: 416, 398, 380.

$[\alpha]_D^{20} = -31°$ (c=2.29, MeOH)

The spectrum data of the lower polarity component accorded with those of the higher polarity component.

EXAMPLE 52

The reaction was carried out following the same procedures as in Example 50 by using {3-(4'-ethoxycarbonyl-1'-butenyl)-6(S)-(3'(RS)-hydroxy-5'(R)-methyl-9'-methyl-trans-1'-decene-8'-enyl)-7(R)-tetrahydropyranyloxy-(1S, 5S)-cis-bicyclo[3.3.0]oct-2-ene} (504 mg, 0.98 mmol) to obtain, as a lower polarity component, {3-(4'-ethoxycarbonyl-1'-butenyl)-6(S)-(3'(R)-hydroxy-5'(R)-methyl-9'-methyl-trans-1'-decene-8'-enyl)-7(R)-hydroxy-(1S,5S)-cis-bicyclo[3.3.0]oct-2-ene} (139 mg, Yield: 33%) and, as a higher polarity component, {3-(4'-ethoxycarbonyl-1'-butenyl)-6(S)-(3'(S)-hydroxy-5'(R)-methyl-9'-methyl-trans-1'-decene-8'-enyl)-7(R)-hydroxy-(1S,5S)-cis-bicyclo[3.3.0]oct-2-ene} (194 mg, Yield: 46%), as colorless oily products, respectively.

Spectrum data of the higher polarity component were as follows:

IR (neat): 3400, 1740 cm$^{-1}$.

NMR $\delta$ (CDCl$_3$) 6.25, 6.00 (each d, J=15 Hz, J=12 Hz, 1H), 5.10–5.80 (m, 5H), 4.20 (q, J=7 Hz, 2H), 1.70 (s, 3H), 1.62 (s, 3H), 1.30 (t, J=7 Hz, 3H), 0.95 (d, J=6 Hz, 3H).

Mass m/z: 430, 412, 394.

EXAMPLE 53

The reaction was carried out following the same procedures as in Example 48 by using {3-(4'-ethoxycarbonyl-1'-butenyl)-6(S)-(3'(RS)-hydroxy-3'-cyclopentyl-trans-1'-propenyl)-7(R)-tetrahydropyranyloxy-(1S,5S)-cis-bicyclo[3.3.0]oct-2-ene} (458 mg, 1 mmol) to obtain, as a lower polarity component, {3-(4'-ethoxycarbonyl-1'-butenyl)-6(S)-(3'(R)-hydroxy-3'-cyclopentyl-trans-1'-propenyl)-7(R)-hydroxy-(1S,5S)-cis-bicyclo[3.3.0]oct-2-ene} (75 mg, Yield: 20%) and, as a higher polarity component, {3-(4'-ethoxycarbonyl-1'-butenyl)-6(S)-(3'(S)-hydroxy-3'-cyclopentyl-trans-1'-propenyl)-7(R)-hydroxy-(1S,5S)-cis-bicyclo[3.3.0]oct-2-ene} (199 mg, Yield: 53%), as colorless and viscous oily products, respectively.

The spectrum data of the higher polarity component were as follows:

IR (neat): 3400, 1740 cm$^{-1}$.

NMR $\delta$ (CDCl$_3$): 6.22 (d, J=15 Hz, ½H, trans), 5.95 (d, J=11 Hz, ⅜H, cis), 5.17–5.75 (m, 4H), 4.20 (q, J=7 Hz, 2H), 3.40–4.00 (m, 2H), 1.30 (t, J=7 Hz, 3H).

Mass m/z: 374, 356.

The spectrum data of the lower polarity component accorded with those of the higher polarity component.

EXAMPLE 54

The reaction was carried out following the same procedure as in Example 48 by using {3-(4'-ethoxycarbonyl-1'-butenyl)-6(S)-(3'(RS)-hydroxy-4'(RS)-methyl-trans-1'-octen-6'-ynyl)-7(R)-tetrahydropyranyloxy-(1S,5S)-cis-bicyclo[3.3.0]oct-2-ene} (470 mg, 1 mmol) to obtain, as a lower polarity component, {3-(4'-ethoxycarbonyl-1'-butenyl)-6(S)-(3'(R)-hydroxy-4'(RS)-methyl-trans-1'-octen-6'-ynyl)-7(R)-hydroxy-(1S,5S)-cis-bicyclo-[3.3.0]oct-2-ene} (81 mg, Yield: 21%) and, as a higher polarity component, {3-(4'-ethoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (201 mg, Yield: 52%), as colorless oily products, respectively.

The spectrum data of the higher polarity component were as follows:

IR (neat): 3400, 1740 cm$^{-1}$.

NMR $\delta$ (CDCl$_3$): 6.22 (d, J=15 Hz, ½H, trans), 5.95 (d, J=11 Hz, ⅜H, cis), 5.17–5.75 (m, 4H), 4.20 (q, J=7 Hz, 2H), 3.40–4.00 (m, 2H), 1.75 (t, J=2 Hz, 3H), 1.30 (t, J=7 Hz, 3H), 1.20 (d, J=7 Hz, 3H).

Mass m/z: 386, 368.

The spectrum data of the lower polarity component accorded with those of the higher polarity component.

EXAMPLE 55

{3-(4'-Methoxycarbonyl-1'-butenyl)-6(S)-(3'(S)-hydroxy-trans-1'-octenyl)-7(R)-hydroxy-(1S,5S)-cis-bicyclo[3.3.0]oct-2-ene} (362 mg, 1 mmol) was dissolved in DMF (1.5 ml). With addition of imidazole (204 mg, 3 mmol) and t-butyldimethylsilyl chloride (452 mg, 3 mmol), the resultant mixture was stirred at room temperature for 10 hours. The reaction was stopped by adding a saturated aqueous ammonium chloride solution and the mixture was extracted with ether. The separated ether layer was washed with a saturated saline solution and dried with anhydrous magnesium sulfate. The solvent was distilled out and the residue was purified through silica gel column chromatography to obtain {3-(4'-methoxycarbonyl-1'-butenyl)-6(S)-(3'(S)-t-butyldimethylsilyloxy-trans-1'-octenyl)-7(R)-t-butyldimethylsilyloxy-(1S,5S)-cis-bicyclo[3.3.0]oct-2-ene} (590 mg, Yield: 100%) as nearly colorless oily product.

IR (neat): 1750, 840 cm$^{-1}$.

NMR $\delta$ (CDCl$_3$) 6.27 (d, J=16 Hz, ½H, trans), 6.02 (d, J=11 Hz, ⅜H, cis), 5.51 (m, 4H), 4.07 (m, 1H), 3.70 (m, 1H), 3.69 (s, 3H).

Mass m/z: 590, 534, 533, 519.

$[\alpha]_D^{20} = -37°$ (c=0.61, CHCl$_3$).

EXAMPLE 56

The reaction was carried out following the same procedures as in Example 55 by using {3-(4'-methoxycarbonyl- 1'-butenyl)-6(S)-(3'(S)-hydroxy-3'-cyclopentyl-trans-1'-propenyl)-7(R)-hydroxy-(1S,5S)-cisbicyclo[3.3.0]oct-2-ene} (360 mg, 1 mmol) to obtain {3-(4'-methoxycarbonyl-1'-butenyl)-6(S)-(3'(S)-t-butyldimethylsilyloxy-3'-cyclopentyl-trans-1'-propenyl)-7(R)-t-butyldimethylsilyloxy-(1S,5S)-cis-bicyclo[3.3.0]oct-2-ene} (586 mg, Yield: 100%) as nearly colorless oily products.

IR (neat): 1745, 835 cm$^{-1}$.

NMR δ (CDCl$_3$): 6.25 (d, J=16 Hz, ⅓H, trans), 6.01 (d, J=11 Hz, ⅔H, cis), 5.50 (m, 4H), 4.07 (m, 1H), 3.69 (m, 1H), 3.68 (s, 3H).

Mass m/z: 588, 532, 531, 517.

[α]$_D^{20}$ = −37° (c=1.62, CHCl$_3$).

EXAMPLE 57

{3-(4'-Methoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (70 mg, 0.19 mmol) was dissolved in DMF (0.25 ml). With addition of t-butyldimethylsilylchloride (85 mg, 0.57 mmol) and imidazole (38 mg, 0.57 mmol), the mixture was stirred at room temperature for 2 hours. The reaction was stopped by adding a saturated aqueous ammonium chloride solution and the mixture was extracted with ether. The separated ether layer was washed with a saturated saline solution and dried with anhydrous magnesium sulfate. The solvent was distilled out and the residue was purified through silica gel column chromatography to obtain {3-(4'-methoxybonyl-1'-butenyl)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]oct-2-ene} (93 mg, Yield: 82%) as nearly colorless oily products.

IR (neat): 1745, 840 cm$^{-1}$.

NMR δ (CDCl$_3$): 6.23, 5.97 (each d, J=15 Hz, J=11 Hz, 1H), 5.05–5.70 (m, 4H,), 3.65 (s, 3H), 1.75 (t, J=2 Hz, 3H).

Mass m/z: 600, 543.

[α]$_D^{20}$ = −30° (c=1.82, CHCl$_3$).

EXAMPLE 58

The reaction was carried out following the same procedures as in Example 57 by using {3-(4'-methoxycarbonyl-o 1'-butenyl)-6(S)-(3'(S)-hydroxy-5'(R)-methyl-9'-methyl-trans-1'-decene-8'-enyl)-7(R)-hydroxy-(1S,5S)-cis-bicyclo[3.3.0]oct-2-ene} (90 mg, 0.22 mmol) to obtain (3-(4'-methoxycarbonyl-1'-butenyl)-6(S)-(3'(S)-t-butyldimethylsilyloxy-5'(R)-methyl-9'-methyl-trans-1'-decene-8'-enyl)-7(R)-t-butyldimethylsilyloxy-(1S,5S)-cis-bicyclo[3.3.0]-oct-2-ene} (108 mg, Yield: 78%) as nearly colorless oily products.

IR (neat): 1745, 835 cm$^{-1}$.

NMR δ (CDCl$_3$): 6.20, 5.95 (each d, J=15 Hz, J=11 Hz, 1H), 5.00–5.60 (m, 5H), 3.68 (s, 3H), 1.66 (s, 3H), 1.60 (s, 3H).

Mass m/z: 644, 587, 519.

[α]$_D^{20}$ = −45° (c=2.18, CHCl$_3$).

EXAMPLE 59

The reaction was carried out following the same procedures as in Example 57 by using {3-(4'-ethoxycarbonyl-1'-butenyl)-6(S)-(3'(S)-hydroxy-5'(R)-methyl-9'-methyl-trans-1'-decene-8'-enyl)-7(R)-hydroxy-(1S,5S)-cis-bicyclo-[3.3.0]-oct-2-ene} (95 mg, 0.22 mmol) to obtain {3-(4'-ethoxycarbonyl-1'-butenyl)-6(S)-(3'(S)-t-butyldimethylsilyloxy-5'(R)-methyl-9'-methyl-trans-1'-decene-8'-enyl)- 7(R)-t-butyldimethylsilyloxy-(1S,5S)-cis-bicyclo[3.3.0]-oct-2-ene} (145 mg, Yield: 100%) as nearly colorless oily products.

IR (neat): 1743 cm$^{-1}$.

NMR δ (CDCl$_3$): 6.20, 5.95 (each d, J=15 Hz, J=11 Hz, 1H), 5.00–5.60 (m, 5H), 4.20 (q, J=7 Hz, 2H), 1.66 (s, 3H), 1.60 (s, 3H), 1.30 (t, J=7 Hz, 3H).

Mass m/z: 658, 601, 533.

EXAMPLE 60

The reaction was carried out following the same procedures as in Example 55 by using {3-(4'-ethoxycarbonyl-1'-butenyl)-6(S)-(3'(S)-hydroxy-3'-cyclopentyl-trans-1'-propenyl)-7(R)-hydroxy(1S,5S)-cis-bicyclo[3.3.0]oct-2-ene} (187 mg, 0.5 mmol) to obtain {3-(4'-ethoxycarbonyl-1'-butenyl)-6(S)-(3'(S)-t-butyldimethylsilyloxy-3'-cyclo-pentyl-trans-1'-propenyl)-7(R)-t-butyldimethylsilyloxy-(1S, 5S)-cis-bicyclo[3.3.0]oct-2-ene} (286 mg, Yield: 95%) as colorless oily products.

IR (neat): 1745 cm$^{-1}$.

NMR δ (CDCl$_3$): 6.25 (d, J=16 Hz, ⅓H, trans), 6.01 (d, J=11 Hz, ⅔H, cis), 5.50 (m, 4H), 4.20 (q, J=7 Hz, 2H), 4.07 (m, 1H), 3.69 (m, 1H), 1.30 (t, J=7 Hz, 3H).

Mass m/z: 602, 545.

EXAMPLE 61

The reaction was carried out following the same procedures as in Example 55 by using {3-(4'-ethoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (193 mg, 0.5 mmol) to obtain (3-(4'-ethoxycarbonyl-1'-butenyl)-6(S)-(3'(S)-t-butyldimethylsilyloxy- 4'(RS)-methyl-trans-1'-octen-6'-ynyl)-7(R)-t-butyl-dimethylsilyloxy-(1S,5S)-cis-bicyclo[3.3.0]oct-2-ene) (300 mg, Yield: 100%) as nearly colorless oily products.

IR (neat): 1745 cm$^{-1}$.

NMR δ (CDCl$_3$): 6.25 (d, J=16 Hz, ⅓H, trans), 6.01 (d, J=11 Hz, ⅔H, cis), 5.50 (m, 4H), 4.20 (q, J=7 Hz, 2H), 4.07 (m, 1H), 3.69 (m, 1H), 1.75 (t, J=2 Hz, 3H), 1.30 (t, J=7 Hz, 3H), 1.20 (d, J=7 Hz, 3H).

Mass m/z: 614, 557.

EXAMPLE 62

{3-(4'-Methoxycarbonyl-1'-butenyl)-6(S)-(3'(S)-hydroxytrans-1'-octenyl)-7(R)-hydroxy-(1S,5S)-cis-bicyclo-[3.3.0]oct-2-ene} (362 mg, 1 mmol) was dissolved in methylene chloride (3.6 ml). Dihydropyrane (840 mg, 10 mmol) was added to the resultant solution and catalytic amount of p-toluenesulfonic acid was further added to the mixture, followed by stirring at room temperature for 10 minutes. The reaction was stopped by addition of a saturated aqueous sodium hydrogencarbonate solution and the mixture was extracted with ether. The separated ether layer was washed with a saturated saline solution, followed by dryness with anhydrous magnesium sulfate. After the solvent was distilled out, the residue was purified through silica gel column chromatography to obtain {3-(4'-methoxycarbonyl-1'-butenyl)-6(S)-(3'(S)-tetrahydropyranyloxy-trans-1'-octenyl)-7(R)-tetrahydropyranyloxy-(1S,5S)-cis-bicyclo[3.3.0]oct-2-ene} (477 mg, Yield: 90%) as neary colorless oily products.

IR (neat): 1745 cm$^{-1}$.

NMR δ (CDCl$_3$): 6.25 (d, J=16 Hz, ⅓H, trans), 6.02 (d, J=11 Hz, ⅔H, cis), 5.50 (m, 4H), 4.60 (m, 2H), 4.05 (m, 1H), 3.69 (s, 3H), 3.40–4.00 (m, 5H).

Mass m/z: 530, 446.

EXAMPLE 63

The reaction was carried out following the same procedures as in Example 62 by using {3-(4'-methoxycarbonyl-1'-butenyl)-6(S)-(3'(S)-hydroxy-3'-cyclopentyl-trans-1'-propenyl)-7(R)-hydroxy-(1S,5S)-cis-bicyclo[3.3.0]oct-2-ene} (360 mg, 1 mmol) to obtain (3-(4'-methoxycarbonyl-1'-butenyl)-6(S)-(3'(S)-tetrahydropyranyloxy-3'-cyclo-pentyl-trans-1'-propenyl)-7(R)-tetrahydropyranyloxy-(1S,5S)-cis-bicyclo[3.3.0]oct-2-ene} (475 mg, Yield: 90%) as colorless oily products.

IR (neat): 1745 cm$^{-1}$.

NMR δ (CDCl$_3$): 6.23 (d, J=16 Hz, ⅓H, trans), 6.03 (d, J=11 Hz, ⅔H, cis), 5.50 (m, 4H), 4.60 (m, 2H), 4.05 (m, 1H), 3.68 (s, 3H), 3.40–4.00 (m, 5H).

Mass m/z: 528, 444.

EXAMPLE 64

{3-(4'-Methoxycarbonyl-1'-butenyl)-6(S)-(3'(S)-hydroxy-4'(RS)-methyl-trans-1'-octen-6'-ynyl)-7(R)-hydroxy-(1S, 5S)-cis-bicyclo[3.3.0]oct-2-ene} (186 mg, 0.5 mmol) was dissolved in methylene chloride (1.86 ml). Dihydropyrane (420 mg, 5 mmol) was added to the resultant solution and catalytic amount of p-toluenesulfonic acid was further added to the mixture, followed by stirring at room temperature for 10 minutes. The reaction was stopped by addition of a saturated aqueous sodium hydrogencarbonate solution and the mixture was extracted with ether. The separated ether layer was washed with a saturated saline solution, followed by dryness with anhydrous magnesium sulfate. After the solvent was distilled out, the residue was purified through silica gel column chromatography to obtain {3-(4'-methoxycarbonyl-1'-butenyl)-6(S)-(3'(S)-tetrahydropyranyloxy-4'(RS)-methyl-trans-1'-octen-6'-ynyl)-7(R)-tetrahydropyranyloxy-( 1S,5S)-cis-bicyclo[3.3.0]oct-2-ene} (256 mg, Yield: 95%) as neary colorless oily products.

IR (neat): 1743 cm$^{-1}$.

NMR δ (CDCl$_3$): 6.23 (d, J=16 Hz, ⅓H, trans), 6.03, (d, J=11 Hz, ⅔H, cis), 5.50 (m, 4H), 4.60 (m, 2H), 4.05 (m, 1H), 3.67 (s, 3H), 3.40–4.00 (m, 5H), 1.75 (t, J=2 Hz, 3H), 1.20 (d, J=7 Hz, 3H).

Mass m/z: 538, 454.

EXAMPLE 65

The reaction was carried out following the same procedures as in Example 64 by using {3-(4'-methoxycarbonyl-1'-butenyl)-6(S)-(3'(S)-hydroxy-5'(R)-methyl-9'-methyl-trans-1'-decene-8'-enyl)-7(R)-hydroxy-(1S,5S)-cis-bicyclo[3.3.0]oct-2-ene} (208 mg, 0.5 mmol) to obtain {3-(4'-methoxycarbonyl-1'-butenyl)-6(S)-(3'(S)-tetrahydropyranyl-oxy-5'(R)-methll-9'-methyl-trans-1'-decene-8'-enyl)-7(R)-tetrahydropyranyloxy-(1S,5S)-cis-bicyclo[3.3.0]oct-2-ene} (274 mg, Yield: 94%) as nearly colorless oily products.

IR (neat): 1745 cm$^{-1}$.

NMR δ (CDCl$_3$): 6.26, 6.00 (each d, J=15 Hz, J=11 Hz, 1H), 5.00–5.62 (m, 5H), 4.65 (2H, m), 3.70 (s, 3H), 0.93 (d, J=6 Hz, 3H).

Mass m/z: 582, 498.

EXAMPLE 66

{3-(4'-Methoxycarbony-1'-butenyl)-6(S)-(3'(S)-hydroxy-4'(RS)-methyl-trans-1'-octen-6'-ynyl)-7(R)-hydroxy-(1S, 5S)-cis-bicyclo[3.3.0]oct-2-ene} (54 mg, 0.145 mmol) was dissolved in methanol (1.16 ml). A 10% aqueous sodium hydroxide solution (1.16 ml) was added to the thus prepared mixture at 0° C., followed by stirring at 0° C. for 8 hours. The reaction mixture was diluted with ether, followed by neutrization with a 10% aqueous hydrochloric acid solution under ice-cooling. Then, methanol was distilled out under reduced pressure. The resultant aqueous layer was adjusted to pH 3 to 4 and extracted with ethyl acetate. After the separated ether layer was dried with anhydrous magensium sulfate, the solvent was distilled out to obtain {3-(4'-carboxy-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]-oct-2-ene} (50 mg, Yield: 96%).

IR (neat): 3350, 2950, 1715 cm$^{-1}$.

NMR δ (CDCl$_3$) 6.32 (d, J=16 Hz, ⅓H, trans), 6.04 (d, J=11 Hz, ⅔H, cis), 5.20–5.90 (m, 4H), 1.81(t, J=2 Hz, 3H), 1.00 (m, 3H).

EXAMPLE 67

{3-(4'-Methoxycarbony-1'-butenyl)-6(S)-(3'(S)-hydroxy-5'(R)-methyl-9'-methyl-trans-1'-decene-8'-enyl)-7(R)-hydroxy-(1S,5S)-cis-bicyclo[3.3.0]octene} (40 mg, 0.086 mmol) was dissolved in methanol (0.69 ml). A 10% aqueous sodium hydroxide solution (1.16 ml) was added to the thus prepared solution at 0° C., followed by stirring at 0° C. for 8 hours. The resultant mixture was diluted with ether, and neutralized with a 10% aqueous hydrochloric acid solution under ice-cooling. After methanol was distilled out under reduced pressure, the resultant aqueous layer was adjusted to pH 3 to 4 and extracted with ethyl acetate. The separated organic layer was dried with anhydrous magnesium sulfate and the solvent was distilled out to obtain {3-(4'-carboxy-1'-butenyl)-6(S)-(3'(S)-hydroxy-5'(R)-methyl-9'-methyl-trans-1'-decene-8'-enyl)-7(R)-hydroxy-(1S,5S)-cis-bicyclo[3.3.0]-oct-2-ene} (37 mg, Yield: 95%).

IR (neat): 3350, 2950, 1715 cm$^{-1}$.

NMR δ (CDCl$_3$) 6.30 (d, J=16 Hz, ⅓H, trans) 6.02 (d, J=11 Hz, ⅔H, cis), 5.28–5.75 (m, 4H), 5.12 (t, J=7 Hz, 1H), 1.61 (s, 3H), 1.68 (s, 3H), 0.93 (d, J=6 Hz, 3H).

REFERENCE EXAMPLE 41

{3-(4'-Methoxycarbonyl-1'-butenyl)-6(S)-(3'(S)-t-butyl-dimethylsilyloxy-3'-cyclopentyl-trans-1'-propenyl-7(R)-t-butyldimethylsilyloxy-(1S,5S)-cis-bicyclo[3.3.0]oct-2-ene} (cis:trans=2:1 mixture; 105 mg, 0.18 mmol) and methylbezoatetricarbonylchromium (9 mg, 0.03 mmol) were dissolved in acetone (10 ml), and degassed. In autoclave under 70 Kg/cm$^2$ of hydrogen gas pressure, the reaction was carried out at 120° C. for 15 hours. The solvent was distilled out and the residue was purified through silica gel column chromatograpy to obtain {3(E)-(4'-methoxycarbonylbutylidene)-6(S)-(3'(S)-t-butyl-dimethylsilyloxy-3'-cyclopentyl-trans-1'-propenyl)-7(R)-t-butyldimethylsilyloxy-(1S,5S)-cis-bicyclo[3.3.0]octane} (105 mg, Yield: 100%) as nearly colorless oily products.

IR (neat): 1745 cm$^{-1}$.

NMR δ (CDCl$_3$): 5.50 (m, 2H), 5.23 (t, J=7 Hz, 1H), 3.68 (s, 3H), 3.50–,4.00 (m, 2H).

Mass m/z: 533, 521.

Results are summarized in the following Table 6 in which solvents and catalysts other than the above-mentioned were used.

TABLE 6

| Solvent | Catalyst | Amount of catalyst (wt. %) | Hydrogen pressure (Kg/cm²) | Temperature (°C.) | Reaction time (hour) | Yield (%) |
|---|---|---|---|---|---|---|
| acetone | toluene-tricarbonyl-chromium | 20 | 70 | 130 | 13 | 82* |
| acetonitrile | methylbezoatetricarbonylchromium | 20 | 70 | 130 | 12 | 21* |
| acetone | mesitylene-tricarbonyl-molybdenum | 20 | 70 | 100 | 12 | 52* |
| acetone | mesitylene-tricarbonyl-tungsten | 20 | 70 | 120 | 12 | 12* |
| acetone | triphenyl-phosphin-pentacarbonyl-chromium | 20 | 70 | 180 | 15 | 9* |
| acetone | Hydridecyclo-pentadienyl-tricarbonyl-chromium | 10 | 90 | 100 | 15 | 50* |

*Selectivity coefficient of E-Isomer was 100%.

REFERENCE EXAMPLE 42

The reaction was carried out following the same procedures as in Reference example 41 by using (3-(4′-methoxycarbonyl-1′-butenyl)-6(S)-(3′(S)-tetrahydropyranyloxy-3′-cyclopentyl-trans-1′-propenyl-7(R)-tetrahydropyranyloxymixture; (1S,5S)-cis-bicyclo[3.3.-0]oct-2-ene} (cis:trans=2:1 mixture; 111 mg, 0.21 mmol) to obtain (3(E)-(4′-methoxycarbonylbutylidene)-6(S)-(3′(S)-tetrahydropyranyloxy-{3′-cyclopentyl-trans-1′-propenyl)-7(R)-tetrahydropyranyloxy-(1S,5S)-cis-bicyclo[3.3.0]octane} (100 mg, Yield: 90 %) as nearly colorless oily product.

IR (neat): 1744 cm⁻¹.

NMRδ (CDCl₃): 5.48 (m, 2H), 5.23 (t, J=7 Hz, 1H), 4.60 (m, 2H), 3.68 (s, 3H), 3.40–4.00 (m, 6H).

Mass m/z: 530, 461, 446.

REFERENCE EXAMPLE 43

{3-(4′-Methoxycarbonyl-1′-butenyl)-6(S)-(3′(S)-t-butyl-dimethylsilyloxy-trans-1′-octenyl-7(R)-t-butyl-dimethylsilyloxy-(1S,5S)-cis-bicyclo[3.3.0]-oct-2-ene} (cis:trans=2:1 mixture; 107 mg, 0.18 mmol) and methylbezoatetricarbonylchromium (9 mg, 0.03 mmol) were dissolved in acetone (10 ml), and degassed. In autoclave under 70 Kg/cm² of hydrogen gas pressure, the reaction was carried out at 120° C. for 15 hours. The solvent was distilled out and the residue was purified through silica gel column chromatography to obtain {3(E)-(4′-methoxycarbonylbutylidene)-6(S)-(3′(S)-t-butyldimethylsilyloxy-trans-1′-octenyl)-7(R)-t-butyldimethylsilyloxy-(1S,5S)-cis-bicyclo[3.3.0]octane} (107 mg, 100%) as nearly colorless oily products.

IR (neat): 1745 cm⁻¹.

NMRδ (CDCl₃): 5.50 (m, 2H), 5.23 (t, J=7 Hz, 1H), 3.68 (s, 3H), 3.50–4.00 (m, 2H).

Mass m/z: 535.

REFERENCE EXAMPLE 44

The reaction was carried out following the same procedures as in Reference example 43 by using {3-(4′-methoxycarbonyl-1′-butenyl)-6(S)-(3′(S)-tetrahydropyranyloxy-trans-1′-octenyl)-7(R)-tetrahydropyranyloxy-(1S,5S)-cisbbicyclo[3.3.0]oct-2-ene} (cis:trans=2:1 mixture; 112 mg, 0.21 mmol) to obtain (3(E)-(4′-methoxycarbonylbutylidene)-6(S)-(3′(S)-tetrahydropyranyloxy-trans-1′-octenyl)-7(R)-tetrahydropyranyloxy-(1S,5S)-cis-bicyclo-[3.3.0]octane} (101 mg, Yield: 90%) as nearly colorless oil products.

IR (net): 1744 cm⁻¹.

NMR δ (CDCl₃): 5.48 (m, 2H), 5.23 (t, J=7 Hz, 1H), 4.60 (m, 2H), 3.68 (s, 3H), 3.40–4.00 (m, 6H).

Mass m/z: 532, 448.

REFERENCE EXAMPLE 45

(3-(4′-Ethoxycarbonyl-1′-butenyl)-6(S)-(3′(S)-t-butyl-dimethylsilyloxy-3′-cyclopentyl-trans-1′-propenyl-7(R)-t-butyldimethylsilyloxy-(1S,5S)-cis-bicyclo[3.3.-0]oct-2-ene} (cis:trans=2:1 mixture; 108 mg, 0.18 mmol) and methylbezoatetricarbonylchromium (9 mg, 0.03 mmol) were dissolved in acetone (10 ml), and degassed. In autoclave under 70 Kg/cm² of hydrogen pressure, the reaction was carried out at 120° C. for 15 hours. The solvent was distilled out and the residue was purified through silica gel column chromatography to obtain (3(E)-(4′-ethoxycarbonylbutylidene)-6(S)-(3′(S)-t-butyldimethylsilyloxy-3′-cyclopentyl-trans-1′-propenyl)-7(R)-t-butyldimethyl-silyloxy-(1S,5S)-cis-bicyclo[3.3.0]octane) (108 mg, Yield: 100%) as nearly colorless oily product.

IR (neat): 1745 cm⁻¹.

NMR δ (CDCl₃): 5.50 (m, 2H), 5.23 (t, J=7 Hz, 1H), 4.20 (q, J=7 Hz, 2H), 3.50–4.00 (m, 2H), 1.30 (t, J=7 Hz, 3H).

Mass m/z: 604, 547, 535.

REFERENCE EXAMPLE 46

{3-(4′-Methoxycarbonyl-1′-butenyl)-6(S)-(3′(S)-t-butyldimethylsilyloxy-5′(R)-methyl-9′-methyl-trans-1′-decene-8′-enyl)-7(R)-t-butyldimethylsilyloxy-(1S,5S)-cis-bicyclo[3.3.0]-oct-2-ene) (cis:trans=2:1 mixture; 116 mg, 0.18 mmol) and methylbezoatetricarbonylchromium (9 mg, 0.03 mmol) were dissolved in acetone (10 ml), and degassed. In autoclave under 70 Kg/cm² of hydrogen pressure, the reaction was carried out at 120° C. for 15 hours. The solvent was distilled out and the residue was purified through silica gel column chromatography to obtain (3(E)-(4′-methoxycarbonylbutylidene)-6(S)-(3′(S)-t-butyldimethylsilyloxy-5′(R)-methyl-9′-methyl-trans-1′-decene-8′-enyl)-7(R)-t-butyldimethylsilyloxy-(1S,5S)-cis-bicyclo[3.3.0]octane) (105 mg, Yield: 90%) as nearly colorless oily product.

IR (neat): 1745 cm$^{-1}$.

NMR (CDCl$_3$): 5.50 (m, 2H), 5.18 (m, 2H), 3.70 (s, 3H), 1.74 (s, 3H), 1.62 (s, 3H).

Mass m/z: 646, 589.

REFERENCE EXAMPLE 47

The reaction was carried out following the same procedures as in Reference example 46 by using (3-(4'-etoxycarbonyl-1'-butenyl)-6(S)-(3'(S)-t-butyldimethylsilyloxy-5'(R)-methyl-9'-methyl-trans-1'-decene-8'-enyl)-7(R)-t-butyldimethylsilyloxy-(1S,5S)-cis-bicyclo[3.3.0]oct-2-ene} (cis:trans=2:1 mixture; 118 mg, 0.18 mmol) to obtain {3(E)-(4'-ethoxycarbonylbutylidene)-6(S)-(3'(S)-t-butyldimethylsilyloxy-5'(R)-methyl-9'-methyl-trans-1'-decene-8'-enyl)-7(R)-t-butyldimethylsilyloxy-(1S,5S)-cis-bicyclo[3.3.0]octane} (107 mg, Yield: 90%) as nearly colorless oily product.

IR (neat): 1745 cm$^{-1}$.

NMR δ (CDCl$_3$): 5.50 (m, 2H), 5.23 (m, 2H), 4.20 (q, J=7 Hz, 2H), 1.70 (s, 3H), 1.62 (s, 3H), 1.30 (t, J=7 Hz, 3H).

Mass m/z: 660, 503.

REFERENCE EXAMPLE 48

The reaction was carried out following the same procedures as in Reference example 6 by using (3-(4'-methoxy-1'-butenyl)-6(S)-(3'(S)-tetrahydropyranyloxycarbonyl 5'(R)-methyl-9'-methyl-trans-1'-decene-8'-enyl)-7(R)-tetrahydropyranyloxy-(1S,5S)-cis-bicyclo-[3.3.0]-oct-2-ene} (cis:trans=2:1 mixture; 105 mg, 0.18 mmol) to obtain {3(E)-(4'-methoxycarbonylbutylidene)-6(S)-(3'(S)-tetrahydropyranyloxy-5'(R)-methyl-9'-methyl-trans-1'-decene-8'-enyl)-7(R)-tetrahydropyranyloxy-(1S,5S)-cis-bicyclo[3.3.0]octane} (89 mg, Yield: 85%) as nearly colorless oil product.

IR (neat): 1743 cm$^{-1}$.

NMRδ (CDCl$_3$): 5.50 (m, 2H), 5.21 (m, 2H), 4.60 (m, 2H), 3.66 (s, 3H), 3.30–4.10 (m, 6H), 0.93 (d, J=6 Hz, 3H).

Mass m/z: 584, 500.

REFERENCE EXAMPLE 49

{3-(4'-Methoxycarbonyl-1'-butenyl)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0] -oct-2-ene) (cis:trans=2:1 mixture; 92 mg, 0.16 mmol) and methylbezoatetricarbonylchromium (9 mg, 0.03 mmol) were dissolved in acetone (10 ml), and degassed. In autoclave under 70 Kg/cm$^2$ of hydrogen gas pressure, the reaction was carried out at 120° C. for 15 hours. The solvent was distilled out and the residue was purified through silica gel column chromatography to obtain {3(E)-(4'-methoxycarbonylbutylidene)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]-octane} (38 mg, Yield: 41%) as nearly colorless oily product.

IR (neat): 1745 cm$^{-1}$.

NMRδ (CDCl$_3$): 5.45 (m, 2H), 5.20 (t, J=7 Hz, 1H), 3.62 (s, 3H), 1.74 (t, J=2 Hz, 3H).

Mass m/z: 602, 545.

Results are summarized in the following Table 7 in which solvents and catalysts other than the above-mentioned were used.

TABLE 7

| Solvent | Catalyst | Amount of catalyst (wt. %) | Hydrogen pressure (Kg/cm$^2$) | Temperature (°C.) | Reaction time (hour) | Yield (%) |
|---|---|---|---|---|---|---|
| acetone | toluenetricarbonylchromium | 20 | 70 | 130 | 13 | 31* |
| acetonitrile | methylbezoatetricarbonylchromium | 20 | 70 | 130 | 12 | 5* |
| acetone | mesitylenetricarbonylmolybdenum | 20 | 70 | 100 | 12 | 26* |
| acetone | mesitylenetricarbonyltungsten | 20 | 70 | 120 | 12 | 5* |
| acetone | triphenylphosphinpentacarbonylchromium | 20 | 70 | 180 | 15 | 4* |
| acetone | Hydridecyclopentadienyltricarbonylchromium | 10 | 90 | 100 | 15 | 21* |

*Selectivity coefficient of E-Isomer was 100%.

REFERENCE EXAMPLE 50

The reaction was carried out following the same procedures as in Reference example 49 by using {3-(4'-methoxycarbonyl-1'-butenyl)-6(S)-(3'(S)-tetrahydropyranyloxy-4'(RS)-methyl-trans-1'-octen-6'-ynyl)-7(R)-tetrahydropyranyloxy-(1S,5S)-cis-bicyclo[3.3.-0]oct-2-ene} (cis:trans=2:1 mixture; 86 mg, 0.16 mmol) to obtain {3(E)-(4'-methoxycarbonylbutylidene)-6(S)-(3'(S)-tetrahydropyranyloxy-4'(RS)-methyl-trans-1'-octen-6'-ynyl)-7(R)-tetrahydropyranyloxy-(1S,5S)-cis-bicyclo[3.3.0]octane} (26 mg, Yield: 30%) as nearly colorless oily product.

IR (neat): 1745 cm$^{-1}$.

NMRδ (CDCl$_3$) 5.48 (m, 2H), 5.23 (t, J=7 Hz, 1H), 4.60 (m, 2H), 3.70 (s, 3H), 1.75 (t, J=2 Hz, 3H).

Mass m/z: 540, 456.

REFERENCE EXAMPLE 51

The reaction was carried out following the same procedures as in Reference example 49 by using {3-(4'-ethoxycarbonyl-1'-butenyl)-6(S)-(3'(S)-butyldimethylsilyloxy-4'(RS)-methyl-trans-1'-octen-6'-ynyl)-7(R)-t-butyldimethylsilyloxy-(1S,5S)-cis-bicyclo[3.3.-

0]oct-2-ene} (cis:trans=2:1 mixture; 98 mg, 0.16 mmol) to obtain {3(E)-(4'-ethoxycarbonylbutylidene)-6(S)-(3'(S)-t-butyldimethylsylyloxy-4'(RS)-methyl-trans-1'-octen-6'-ynyl)-7(R)-t-butyldimethysylyloxy-(1S,5S)-cis-bicyclo[3.3.0]-octane} (39 mg, Yield: 40%) as nearly colorless oily product.

IR (neat): 1745 cm$^{-1}$.

NMR$\delta$ (CDCl$_3$) 5.48 (m, 2H), 5.23 (t, J=7 Hz, 1H), 4.20 (q, J=7 Hz, 2H), 1.75 (t, J=2 Hz, 3H), 1.30 (t, J=7 Hz, 3H).

Mass m/z: 616, 559.

REFERENCE EXAMPLE 52

The reaction was carried out following the same procedures as in Reference example 49 by using {3-(4'-carboxy-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (cis:trans=2:1 mixture; 36 mg, 0.100 mmol) to obtain {3(E)-(4'-carboxybutylidene)-6(S)-(3'(S)-hydroxy-4'(RS)-methyl-trans-1'-octen-6'-ynyl)-7(R)-hydroxy-(1S,5S)-cis-bicyclo[3.3.0]octane} (6 mg, Yield: 18%) as viscous colorless oily products.

IR (neat): 3350, 1710 cm$^{-1}$.

NMR $\delta$ (CDCl$_3$): 5.47 (m, 2H), 5.18 (t, J=7 Hz, 1H), 3.50–4.09 (m, 2H), 1.78 (m, 3 H), 0.94 and 1.02 (d, J=6.5 Hz, 3H).

Mass m/z: 360, 342, 324.

The thus obtained product agreed with useful carbacyclin analogs disclosed in "Angew. Chem. Int. Ed. Engl., 20, 1046 (1981)" by H. Vorbruggen et al.

REFERENCE EXAMPLE 53

The reaction was carried out following the same procedures as in Reference example 46 by using {3-(4'-carboxy-1'-butenyl)-6(S)-(3'(S)-hydroxy-5'(R)-methyl-9'-methyltrans-1'-decene-8'-enyl)-7(R)-hydroxy-(1S,5S)-cis-bicyclo[3.3.0]oct-2-ene} (20 mg, 0.05 mmol) (cis:trans=2:1 mixture) to obtain {3(E)-(4'-carboxybutylidene)-6(S)-(3'(S)-hydroxy-5'(R)-methyl-9'-methyl-trans-1'-decene-8'-enyl)-7(R)-hydroxy-(1S,5S)-cis-bicyclo[3.3.0]octane} (14 mg, Yield: 68%) as viscous colorless oily products.

IR (neat): 3400, 1710 cm$^{-1}$.

NMR$\delta$ (CDCl$_3$): 5.50 (m, 2H), 5.20–5.30 (m, 2H), 4.14 (m, 1H), 3.70 (m, 1H), 1.70 (s, 3H), 1.62 (s, 3H), 0.95 (d, J=6 Hz, 3H).

Mass m/z: 404, 386, 368.

The thus obtained product is a carbacyclin analog. The usefulness thereof was published in '83 Inflammation Seminar - Prostaglandin Program Preliminary Text, Shinsaku Kobayashi, p. 37.

REFERENCE EXAMPLE 54

(3(E)-(4'-Methoxycarbonylbutylidene)-6(S)-(3'(S)-t-butyldimethylsilyloxy-3'-cyclopentyl-trans-1'-propenyl)-7(R)-t-butyldimethylsilyloxy-(1S,5S)-cis-bicyclo[3.3.0]octane} (93 mg, 0.16 mmol) was dissolved in THF (1.5 ml). A THF solution of tetrabutylammonium fluoride (0.48 mmol, 1M THF solution) was added to the thus prepared mixture, followed by stirring at room temperature for 12 hours. A saturated saline solution was added to the mixture and the mixture was extracted with ethyl acetate. After the separated organic layer was dried with anhydrous magnesium sulfite. The solvent was distilled out and the residue was purified through silica gel column chromatography to obtain {3(E)-(4'-methoxycarbonylbutylidene)-6(S)-(3'(S)-hydroxy-3'-cyclopentyl-trans-1'-propenyl)-7(R)-hydroxy-(1S,5S)-cis-bicyclo[3.3.0]octane} (47 mg, Yield: 82%) as colorless viscous liquid. The product solidified when allowed to stand.

IR (neat): 3400, 1742 cm$^{-1}$.

NMR$\delta$ (CDCl$_3$): 5.50 (m, 2H), 5.20 (t, J=7 Hz, 1H), 3.67 (s, 3H), 3.50–3.90 (m, 2H).

Mass m/z: 344, 326.

REFERENCE EXAMPLE 55

{3(E)-(4'-Methoxycarbonylbutylidene)-6(S)-(3'(S)-tetrahydropyranyloxy-3'-cyclopentyl-trans-1'-propenyl)-7(R)-tetrahydropyranyloxy-(1S,5S)-cis-bicyclo[3.3.0]octane} (53 mg, 0.1 mmol) was dissolved in THF (0.13 ml). A 65% aqueous acetic acid solution (1.3 ml) was added to the thus prepared solution, followed by stirring at 50° C. for 2 hours. The mixture was poured into a cooled saturated aqueous sodium hydrogencarbonate solution, and the mixture was extracted with ethyl acetate. After the separated organic layer was dried with anhydrous magnesium sulfite and the solvent was distilled out, the residue was purified through silica gel column chromatography to obtain {3(E)-(4'-methoxycarbonylbutylidene)-6(S)-(3'(S)-hydroxy-3'-cyclopentyl-trans-1'-propenyl)-7(R)-hydroxy-(1S,5S)-cis-bicyclo[3.3.0]octane} (33 mg, Yield: 90%) as colorless viscous liquid. The products solidified when allowed to stand. Each spectrum data accorded completely with those obtained in Reference Example 54.

REFERENCE EXAMPLE 56

The reaction was carried out following the same procedures as in Reference example 54 by using {3(E)-(4'-methoxycarbonylbutylidene)-6(S)-(3'(S)-t-butyldimethylsilyloxy-trans-1'-octenyl)-7(R)-t-butyldimethylsilyloxy-(1S,5S)-cis-bicyclo[3.3.0]octane} to obtain {3(E)-(4'-methoxycarbonylbutylidene)-6(S)-(3'(S)-hydroxy-trans-1'-octenyl)-7(R)-hydroxy-(1S,5S)-cis-bicyclo[3.3.0]octane} (52 mg, Yield: 90%) as nearly colorless viscous oily product.

IR (neat): 3370, 1740 cm$^{-1}$.

NMR$\delta$ (CDCl$_3$): 5.49 (m, 2H), 5.23 (t, J=7 Hz, 1H), 3.66 (s, 3H), 3.55–4.05 (m, 2H).

Mass m/z: 346, 328.

The above values completely accorded with those described in the Reference (M. Hayashi, et al., Tetrahedron, 37, 4391 (1981)). In the above-mentioned reference, {3(E)-(4'-methoxycarbonylbutylidene)-6(S)-(3'(S)-hydroxy-trans-1'-octenyl)-7(R)-hydroxy-cis-bicyclo[3.3.0]octene} was led to carbacycline.

REFERENCE EXAMPLE 57

The reaction was carried out following the same procedures as in Reference example 55 by using {3(E)-4'-methoxycarbonylbutylidene)-6(S)-(3'(S)-tetrahydropyranyloxy-trans-1'-octenyl)-7(R)-tetrahydropyranyloxy-(1S,5S)-cis-bicyclo[3.3.0]octane} (54 mg, 0.1 mmol) to obtain {3(E)-(4'-methoxycarbonylbutylidene)-6(S)-(3'(S)-hydroxytrans-1'-octenyl)-7(R)-hydroxy-(1S,5S)-cis-bicyclo[3.3.0]octane} (34 mg, Yield: 90%) as nearly colorless viscous oily product. Each spectrum data completely accorded with those obtained in Reference example 56.

REFERENCE EXAMPLE 58

The reaction was carried out following the same procedures as in Refrence Example 54 by using {3(E)-(4'-ethoxycarbonylbutylidene)-6(S)-(3'(S)-t-butyldimethylsilyloxy-3'-cyclopentyl-trans-1'-propenyl)-7(R)-t-butyl-dimethylsilyloxy-(1S,5S)-cis-bicyclo[3.3.0]octane} (60mg, 0.1 mmol) to obtain {3(E)-(4'-ethoxycarbonylbutylidene)-6(S)-(3'(S)-hydroxy-3'-cyclopentyl-trans-1'-propenyl)-7(R)-hydroxy-(1S,5S)-cis-bicyclo[3.3.0]octane} (36 mg, Yield: 100%) as colorless viscous oily product. The product solidified when allowed to stand.

IR (neat): 3400, 1742 cm$^{-1}$.

NMRδ (CDCl$_3$): 5.50 (m, 2H), 5.20 (t, J=7 Hz, 1H), 4.20 (q, J=7 Hz, 2H), 3.50–3.95 (m, 2H), 1.30 (t, J=7 Hz, 3H).

Mass m/z: 358, 340.

REFERENCE EXAMPLE 59

The reaction was carried out following the same procedures as in Reference example 54 by using {3(E)-(4'-methoxycarbonylbutylidene)-6(S)-(3'(S)-t-butyldimethylsilyloxy-5'(R)-methyl-9'-methyl-trans-1'-decene-8'-enyl)-(R)-t-butyldimethylsilyloxy-(1S,5S)-cis-bicyclo[3.3.0]-octane} (103 mg, 0.16 mmol) to obtain {3(E)-(4'-methoxycarbonylbutylidene)-6(S)-(3'(S)-hydroxy-5'(R)-methyl-9'-methyl-trans-1'-decene-8'-enyl)-7(R)-hydroxy-(1S,5S)-cis-bicyclo[3.3.0]octane} (60 mg, Yield: 90%) as nearly colorless oily product.

IR (neat): 3400, 1742 cm$^{-1}$.

NMRδ (CDCl$_3$): 5.50 (m, 2H), 5.20 (m, 2H), 3.67 (s, 3H), 3.50–3.90 (m, 2H), 0.93 (d, J=6 Hz, 3H).

Mass m/z: 418, 400, 382.

REFERENCE EXAMPLE 60

The reaction was carried out following the same procedures as in Reference example 59 by using {3(E)-(4'-ethoxycarbonylbutylidene)-6(S)-(3'(S)-t-butyldimethylsilyloxy-5'(R)-methyl-9'-methyl-trans-1'-decene-8'-enyl)-7(R)-t-butyldimethylsilyloxy-(1S,5S)-cis-bicyclo[3.3.0]-octane} (66 mg, 0.1 mmol) to obtain {3(E)-(4'-ethoxycarbonylbutylidene)-6(S)-(3'(S)-hydroxy-5'(R)-methyl-9'-methyl-trans-1'-decene-8'-enyl)-7(R)-hydroxy-(1S,5S)-cis-bicyclo[3.3.0]octane} (43 mg, Yield: 100%) as nearly colorless oily products.

IR (neat): 3400, 1742 cm$^{-1}$.

NMRδ (CDCl$_3$) 5.50 (m, 2H), 5.20 (m, 2H), 4.20 (q, J=7 Hz, 2H), 3.50–3.90 (m, 2H), 1.30 (t, J=7 Hz, 3H), 0.93 (d, J=6 Hz, 3H).

Mass m/z: 430, 412, 394.

REFERENCE EXAMPLE 61

The reaction was carried out following the same procedures as in Reference example 55 by using {3(E)-(4'-methoxycarbonylbutylidene)-6(S)-(3'(S)-tetrahydropyranyloxy-5'(R)-methyl-9'-methyl-trans-1'-decene-8'-enyl)-7(R)-tetrahydropyranyloxy-(1S,5S)-cis-bicyclo[3.3.0]octane} (93 mg, 0.16 mmol) to obtain (3(E)-(4'-methoxycarbonylbutylidene)-6(S)-(3'(S)-hydroxy-5'(R)-methyl-9'-methyltrans-1'-decene-8'-enyl)-7(R)-hydroxy-(1S,5S)-cis-bicyclo[3.3.0]octane} (60 mg, Yield: 90%) as nearly colorless oily product.

Each spectrum data completely accorded with those obtained in Reference example 59.

REFERENCE EXAMPLE 62

The reaction was carried out following the same procedures as in Reference example 54 by using {3(E)-(-4'-methoxycarbonylbutylidene)-6(S)-(3'(S)-t-butyl-dimethylsilyloxy-4'(RS)-methyl-trans-1'-octen-6'-ynyl)-7(R)-t-butyldimethylsilyloxy-(1S,5S)-cis-bicyclo[3.3.0]octane} (120 mg, 2 mmol) to obtain {3(E)-(4'-methoxycarbonylbutylidene)-6(S)-(3'(S)-hydroxy-4'(RS)-methyl-trans-1'-octen-6'-ynyl)-7(R)-hydroxy-(1S,5S)-cis-bicyclo[3.3.0]-octane} (71 mg, 95%) as nearly colorless oily product.

IR (neat): 3400, 1742 cm$^{-1}$.

NMRδ (CDCl$_3$): 5.50 (m, 2H), 5.20 (t, J=7 Hz, 1H), 3.67 (s, 3H), 1.75 (t, J=2 Hz, 3H), 1.20 (d, J=7 Hz, 3H).

Mass m/z: 374, 356.

REFERENCE EXAMPLE 63

The reaction was carried out following the same procedures as in Reference example 55 by using {3(E)-(4'-methoxycarbonylbutylidene)-6(S)-(3'(S)-tetrahydropyranyloxy-4'(RS)-methyl-trans-1'-octen-6'-ynyl)-7(R)-tetrahydropyranyloxy-(1S,5S)-cis-bicyclo[3.3.-0]octane} (54 mg, 0.1 mmol) to obtain {3(E)-(4'-methoxycarbonylbutylidene)-6(S)-(3'(S)-hydroxy-4'(RS)-methyl-trans-1'-octen-6'-ynyl)-7(R)-hydroxy-(1S,5S)-cis-bicyclo[3.3.0]octane} (37 mg, Yield: 100%) as nearly colorless oily product. Each spectrum data completely accorded with those obtained in Reference example 62.

REFERENCE EXAMPLE 64

The reaction was carried out following the same procedures as in Reference example 54 by using (3-(-E)-(4'-ethoxycarbonylbutylidene)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.-0]octane} (62 mg, 0.1 mmol) to obtain (3(E)-(4'-ethoxycarbonylbutylidene)-6(S)-(3'(S)-hydroxy-4'(RS)-methyl-trans-1'-octen-6'-ynyl)-7(R)-hydroxy-(1S,5S)-cis-bicyclo[3.3.0]-octane} (39 mg, Yield: 100%) as nearly colorless oily product.

IR (neat): 3400, 1742 cm$^{-1}$.

NMRδ (CDCl$_3$): 5.50 (m, 2H), 5.20 (t, J=7 Hz, 1H), 4.20 (q, J=2 Hz, 3H), 1.75 (t, J=2 Hz, 3H), 1.30 (t, J=7 Hz, 3H), 1.20 (d, J=7 Hz, 3H).

Mass m/z: 388, 370.

REFERENCE EXAMPLE 65

{3(E)-(4'-Methoxycarbonylbutylidene)-6(S)-(3'(S)-hydroxy-3'-cyclopentyl-trans-1'-propenyl)-7(R)-hydroxy-(1S,5S)-cis-bicyclo[3.3.0]octane} (45 mg, 0.12 mmol) was dissolved in methanol (1 ml). A 10% aqueous sodium hydroxide solution (0.5 ml) was added to the thus prepared solution, followed by stirring at 0° C. for 13 hours. The reaction mixture was diluted with ether, and neutralized with a 10% aqueous hydrochloric acid solution. Then, methanol and ether were distilled out under reduced pressure. The resultant aqueous layer was adjusted to pH 4 to 5, and extracted with ethyl acetate. After the separated organic layer was dried with anhydrous magnesium sulfate, the solvent was distilled off to obtain {3(E)-(4'-carboxybutylidene)-6(S)-(3'(S)-hydroxy-3'-cyclopentyl-trans-1'-propenyl)-7(R)-hydroxy-(1S,5S)-cis-bicyclo[3.3.0]octane} (32 mg, Yield: 74%) as colorless viscous liquid. The product solidified when allowed to stand.

IR (neat): 3400, 1710 cm$^{-1}$.

NMRδ (CDCl$_3$): 5.54 (m, 2H), 5.24 (t, J=7 Hz, 1H), 3.50–4.00 (m, 2H).

Mass m/z: 348, 330, 312.

The thus obtained product is a carbacyclin analog. The usefulness thereof was published in '83 Inflammation Seminar-Prostaglandin Program Preliminary Text, p. 37, (Ono-Yakuhin-Kogyo-KK., Central Research Center, Akiyoshi Kawasaki).

REFERENCE EXAMPLE 66

The reaction was carried out following the same procedures as in Reference example 65 by using {3(E)-(4'-ethoxycarbonylbutylidene)-6(S)-(3'(S)-hydroxy-3'(S)-hydroxy-3'-cyclopentyl-trans-1'-propeneyl-7(R)-hydroxy-(1S,5S)-cis-bicyclo[3.3.0]octane} (45 mg, 0.12 mmol) to obtain {3(E)-(4'-carboxylbutylidene)-6(S)-(3'(S)-hydroxy-3'(S)-cyclopentyl-trans-1'-propenyl-7(R)-hydroxy-(1S,5S)-cis-bicyclo[3.3.0]octane} (33 mg, Yield: 80%) as white solid product. Each spectrum data thereof accorded with those obtained in Reference example 65.

REFERENCE EXAMPLE 67

The reaction was carried out following the same procedures as in Reference example 65 by using {3(E)-(4'-methoxycarbonylbutylidene)-6(S)-(3'(S)-hydroxy-4'(RS)-methyl-trans-1'-octen-6'-ynyl)-7(R)-hydroxy-(1S,5S)-cis-bicyclo[3.3.0]octane} (45 mg, 0.12 mmol) to obtain (3(E)-(4'-carboxylbutylidene)-6(S)-(3'(S)-hydroxy-4'(RS)-methyl-trans-1'-octen-6'-ynyl)-7(R)-hydroxy-(1S,5S)-cis-bicyclo-[3.3.0]octane} (35 mg, Yield: 80%) as viscous colorless oily product. Each spectrum data thereof accorded with those obtained in Reference example 52.

REFERENCE EXAMPLE 68

The reaction was carried out following the same procedures as in Reference example 65 by using {3(E)-(4'-ethoxycarbonylbutylidene)-6(S)-(3'(S)-hydroxy-4'(RS)-methyl-trans-1'-octen-6'-ynyl)-7(R)-hydroxy-(1S,5S)-cis-bicyclo[3.3.0]octane} (47 mg, 0.12 mmol) to obtain (3(E)-(4'-carboxylbutylidene)-6(S)-(3'(S)-hydroxy-4'(RS)-methyl-trans-1'-octen-6'-ynyl)-7(R)-hydroxy-(1S,5S)-cis-bicyclo-[3.3.0]octane} (35 mg, Yield: 80%) as viscous colorless oily product. Each spectrum data thereof accorded with those obtained in Reference example 67.

REFERENCE EXAMPLE 69

The reaction was carried out following the same procedures as in Reference example 65 by using {3(E)-(4'-methoxycarbonylbutylidene)-6(S)-(3'(S)-hydroxy-5'(R)-methyl-9'-methyl-trans-1'-decene-8'-enyl)-7(R)-hydroxy-(1S,5S)-cis-bicyclo[3.3.0]octane} (50 mg, 0.12 mmol) to obtain {3(E)-(4'-carboxylbutylidene)-6(S)-(3'(S)-hydroxy-5'(R)-methyl-9'-methyl-trans-1'-decene-8'-enyl)-7(R)-hydroxy-(1S,5S)-cis-bicyclo[3.3.0]octane} (39 mg, Yield: 80%) as viscous colorless oily products. Each spectrum data thereof accorded with those obtained in Reference example 53.

REFERENCE EXAMPLE 70

The reaction was carried out following the same procedures as in Reference example 67 by using {3(E)-(4'-methyl-9'-methyl-trans-1'-decene-8'-enyl)-7(R)-hydroxy(1S,5S)-cis-bicyclo[3.3.0]octane} (50 mg, 0.12 mmol) to obtain {3(E)-(4'-carboxybutylidene)-6(S)-(3'(S)-hydroxy-5'(R)-methyl-9'-methyl-trans-1'-decene-8'-enyl)-7(R)-hydroxy-(1S,5S)-cis-bicyclo[3.3.0]octane} (39 mg, Yield: 80%) as viscous colorless oily product. Each spectrum data thereof accorded with those obtained in Reference example 69.

TEST EXAMPLE 1

In the compounds synthsized by the method as described above, 9(0)-methano-$\Delta^{6(9\alpha)}$-PGI$_1$, for example, has a biological activity as mentioned below. When the rabbit serum was employed, it depressd a cohesion of platelets to be induced by adenosine diphosphate (ADP) at a potency of 1/10 to that of PGI$_2$, and it showed a potency of ½ to that of PGI$_2$ when the human blood was employed. As for the effects to the blood pressure, when rat was examined, it showed the same effect as that of PGI2 and showed blood pressure depressing action at a dosage of 0.1 μg/kg. An effect to the heart stroke frequencies thereof are almost the same as that of PGI$_2$, and increasing of the heart stroke frequencies were obserbed at a dosage of 1 μg/kg thereof in an experiment by using rats. As for an anti-fester action, it showed an activity at a low concentration of $10^{-6}$M in an experiment by using rabbit stomach, and it was the same strength as that of PGE$_2$. Cytotoxicity thereof are extremely weak and IC$_{50}$=5 μg/ml.

We claim:

1. A bicyclo[3.3.0]octane derivative represented by the formula:

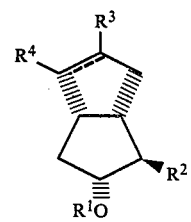

wherein

R$^1$ is a substitutent selected from the group consisting of a hydrogen atom and a protective group of a hydroxy group;

R$^2$ is a substituent selected from the group consisting of —CH$_2$OR$^5$,

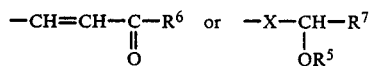

where

R$^5$ is a substituent selected from the group consisting of a hydrogen atom and a protective group of a hydroxy group, R$^6$ is a substituent selected from the group consisting of an alkyl group, an alkenyl group and an alkynyl group, said substituent being straight, branched or cyclic and having 5 to 10 carbon atoms, X is a substituent selected from the group consisting of a vinylene group and an acetylene group, and R$^7$ is a substituent selected from the group consisting of an alkyl group, an alkenyl group, and an alkynyl group, said substitutent being straight, branched or cyclic and having 5 to 10 carbon atoms;

R$^3$ is a substituent represented by the formula

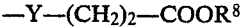

where

R$^8$ is a hydrogen atom or an alkyl group, and

Y is a vinylene group or an alkylene group;

R$^4$ is a hydroxy group when the compound is an octane derivative, or a hydrogen atom when the compound is an octane derivative; and dotted line denotes optional presence of a double bond;

provided that when R$^2$ is

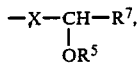

Y is not an ethylene group.

2. The bicyclo[3.3.0]octane derivative according to claim 1, wherein said derivative is a bicyclo[3.3.0]octene derivative represented by the formula:

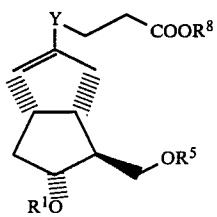

wherein $R^1$, $R^5$, $R^8$ and Y have the same meanings as defined in claim 1.

3. The bicyclo[3.3.0]octane derivative according to claim 1, wherein said derivative is a bicyclo[3.3.0]octane derivative represented by the formula:

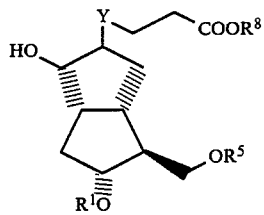

wherein $R^1$, $R^5$, $R^8$ and Y have the same meanings as defined in claim 1.

4. The bicyclo[3.3.0]octane derivative according to claim 1, wherein said derivative is a (3-oxo-1-alkenyl)-cis-bicyclo [3.3.0]octene derivative represented by the formula:

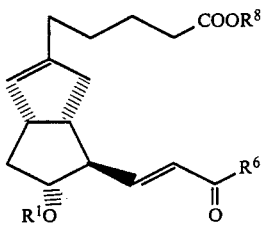

wherein $R^1$, $R^6$ and $R^8$ have the same meanings as defined in claim 1.

5. The bicyclo[3.3.0]octane derivative according to claim 1, wherein said derivative is a (4'-alkoxycarbonyl-1'alkenyl)-cis-bicyclo [3.3.0]octene derivative represented by the formula:

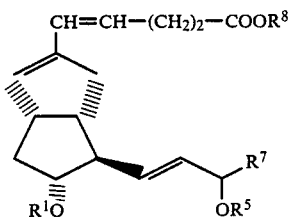

wherein $R^1$, $R^5$, $R^7$ and $R^8$ have the same meanings as defined in claim 1.

* * * * *